US010806775B2

(12) United States Patent
Daniell

(10) Patent No.: US 10,806,775 B2
(45) Date of Patent: Oct. 20, 2020

(54) ORAL DELIVERY OF ANGIOTENSIN CONVERTING ENZYME 2 (ACE2) OR ANGIOTENSIN-(1-7)-BIOENCAPSULATED IN PLANT CELLS ATTENUATES PULMONARY HYPERTENSIONS, CARDIAC DYSFUNCTION AND DEVELOPMENT OF AUTOIMMUNE AND EXPERIMENTALLY INDUCED OCULAR DISORDERS

(71) Applicant: THE TRUSTEES OF THE UNIVERSITY OF PENNSYLVANIA, Philadelphia, PA (US)

(72) Inventor: Henry Daniell, Media, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 16/425,243

(22) Filed: May 29, 2019

(65) Prior Publication Data

US 2019/0358304 A1 Nov. 28, 2019

Related U.S. Application Data

(60) Division of application No. 15/030,377, filed on Apr. 18, 2016, now Pat. No. 10,314,893, which is a
(Continued)

(51) Int. Cl.
| | |
|---|---|
| *A61K 38/48* | (2006.01) |
| *A61K 47/64* | (2017.01) |
| *C12N 15/82* | (2006.01) |
| *A61K 47/65* | (2017.01) |
| *C12N 9/48* | (2006.01) |
| *A61K 9/00* | (2006.01) |

(Continued)

(52) U.S. Cl.
CPC ........ *A61K 38/4813* (2013.01); *A61K 9/0053* (2013.01); *A61K 9/1664* (2013.01); *A61K 9/19* (2013.01); *A61K 9/5063* (2013.01); *A61K 36/23* (2013.01); *A61K 36/28* (2013.01); *A61K 36/31* (2013.01); *A61K 38/164* (2013.01); *A61K 38/22* (2013.01); *A61K 47/6415* (2017.08); *A61K 47/65* (2017.08); *C07K 14/28* (2013.01); *C12N 9/485* (2013.01); *C12N 15/8214* (2013.01); *C12N 15/8257* (2013.01); *C12Y 304/15001* (2013.01); *C12Y 304/17023* (2013.01); *C07K 2319/55* (2013.01); *Y02A 50/471* (2018.01)

(58) Field of Classification Search
CPC .. A61K 31/155; A61K 31/194; A61K 31/197; A61K 31/20; A61K 45/06; A61K 36/23; A61K 36/28; A61K 36/31; A61K 38/164; A61K 38/22; A61K 38/4813; A61K 47/6415; A61K 47/65; A61K 9/0053; A61K 9/1664; A61K 9/19; A61K 9/5063; C07C 279/14; C12N 5/0634; C12N 5/0647; C12N 15/8214; C12N 15/8257; C12N 9/485; C07K 14/28; C07K 2319/55; C12Y 304/15001; C12Y 304/17023

See application file for complete search history.

(56) References Cited

U.S. PATENT DOCUMENTS

| | | |
|---|---|---|
| 2012/0251520 A1 | 10/2012 | Penniger et al. |
| 2013/0183367 A1 | 7/2013 | Santos et al. |

FOREIGN PATENT DOCUMENTS

| | | |
|---|---|---|
| WO | 01/64023 A1 | 9/2001 |
| WO | 01/72959 A2 | 10/2001 |

(Continued)

OTHER PUBLICATIONS

Li et al., "Gene Therapy for Diabetic Retinopathy—Targeting the Renin-Angiotensin System. Biochemistry, Genetics and Molecular Biology", Gene Therapy—Tools and Potential Applications (Feb. 27, 2013), Chapter 19, pp. 467-491, ed. Francisco Martin Molina.
(Continued)

*Primary Examiner* — James H Alstrum-Acevedo
*Assistant Examiner* — Erinne R Dabkowski
(74) *Attorney, Agent, or Firm* — Kathleen D. Rigaut; Howson & Howson, LLP

(57) ABSTRACT

Emerging evidence indicates that diminished activity of the vasoprotective axis of the renin-angiotensin system, constituting angiotensin converting enzyme2 (ACE2) and its enzymatic product, angiotensin-(1-7) [Ang-(1-7)] contribute to pulmonary hypertension (PH). However, clinical success for long-term delivery of ACE2 or Ang-(1-7) would require stability and ease of administration to increase patient compliance. Chloroplast expression of therapeutic proteins enables their bioencapsulation within plant cells to protect from acids and gastric enzymes; fusion to a transmucosal carrier facilitates effective systemic absorption. Oral feeding of rats with bioencapsulated ACE2 or Ang-(1-7) attenuated monocrotaline (MCT)-induced increase in right ventricular systolic pressure, decreased pulmonary vessel wall thickness and improved right heart function in both prevention and reversal protocols. Furthermore, combination of ACE2 and Ang-(1-7) augmented the beneficial effects against cardiopulmonary pathophysiology induced by MCT administration.
Experiments have also been performed which indicate that this approach is also suitable for the treatment or inhibition of experimental uveitis and autoimmune uveoretinitis These studies provide proof-of-concept for a novel low-cost oral ACE2 or Ang-(1-7) delivery system using transplastomic technology for pulmonary and ocular disease therapeutics.

10 Claims, 32 Drawing Sheets
Specification includes a Sequence Listing.

Related U.S. Application Data continuation-in-part of application No. PCT/US2014/061428, filed on Oct. 20, 2014.

(60) Provisional application No. 61/952,078, filed on Mar. 12, 2014, provisional application No. 61/943,754, filed on Feb. 24, 2014, provisional application No. 61/892,717, filed on Oct. 18, 2013.

(51) Int. Cl.

| | | |
|---|---|---|
| A61K 9/16 | (2006.01) | |
| A61K 9/19 | (2006.01) | |
| A61K 9/50 | (2006.01) | |
| A61K 38/22 | (2006.01) | |
| A61K 38/16 | (2006.01) | |
| A61K 38/28 | (2006.01) | |
| A61K 36/23 | (2006.01) | |
| A61K 36/28 | (2006.01) | |
| A61K 36/31 | (2006.01) | |
| C07K 14/28 | (2006.01) | |

(56) References Cited

FOREIGN PATENT DOCUMENTS

| WO | 03/057834 A2 | 7/2003 |
|---|---|---|
| WO | 2004/005467 A2 | 1/2004 |
| WO | 2013/063049 A1 | 5/2013 |

OTHER PUBLICATIONS

Jiang, Teng et al., "Angiotensin-(1-7) inhibits autophagy in the brain of spontaneously hypertensive rats", Pharmacological Research, 71: 61-68 (2013).
Peyman, Gholam A., "Intravitreal Injection of Therapeutic Agents", Retnia, 29: 875-912 (2009).
Phipps, Paula A. et al., "Prevention of mucosally induced uveitis with a HSP60-derived peptide linked to cholera toxin B subunit", Eur. J. Immunal., 33:224-232 (2003).
Planck, S. et al., "Characterizing Extravascular Neutrophil Migration In Vivo in the Iris", Inflammation, 31(2): 105-111 (2008).
Qui, Y. et al., "Angiotensin-Coverting Enzyme 2 (ACE2) Activator Diminazene Aceturate Ameloriates Endotoxin-Induced Uveitis in Mice", Invest. Ophthalmol. Vis. Sci., 55:3809-3818 (2014).
Rawas-Qalaji, M. et al., "Advanced in Ocular Drug Delivery", Current Eye Research, 37(5): 345-356 (2012).
Read, R., "Uveitis: Advanced in Understanding Pathogenesis and Treatment", Current Rheumatology Reports, 8: 260-266 (2006).
Rosenbaum. J.T. et al., Endotoxin-induced uveitis in rats as a model for human disease: Nature, 286: 611-613 (1980).
Ruhlman, T., "Expression of cholera toxin B-proinsulin fusion protein in lettuce and tobacco chloroplasts—oral administration protects against development of insulitis in non-obese diabetic mice", Plant Biotechnology Journal, 5: 495-510 (2007).
Ruhlman, T. et al., "The Role of Heterologous Chloroplast Sequence Elements in Transgene Integration and Expression", Plant Physiology, 152: 2088-2104 (2010).
Ruiz, O. et al., "Metallothionein expression in chloroplasts enhances mercury accumulation and phytoremediation capability", Plant Biotechnol. J., 9(5): 609-617 (2011).
Santos, R. et al. "Expression of an angiotensin-(1-7)-producing fusion protein produces cardioprotective effecets in rats", Physiol. Genomics, 17: 292-299 (2004).
Santos, R. et al., "Angiotensin-(1-7) is an endogenous ligand for the G protein-coupled receptor Mas", PNAS, 100 (14): 8258-8263 (2003).
Santos, R. et al., "Reecent advances in the angiotensin-converting enzyme 2-angiotensin (1-7)-Mas axis", Exp. Physiol., 93: 519-527 (2008).

Satofuka, S. et al., "Suppression of Ocular Inflammation in Endotoxin-Induced Uveitis by Inhibiting Nonproteolytic Activation of Prorenin", Invest. Ophthalmol. Visual Sci. 47(6): 2686-2692 (2006).
Schermuly, R. et al., "Mechanisms of disease: pulmonary arterial hypertension", Nature Reviews/ Cardiology, 8: 443-455 (2011).
Shenoy, V. et al., "Diminazene Attenuated Pulmonary Hypertension and Improved Angiogenic Progenitor Cell Functions in Experimental Models", Am. J. Respir. Grit. Care Med., 187(6): 648-657 (2013).
Shenoy, V. et al., "The Angiotensin-Converting Enzyme 2/Angiogenesis-(1-7)/Mas Axis Confers Cardiopulmonary Protection against Lung Fibrosis and Pulmonary Hypertension", Am. J. Respir. Crit. Care Med., 182: 1065-1072 (2010).
Sherman, A. et al., "Suppression of inhibitor formation against FVIII in a murine model of hemophilia A by oral delivery of antigens bioencapsulated in plant cells", Blood, 124(10): 1659-1668 (2014).
Silvia, A.C. et al., "ACE2, angiotensin-(1-7) and Mas receptor axis in inflammation and fibrosis", British Journal of Pharmacology, 169: 477-492 (2013).
Simon, M., "Assessment and treatment of right ventricular failure", Nat. Rev. Cardiol., 10: 204-218 (2013).
Souza, L. et al., "Angiotensin-(1-7) Decreases LPS-Induced Inflammatory Response in Macrophages", J. Cell Physiol., 227: 2117-2122 (2012).
Stanford, M. et al., "Oral tolerization with peptide 336-351 linked to cholers toxin B subunit in preventing relapses of uveitis in Behcet's disease", Clin. Exp. Immunol., 137: 201-208 (2004).
Sun, J.B. et al., "Mucosally induced Immunological Tolerance, Regulatory T Cells and the Adjuvant Effect by Cholera Toxin B Subunit", Scandinavian Journal of Immunology, 71: 1-11 (2010).
Sutendra, G. et al., "Pulmonary Arterial Hypertension: Challenges in Translational Research and a Vision for Change", Science Translation Medicine, 5, 208sr5 (2013).
Thomas, G., "Furin at the Cutting Edge: From Protein Traffic to Embryogenesis and Disease", Nat. REv. Mol. Cell Biol., 3(10): 753-766 (2002).
Thurau, S.R. et al., "Oral tolerance in a murine model of relapsing experimental autoimmune uveoretinitis (EAU): induction of protective tolerance in primed animals", Clin. Exp. Immunol., 109: 370-376 (1997).
Tipnis, S. et al., "A Human Homolog of Angiotensin-coverting Enzyme", The Journal of Biological Chemistry, 275(43): 33238--33243 (2000).
Velkoska, E. et al., "Angiotensin-(1-7) infusion in associated with increased blood pressure and adverse cardiac remodeling in rats with subtotal nephrectomy", Clinical Science, 120: 335-345 (2011).
Verma, D. et al., "Oral delivery of bioencapsulated coagulation factor IX prevents inhibitor formation and fatal anaphylaxis in hemophilia B mice", PNAS, 107(15): 7101-7106 (2010).
Verma, A. et al., "ACE2 and Ang-(1-7) Confer Protection Against Development of Diabetic Retinopathy", Molecular Therapy, 20(1): 28-36 (2012).
Verma, D. et al., "A protocol for expresssion of foreign genes in chloroplasts", Nature Protocols, 3(4): 739-758 (2008).
Wagenaar, G. et al., "Agonists of MAS oncogene and angiotensin II type 2 receptors attenuate cardiopulmonary disease in rats with neonatal hyperoxia-induced lung injury", Am. J. Physiol. Lung Cell Mol. Physiol., 305: L341-L351.
Whitcup, S. et al., "Monoclonal Antibodies Against CD54 (ICAM-1) and CD11a (LFA-1) Prevent and Inhibit Endotoxin-Induced Uveitis", Exp. Eye Res., 60: 597-601 (1995).
Wilson, J.P., "Surface area of the small intestine in man", Gut, 8: 618621 (1967).
Yamada, K et al., "Converting Enzyme Determines Plasma Clearance of Angiotensin-(107)", Hypertension, 32: 496-502 (1998).
Yamazato, Y. et al., "Prevention of Pulmonary Hypertension by Angiotensin Converting Enzyme 2 Gene Transfer", Hypertension, 54(2): 365-371 (2009).
Yu, R.K. et al., "Functional Roles of Gangliosides in Neurodevelopment: An Overview of Recent Advances", Neurochem. Res., 37: 1230-1244 (2012).

(56) References Cited

OTHER PUBLICATIONS

Zhang, R. et al., "The 2.4 A Crystal Structure of Cholera Toxin B Subunit Pentamer: Choleragenoid", J. Mol. Biol., 251: 550-562 (1995).
Zhong, J. et al., "Prevention of Angiotensin II-Mediated Renal Oxidative Stress, Inflammation, and Fibrosis by Angiotensin-Converting Enzyme 2", Hypertension, 57: 341-322 (2011).
Zimran. A. et al., "Pivotal trial with plant cell-expressed recombinant glucocerebrosidase, tailglucerase alfa, a novel enzyme replacement therapy for Gaucher disease", Blood, 118(22): 5767-5773 (2011).
Zou, Z. et al., "Angiotensin-converting enzyme 2 protects from lethal avian influenza A H5N1 infections", Nature Communications, 5: 3594 (2014).
Fraga-Silva, Rodrigo Araujo et al., "Opportunities for Targeting the Angiotensin-Converting Enzyme 2/Angiotensin-(1-7)/Mas Receptor Pathway in Hypertension", Curr. Hypertens. Rep., 15: 31-38 (2013).
Shenoy, Vivayak et al., "Oral Delivery of Angiotensin-Converting Enzyme 2 and Angiotensin-(1-7) Bioencapsulated in Plant Cells Attenuates Pulmonary Hypertension", Hypertension, 64(6): 1248-1259 (2014).
Extended European Search Report, dated Apr. 4, 2017, issued in corresponding European Application No. 14859090.9.
Johnson, Jennifer A., "ACE2 Improves Right Ventricular Function in a Pressure Overload Model", PLOS, Published: Jun. 10, 2011.
Limaye, Arati, "Receptor-mediated oral delivery of a bioencapsulated green fluorescent protein expressed in transgenic chloroplasts into the mouse circulatory system", FASEB J. May 2006; 20(7): 959-961.
Lim, Soon, "Production of biologically active human thioredoxin 1 protein 4 in lettuce chloroplasts", Plant Mol Biol, Feb. 2011.
Agarwal, R. et al., "Rodent Models of Experimental Autoimmune Uveitis", Methods Mol. Biol., 22: 720-724 (2012).
Allfred, A. et al., "Pathways for angiotensin-(1-7) metabolism in pulmonary and renal tissues", Am. J. Physiol. Renal Physiol., 279: F841-F850 (2000).
Arlen, P. et al., "Field production and functional evaluation of chloroplast-derived interferon-α2b", Plant Biotechnol., J., 5(4): 511-525 (2007).
Boyhan, D. et al., "Low-cost production of proinsulin in tobacco and lettuce chloroplasts for injectable or oral delivery of functional insulin and C-peptide", Plant Biotechnol. J., 9(5): 585-598 (2011).
Bradford, C. et al., "Targeting the Vasoprotective Axis of the Renin-Angiotensin System: A Novel Strategic Approach to Pulmonary Hypertensive Therapy", Curr. Hypertens. Rep., 12(4): 212-219 (2010).
Chen, J. et al., "Use of Optical Coherence Tomography and Electroretinography to Evaluate Retinal Pathology in a Mouse Model of Autoimmune Uveitis", PLOS ONE, 8(5): e63904 (2013).
Copland, D. et al., "The Clinical Time-Course of Experimental Autoimmune Uveoretinitis Using Topical Endoscopic Fundal Imaging with Histologic and Cellular Infiltrate Correlation", Investigative Ophthalmology & Visual Science, 49 (12): 5458-5465 (2008).
Dai, H. et al., "The Changes of Serum Angiotensin-Converting Enzyme 2 in Patients with Pulmonary Arterial Hypertension due to Congenital Heart Disease", Cardiology, 124: 208-212 (2013).
Daniell, H. et al., "Optimnization of codon composition and regulatory elements for expression of human insulin like growth factor-1 in transgenic chloroplasts and evaluation of structural identity and function", BMC Biotechnology, 9: 33 (2009.
Daniell, H. et al., "Plant-made vaccine antigens and biopharmaceuticals", Trends in Plant Science, 14(12): 669-679 (2009).
Daniell, H. et al., "Transgene containment by maternal inheritance: Effective or elusive?", PNAS, 104(17) 6879-6880 (2007).
Davoodi-Semiromi, A. et al., "Chloroplast-derived vaccine antigens confer dual immunity against cholera and malaria by oral or injectable delivery", Plant Biotechnology Journal, 8: 223-242 (2010).

Decosa, B. et al., "Overexpression of the Bt cry2Aa2 operon in chloroplasts leads to formation of insecticidal crystals", Nature Biotechnology, 19: 71-74 (2001).
Donoghue, M. et al., "A Novel Angiotensin-Converting Enzyme-Related Carboxypeptidase (ACE2) Converts Angiotensin I to Angiotensin 1-9", Circulation Research, 87: e1-e9 (2000).
Dorfmuller, P. et al., "Inflammation in pulmonary arterial hypertension", Eur. Respir. J., 22: 358-363 (2003).
Duckert, P. et al., "Prediction of proprotein convertase cleavage sites", Protein Engineering, Design & Selection, 17 (1): 107-112 (2004).
Ferreira, A., "Evidence for Angiotensin-converting Enzyme 2 as a Therapeutic Target for the Prevention of Pulmonary Hypertension", Am. J. Respir. Crit. Care Med, 179: 1048-1054 (2009).
Fishman, P. et al., "Uptake and metabolism of exogenous gangliosides by cultured cells: effect of choleragen on the turnover of GM1", Journal of Lipid Research, 24: 1002-1011 (1983).
Fletcher, E. et al., "The renin-angiotensin system in retinal health and disease: Its influence on neurons, glia and the vasculature", Progress in Retinal and Eye Research, 29: 284-311 (2010).
Flint, H. et al., "Microbial degradation of complex carbohydrates in the gut", Gut Microbes, 3: 289-306 (2012).
Flint, H. et al., "Polysaccharide utilization by gut bacteria: potential for new insights from genomic analysis", Nature Reviews/Microbiology, 6: 121-131 (2008).
Grobe, J. et al., "Chronic angiotensin-(1-7) prevents cardiac fibrosis in DOCA-salt model of hypertension", Am. J. Physiol. Heart Circ. Physiol., 290: H2417-H2423 (2006).
Grobe, J. et al., "Prevention of angiotensin II-induced cardiac remodeling by angiotensin-(1-7)", Am. J. Physiol. Heart Circ. Physiol., 292: H736-H742 (2007).
Hamming, I. et al., "Tissue distribution of ACE2 protein, the functional receptor for SARS coronavirus. A first step in understanding SARS pathogenesis", J. Pathol., 203: 631-637 (2004).
Hanking, D. et al., "Interphotoreceptor Retinoid Binding Protein Peptide-Induced Uveitis in B10.R111 Mice: Characterization of Disease Parameters and Immunomodulation", Exp. Eye. Res., 72: 341-350 (2001).
Hill, David R. et al., "Oral cholera vaccines: use in clinical practice", Lancet Infect. Dis., 6: 361-73 (2006).
Holmgren, J. et al., Interaction of cholera toxin and membrane GM1 ganglioside of small intestine, Proc. Natl. Acad. Sci. USA, 72(7): 2520-2524 (1975).
Karlin, S. et al., "What Drives Codon Choices in Human Genes?", J. Mol. Biol., 262: 459-472 (1996).
Kim, N. et al., "Oral Administration of Collagen Conjugated with Cholera Toxin Induces Tolerance to Type II Collagen and Suppresses Chondritis in an Animal Model of Autoimmune Ear Disease", Ann. Otol. Rhinol. Laryngol, 110: 646-654 (2001).
Kleinsasser, A. et al., "Recombinant Angiotensin-Converting Enzyme 2 Suppresses Pulmonary Vasoconstriction in Acute Hypoxia", Wilderness & Environmental Medicine, 23: 24-30 (2012).
Kohli, N. et al., "Oral Delivery of Bioencapsulated Proteins Across Blood-Brain and Blood-Retinal Barriers", Molecular Therapy, 22(3): 535-546 (2014).
Kwon, K. et al., "Oral delivery of bioencapsulated exendin-4 expressed in chloroplasts lowers blood glucose level in mice and stimulatesinsulin secretion in beta-TC6 cells", Plant Biotechnology Journal, 11: 77-86 (2013).
Kwon, K et al., "Oral delivery of human biopharmaceuticals, autoantigens and vaccine antigen bioencapsulated in plant cells", Advanced Drug Delivery Reviews, 65: 782-799 (2013).
Lakshmi, P. et al., "Low Cost Tuberculosis Vaccine Antigens in Capsules: Expression in Chloroplasts, Bio-Encapsulation, Stability and Functional Evaluation in Vitro", PLoS ONE, 8(1); e54708 (2013).
Li, X. et al., "Angiotensin converting enzyme-2 is protective but downregulated in human and experimental lung fibrosis", Am. J. Physiol. Lung Cell Mol. Physiol., 295: L178-L185 (2008).
Limaye, A. et al., "Receptor-mediated oral delivery of a bioencapsulated green fluorescent protein expressed in transgenic chloroplasts into the mouse circulatory system", FASEB J., 20(7): 959-961 (2006).

(56) References Cited

OTHER PUBLICATIONS

Long, L. et al., "Chloroquine Prevents Progression of Experimental Pulmonary Hypertension via Inhibition of Autophagy and Lysomal Bone Morphogenetic Protein Type II Receptor Degradation", Circ. Res., 112: 1159-1170 (2013).

Iusuf, D. et al., "Angiotensin-(1-7): Pharmacological properties and pharmacotherapeutic perspectives", European Journal of Pharmacology, 585: 303-312 (2008).

Mager, I. et al., "From Gut to Brain: Bioencapsulated Therapeutic Protein Reduces Amyloid Load Upon Oral Delivery", Molecular Therapy, 22(3): 485-486 (2014).

Marian, A.J. et al., "The Discovery of the ACE2 Gene", Circ. Res., 112: 1307-1309 (2013).

Miyahara, S. et al., "In Vivo Three-Dimensional Evaluation of Leukocyte Behavior in Retinal Microcirculation of Mice", Invest. Ophthalmol. Vis. Sci., 45: 4197-4201 (2004).

Miyata, T. et al., "Physicochemically stable cholera toxin B subunit pentamer created by peripheral molecular aonstraints imposed by de novo-introduced intersubunit disulfide crosslinks", Vaccine, 30: 4225-4232 (2012).

Mochizuki, M. et al., "Immunological homeostasis of the eye", Progress in Retinal and Eye Research, 33: 10-27 (2013).

Mordwinkin, N. et al., "Pharmakinetics, Pharmacodynamics and Drug Metabolism", Journal of Pharmaceutical Sciences, 101(1): 373-380 (2012).

Morrell, N. et al., "Angiotensin Converting Enzyme Expression is Increased in Small Pulmonary Arteries of Rats with Hypoxia-induced Pulmonary Hypertension", J. Clin. Invest., 96: 1823-1833 (1995).

Noda, K et al., "Inhibition of vascular adhesion protei-1 suppresses endotoxin-induced uveitis", FASEB J., 22: 1094-1103 (2008).

Odumosu, O. et al., "Suppression of dendritic cell activation by diabetes autoantigens linked to the cholera toxin B subunit", Immunobiology, 216: 447-456 (2011).

Oudit, G. et al., "Human Recombinant ACE2 Reduces the Progression of Diabetic Nephropathy", Diabetes, 59: 529-538 (2010).

Passo-Silva, D. et al., "Angiotensin-(1-7): beyond the cardio-renal actions", Clinical Science, 124: 443-456 (2013).

Paul, M. et al., Physiology of Local Renin-Angiotensin Systems:, Physiol. Rev., 86: 747-803 (2006).

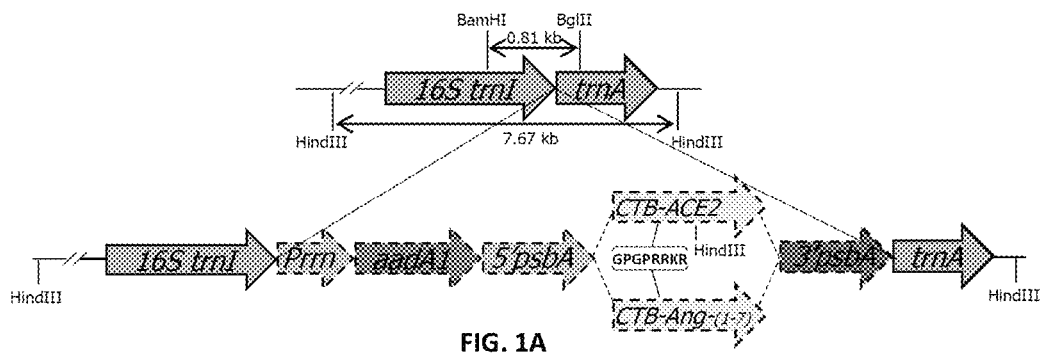
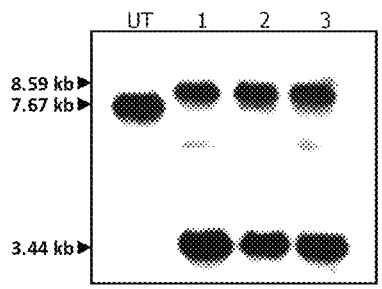
FIG. 1B
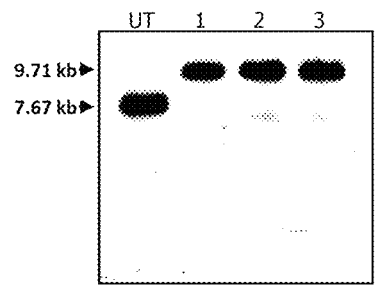
FIG. 1C
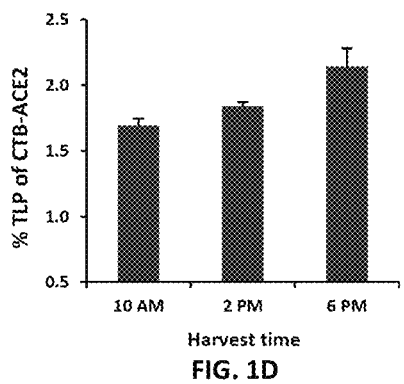
FIG. 1D
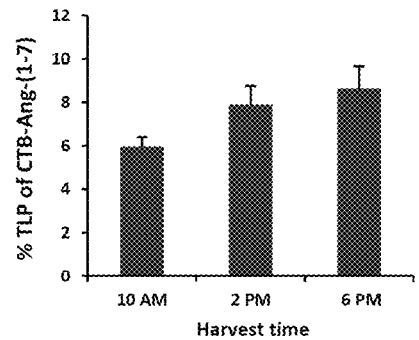
FIG. 1E
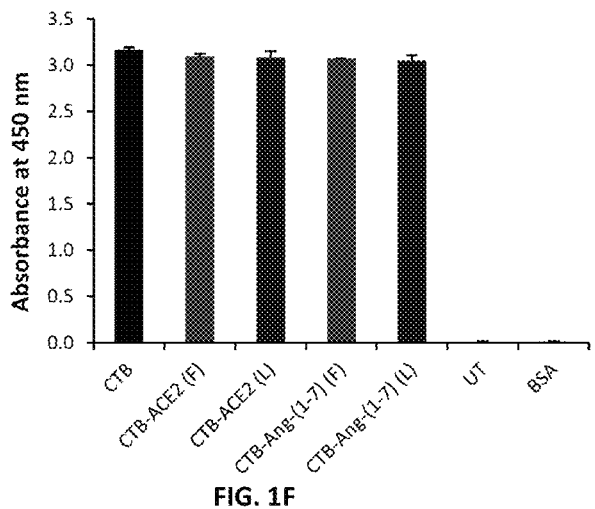
FIG. 1F
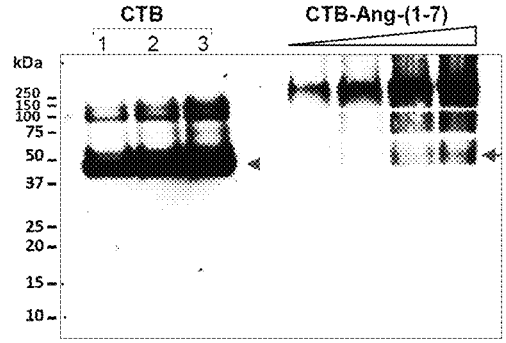
FIG. 1G

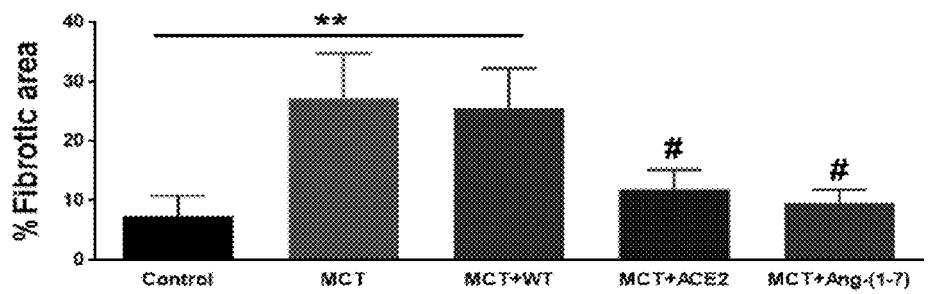
FIG. 6A
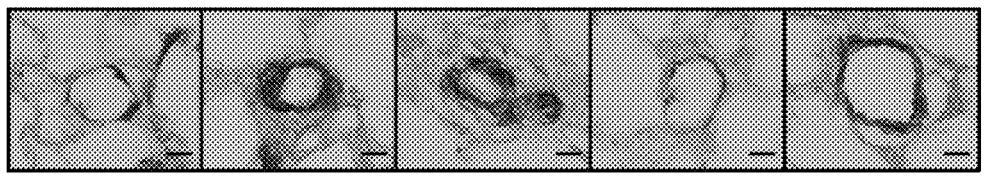
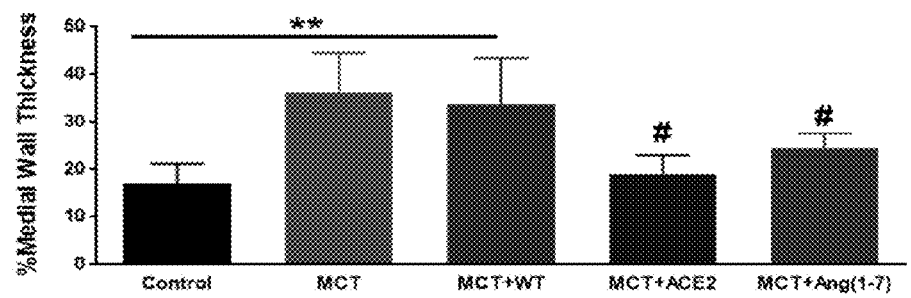
FIG. 6B
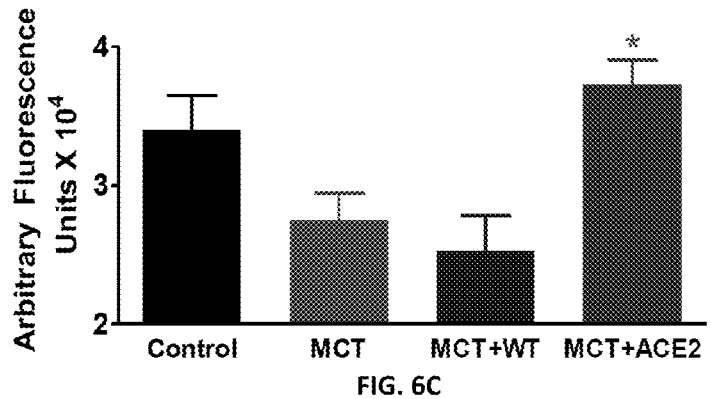
FIG. 6C

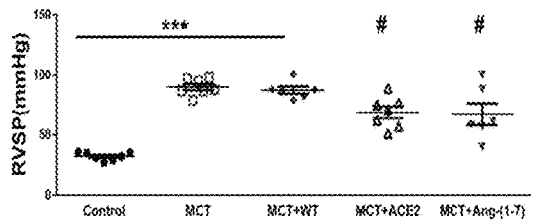
FIG. 7A
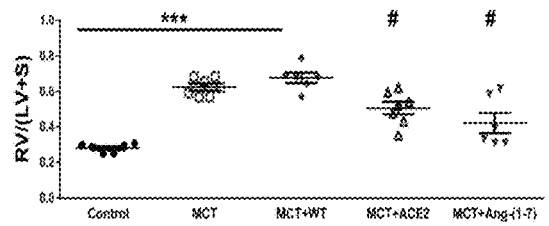
FIG. 7B
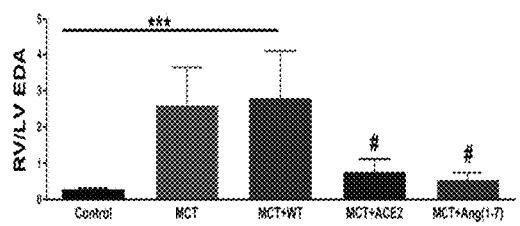
FIG. 7C
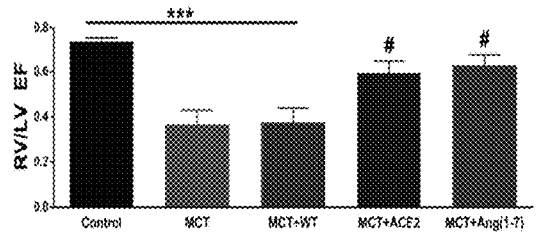
FIG. 7D
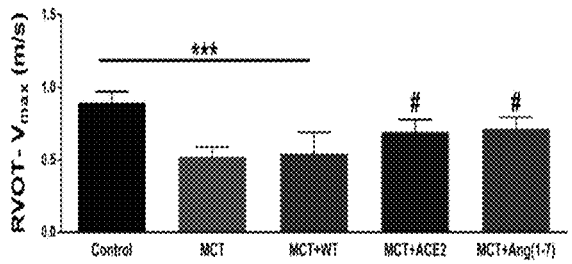
FIG. 7E
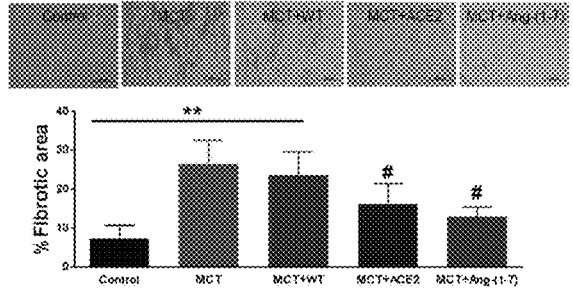
FIG. 7F
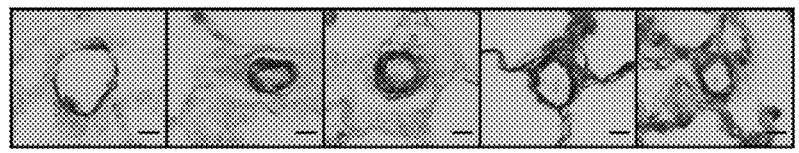
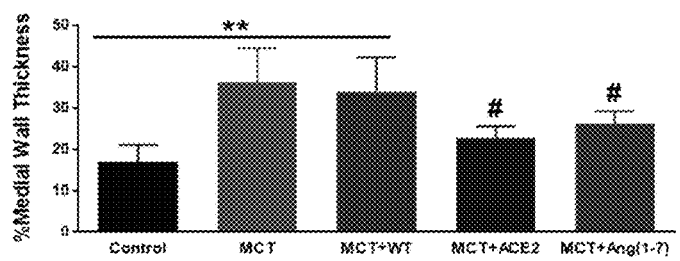
FIG. 7G

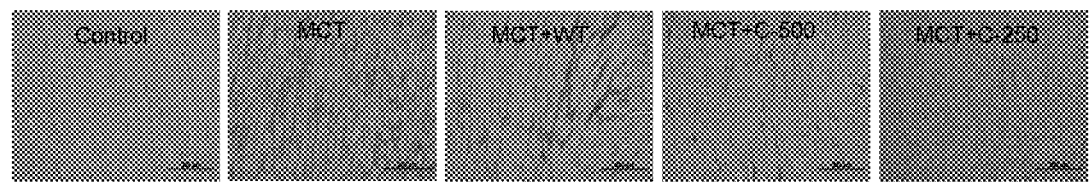
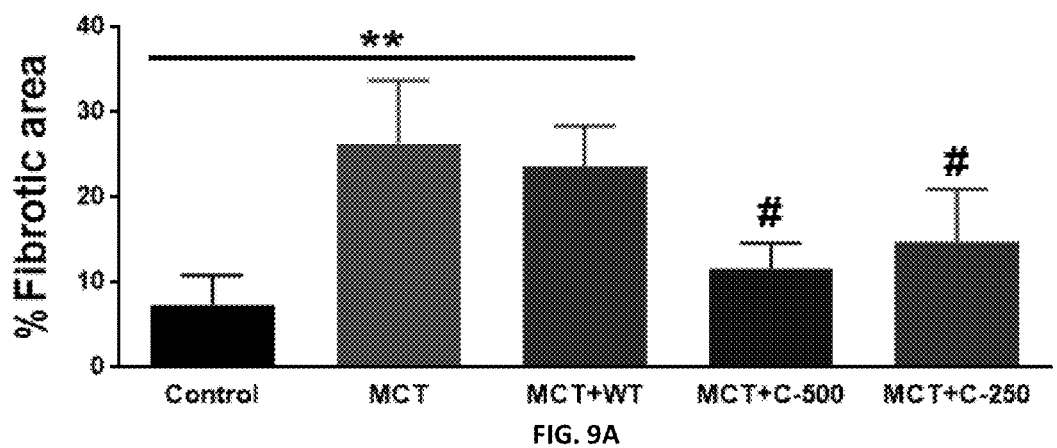
FIG. 9A
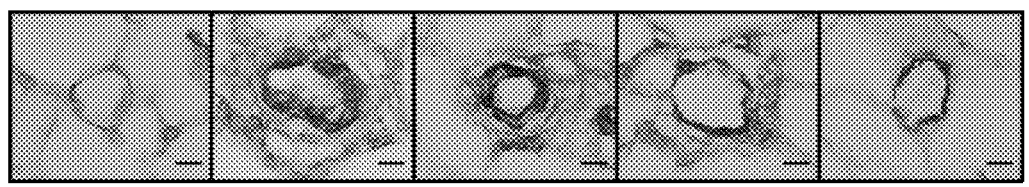
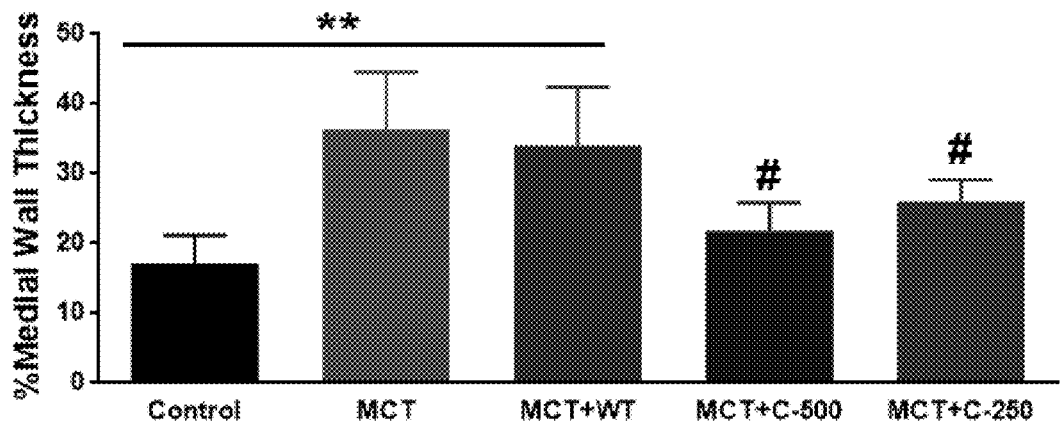
FIG. 9B

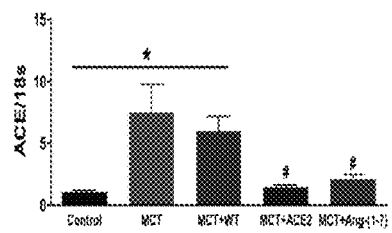
FIG. 10A
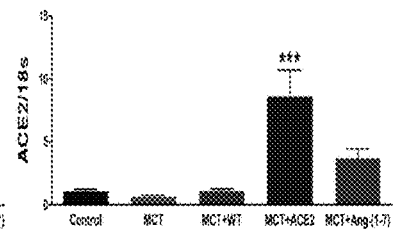
FIG. 10B
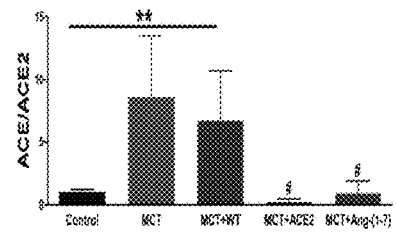
FIG. 10C
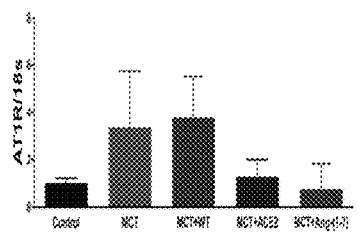
FIG. 10D
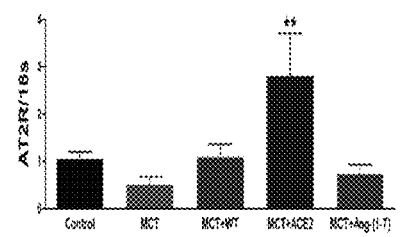
FIG. 10E
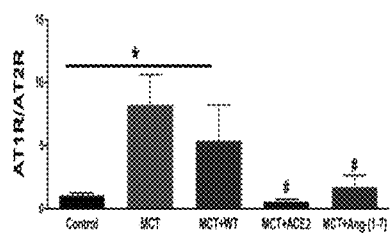
FIG. 10F
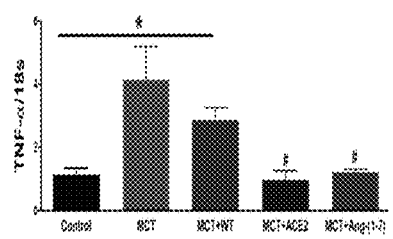
FIG. 10G
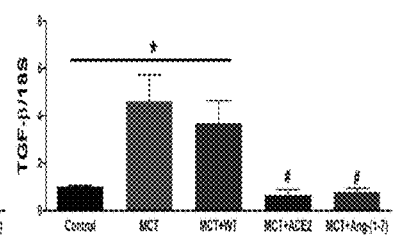
FIG. 10H
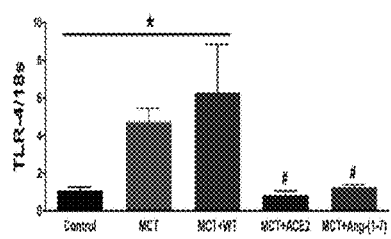
FIG. 10I
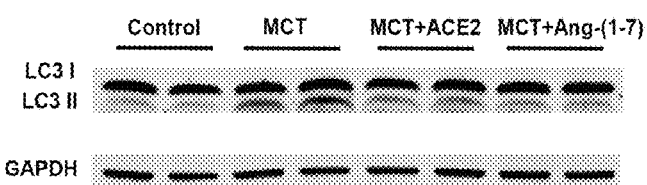
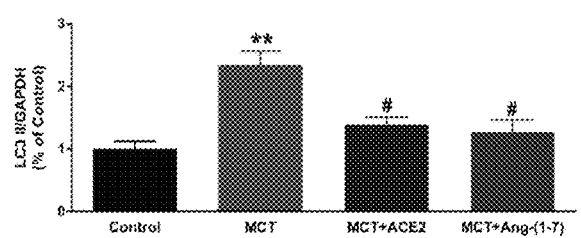
FIG. 10J

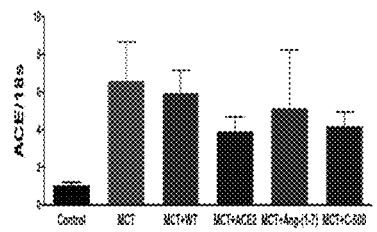
FIG. 11A
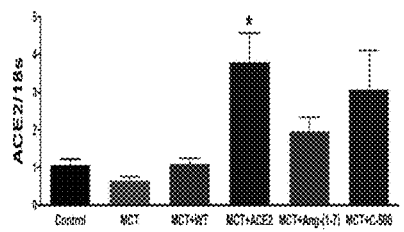
FIG. 11B
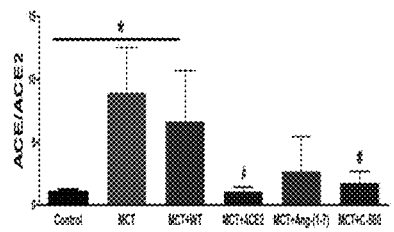
FIG. 11C
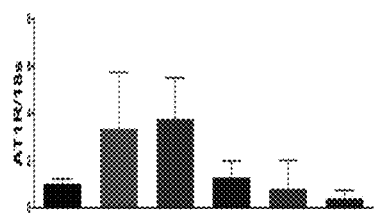
FIG. 11D
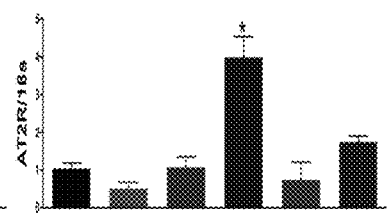
FIG. 11E
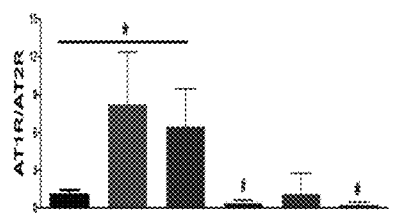
FIG. 11F
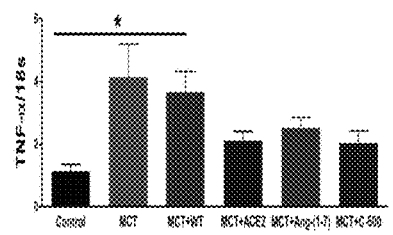
FIG. 11G
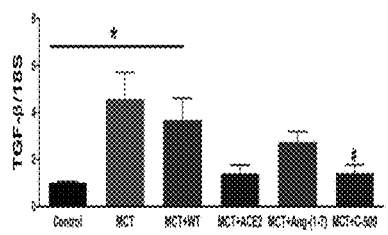
FIG. 11H
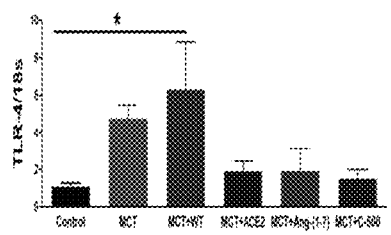
FIG. 11I
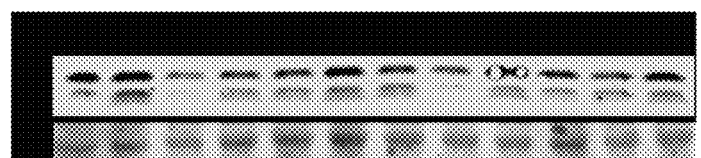
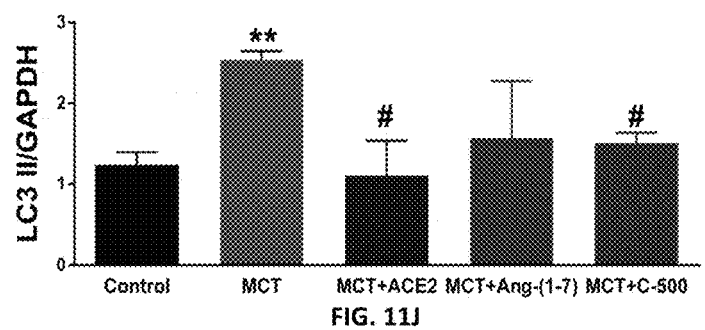
FIG. 11J

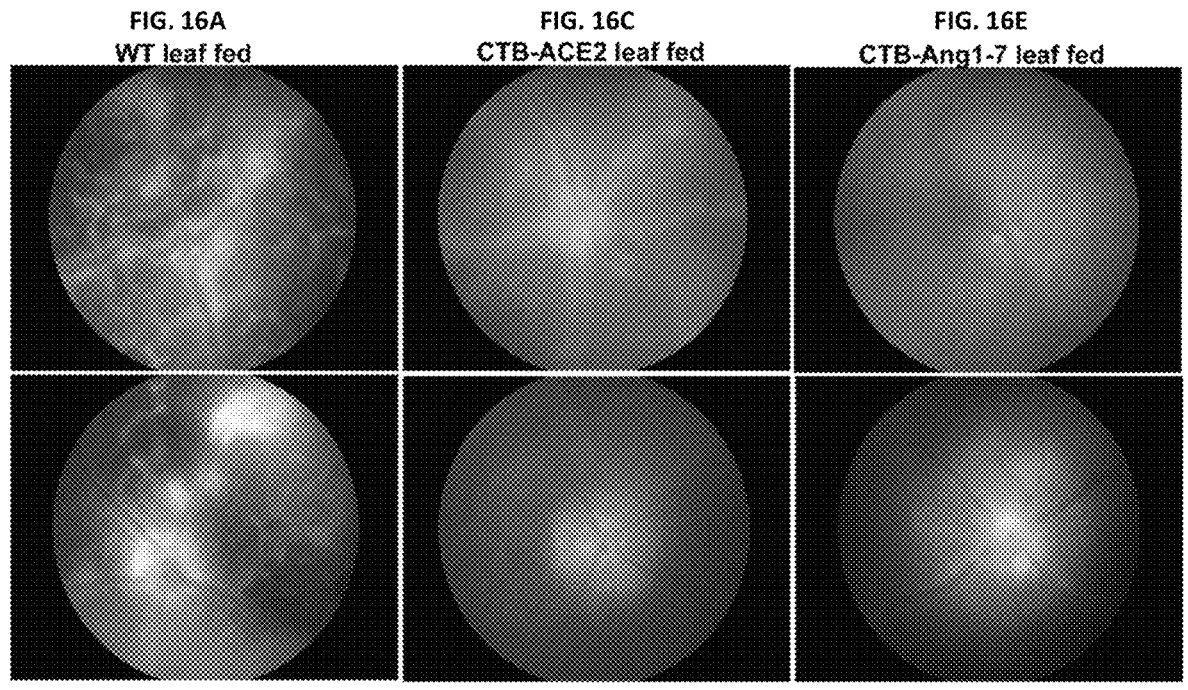
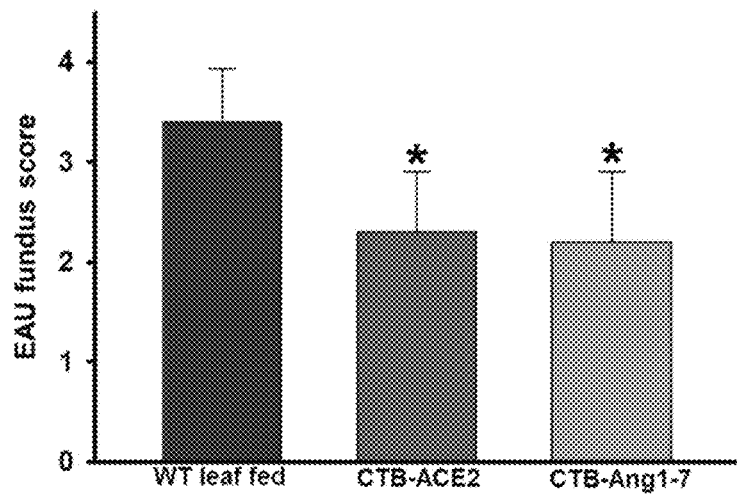
WT leaf fed
FIG. 16C
CTB-ACE2 leaf fed
FIG. 16E
CTB-Ang1-7 leaf fed
FIG. 16B
FIG. 16D
FIG. 16F
FIG. 16E CTB-Ang

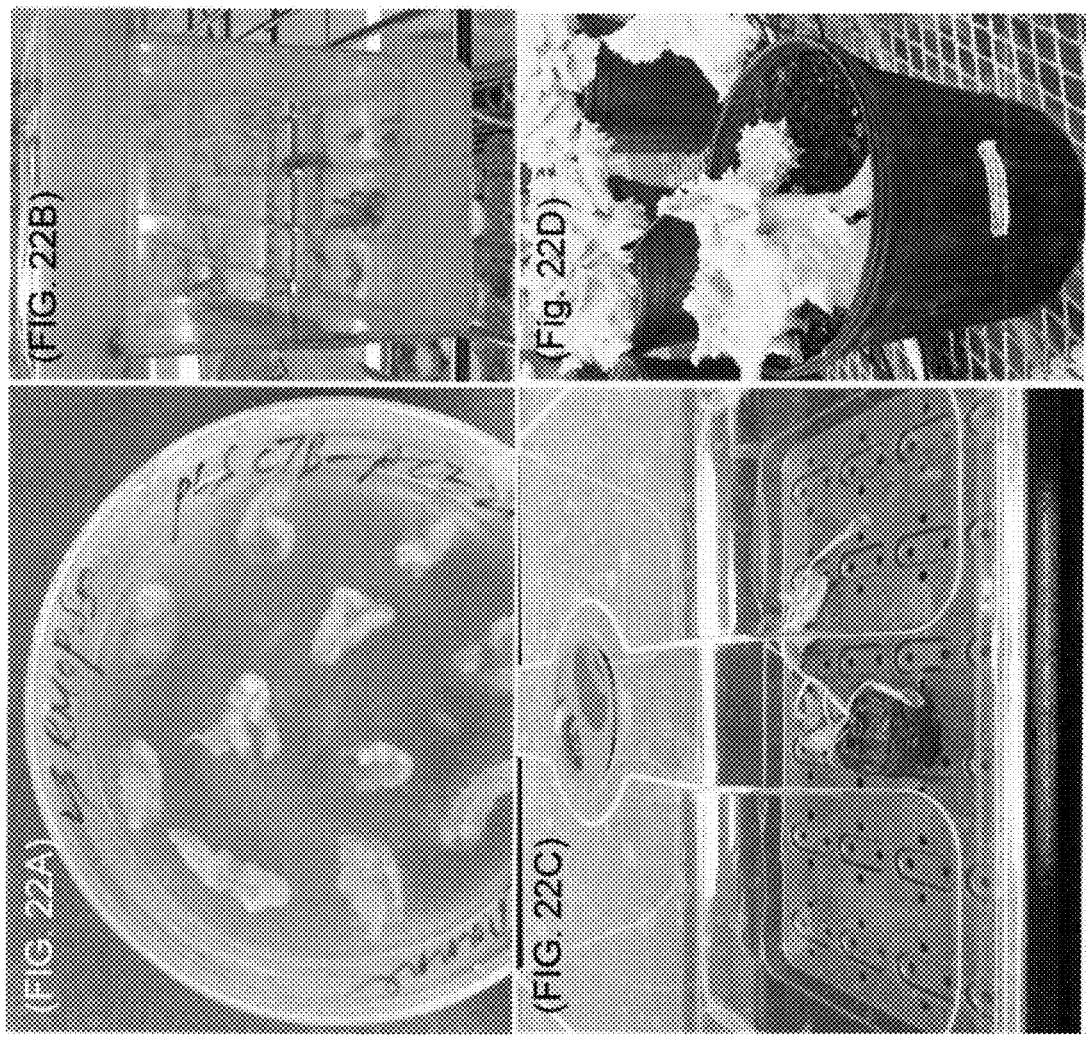

SEQUENCE LISTING

<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: hinge sequence

<400> SEQUENCE: 1

Gly Pro Gly Pro
1

<210> SEQ ID NO 2
<211> LENGTH: 4
<212> TYPE: PRT
<213> ORGANISM: Artificial Sequence
<220> FEATURE:
<223> OTHER INFORMATION: furin cleavage site

<400> SEQUENCE: 2

Arg Arg Lys Arg
1

<210> SEQ ID NO 3
<211> LENGTH: 8
<212> TYPE: PRT
<213> ORGANISM: Artificial Sequence
<220> FEATURE:
<223> OTHER INFORMATION: hinge and furin cleavage site

<400> SEQUENCE: 3

Gly Pro Gly Pro Arg Arg Lys Arg
1               5

<210> SEQ ID NO 4
<211> LENGTH: 20
<212> TYPE: DNA
<213> ORGANISM: Artificial Sequence
<220> FEATURE:
<223> OTHER INFORMATION: IL-6 forward primer

<400> SEQUENCE: 4
tcggcaaacc tagtgcgtta                                           20

<210> SEQ ID NO 5
<211> LENGTH: 21
<212> TYPE: DNA
<213> ORGANISM: Artificial Sequence
<220> FEATURE:
<223> OTHER INFORMATION: IL-6 reverse primer

<400> SEQUENCE: 5
ccaagaaacc atctggctag g                                         21

<210> SEQ ID NO 6
<211> LENGTH: 21
<212> TYPE: DNA
<213> ORGANISM: Artificial Sequence
<220> FEATURE:
<223> OTHER INFORMATION: IL-1B forward primer

<400> SEQUENCE: 6
aaagcctcgt gctgtcggac c                                         21

<210> SEQ ID NO 7

```
<211> LENGTH: 20
<212> TYPE: DNA
<213> ORGANISM: Artificial Sequence
<220> FEATURE:
<223> OTHER INFORMATION: IL-1B reverse primer

<400> SEQUENCE: 7
cagctgcagg gtgggtgtgc                                               20

<210> SEQ ID NO 8
<211> LENGTH: 20
<212> TYPE: DNA
<213> ORGANISM: Artificial Sequence
<220> FEATURE:
<223> OTHER INFORMATION: TNF-a forward primer

<400> SEQUENCE: 8
aggcgccaca tctccctcca                                               20

<210> SEQ ID NO 9
<211> LENGTH: 20
<212> TYPE: DNA
<213> ORGANISM: Artificial Sequence
<220> FEATURE:
<223> OTHER INFORMATION: TNF-a reverse primer

<400> SEQUENCE: 9
cggtgtgggt gaggagcacg                                               20

<210> SEQ ID NO 10
<211> LENGTH: 20
<212> TYPE: DNA
<213> ORGANISM: Artificial Sequence
<220> FEATURE:
<223> OTHER INFORMATION: ICAM-1 forward primer

<400> SEQUENCE: 10
agatgacctg cagacggaag                                               20

<210> SEQ ID NO 11
<211> LENGTH: 20
<212> TYPE: DNA
<213> ORGANISM: Artificial Sequence
<220> FEATURE:
<223> OTHER INFORMATION: ICAM-1 reverse primer

<400> SEQUENCE: 11
ggctgagggt aaatgctgtc                                               20

<210> SEQ ID NO 12
<211> LENGTH: 21
<212> TYPE: DNA
<213> ORGANISM: Artificial Sequence
<220> FEATURE:
<223> OTHER INFORMATION: MCP-1 forward primer

<400> SEQUENCE: 12
ccccactcac ctgctgctac t                                             21

<210> SEQ ID NO 13
<211> LENGTH: 21
<212> TYPE: DNA
<213> ORGANISM: Artificial Sequence
<220> FEATURE:
<223> OTHER INFORMATION: MCP-1 reverse primer

<400> SEQUENCE: 13
```
ggcatcacag tccgagtcac a                                              21

<210> SEQ ID NO 14
<211> LENGTH: 20
<212> TYPE: DNA
<213> ORGANISM: Artificial Sequence
<220> FEATURE:
<223> OTHER INFORMATION: B-actin forward primer

<400> SEQUENCE: 14
agcagatgtg gatcagcaag                                                20

<210> SEQ ID NO 15
<211> LENGTH: 20
<212> TYPE: DNA
<213> ORGANISM: Artificial Sequence
<220> FEATURE:
<223> OTHER INFORMATION: B-actin reverse primer

<400> SEQUENCE: 15
acagaagcaa tgctgtcacc                                                20

<210> SEQ ID NO 16
<211> LENGTH: 21
<212> TYPE: DNA
<213> ORGANISM: Artificial Sequence
<220> FEATURE:
<223> OTHER INFORMATION: MAS receptor forward primer

<400> SEQUENCE: 16
agggtgactg actgagtttg g                                              21

<210> SEQ ID NO 17
<211> LENGTH: 20
<212> TYPE: DNA
<213> ORGANISM: Artificial Sequence
<220> FEATURE:
<223> OTHER INFORMATION: MAS receptor reverse primer

<400> SEQUENCE: 17
gaaggtaaga ggacaggagc                                                20

<210> SEQ ID NO 18
<211> LENGTH: 20
<212> TYPE: DNA
<213> ORGANISM: Artificial Sequence
<220> FEATURE:
<223> OTHER INFORMATION: AT1Ra forward primer

<400> SEQUENCE: 18
atcggactaa atggctcacg                                                20

<210> SEQ ID NO 19
<211> LENGTH: 20
<212> TYPE: DNA
<213> ORGANISM: Artificial Sequence
<220> FEATURE:
<223> OTHER INFORMATION: AT1Ra reverse primer

<400> SEQUENCE: 19
acgtgggtct ccattgctaa                                                20

<210> SEQ ID NO 20
<211> LENGTH: 20
<212> TYPE: DNA

<213> ORGANISM: Artificial Sequence
<220> FEATURE:
<223> OTHER INFORMATION: AT1Rb forward primer

<400> SEQUENCE: 20
agtggagtga gagggttcaa 20

<210> SEQ ID NO 21
<211> LENGTH: 20
<212> TYPE: DNA
<213> ORGANISM: Artificial Sequence
<220> FEATURE:
<223> OTHER INFORMATION: AT1Rb reverse primer

<400> SEQUENCE: 21
gggcattgaa gacatggtat 20

<210> SEQ ID NO 22
<211> LENGTH: 20
<212> TYPE: PRT
<213> ORGANISM: Artificial Sequence
<220> FEATURE:
<223> OTHER INFORMATION: IRBP (161-180)

<400> SEQUENCE: 22

Ser Gly Ile Pro Tyr Ile Ile Ser Tyr Leu His Pro Gly Asn Thr Ile
1 5 10 15

Leu His Val Asp
20

<210> SEQ ID NO 23
<211> LENGTH: 2754
<212> TYPE: DNA
<213> ORGANISM: Artificial Sequence
<220> FEATURE:
<223> OTHER INFORMATION: Native CTB-ACE2

<400> SEQUENCE: 23
atgacacctc aaaatattac tgatttgtgt gcagaatacc acaacacaca aatacatacg 60
ctaaatgata agatattttc gtatacagaa tctctagctg gaaaaagaga gatggctatc 120
attactttta agaatggtgc aacttttcaa gtagaagtac caggtagtca acatatagat 180
tcacaaaaaa aagcaattga aaggatgaag gataccctga ggattgcata tcttactgaa 240
gctaaagtcg aaaagttatg tgtatggaat aataaaacgc ctcatgcgat tgccgcaatt 300
agtatggcaa atgggcccgg gccccggcgt aaacgtatgt caagctcttc ctggctcctt 360
ctcagccttg ttgctgtaac tgctgctcag tccaccattg aggaacaggc caagacattt 420
ttggacaagt ttaaccacga agccgaagac ctgttctatc aaagttcact tgcttcttgg 480
aattataaca ccaatattac tgaagagaat gtccaaaaca tgaataatgc tggggacaaa 540
tggtctgcct ttttaaagga acagtccaca cttgcccaaa tgtatccact acaagaaatt 600
cagaatctca cagtcaagct tcagctgcag gctcttcagc aaaatgggtc ttcagtgctc 660
tcagaagaca agagcaaacg gttgaacaca attctaaata caatgagcac catctacagt 720
actggaaaag tttgtaaccc agataatcca caagaatgct tattacttga accaggtttg 780
aatgaaataa tggcaaacag tttagactac aatgagaggc tctgggcttg ggaaagctgg 840
agatctgagg tcggcaagca gctgaggcca ttatatgaag agtatgtggt cttgaaaaat 900
gagatggcaa gagcaaatca ttatgaggac tatggggatt attggagagg agactatgaa 960
gtaaatgggg tagatggcta tgactacagc cgcggccagt tgattgaaga tgtggaacat 1020

```
acctttgaag agattaaacc attatatgaa catcttcatg cctatgtgag ggcaaagttg   1080
atgaatgcct atccttccta tatcagtcca attggatgcc tccctgctca tttgcttggt   1140
gatatgtggg gtagattttg gacaaatctg tactctttga cagttccctt tggacagaaa   1200
ccaaacatag atgttactga tgcaatggtg gaccaggcct gggatgcaca gagaatattc   1260
aaggaggccg agaagttctt tgtatctgtt ggtcttccta atatgactca aggattctgg   1320
gaaaattcca tgctaacgga cccaggaaat gttcagaaag cagtctgcca tcccacagct   1380
tgggacctgg ggaagggcga cttcaggatc cttatgtgca caaaggtgac aatggacgac   1440
ttcctgacag ctcatcatga gatggggcat atccagtatg atatggcata tgctgcacaa   1500
ccttttctgc taagaaatgg agctaatgaa ggattccatg aagctgttgg ggaaatcatg   1560
tcactttctg cagccacacc taagcattta aaatccattg gtcttctgtc acccgatttt   1620
caagaagaca atgaaacaga aataaacttc ctgctcaaac aagcactcac gattgttggg   1680
actctgccat ttacttacat gttagagaag tggaggtgga tggtctttaa aggggaaatt   1740
cccaaagacc agtggatgaa aaagtggtgg gagatgaagc gagagatagt tggggtggtg   1800
gaacctgtgc cccatgatga aacatactgt gaccccgcat ctctgttcca tgtttctaat   1860
gattactcat tcattcgata ttacacaagg accctttacc aattccagtt tcaagaagca   1920
ctttgtcaag cagctaaaca tgaaggccct ctgcacaaat gtgacatctc aaactctaca   1980
gaagctggac agaaactgtt caatatgctg aggcttggaa aatcagaacc ctggacccta   2040
gcattggaaa atgttgtagg agcaaagaac atgaatgtaa ggccactgct caactacttt   2100
gagcccttat ttacctggct gaaagaccag aacaagaatt cttttgtggg atggagtacc   2160
gactggagtc catatgcaga ccaaagcatc aaagtgagga taagcctaaa atcagctctt   2220
ggagataaag catatgaatg gaacgacaat gaaatgtacc tgttccgatc atctgttgca   2280
tatgctatga ggcagtactt tttaaaagta aaaaatcaga tgattctttt tggggaggag   2340
gatgtgcgag tggctaattt gaaaccaaga atctccttta atttctttgt cactgcacct   2400
aaaaatgtgt ctgatatcat tcctagaact gaagttgaaa aggccatcag gatgtcccgg   2460
agccgtatca atgatgcttt ccgtctgaat gacaacagcc tagagtttct ggggatacag   2520
ccaacacttg gacctcctaa ccagccccct gtttccatat ggctgattgt tttggagtt    2580 gtgatgggag tgatagtggt tggcattgtc atcctgatct tcactgggat cagagatcgg   2640
aagaagaaaa ataaagcaag aagtggagaa aatccttatg cctccatcga tattagcaaa   2700
ggagaaaata atccaggatt ccaaaacact gatgatgttc agacctcctt ttag         2754
```

<210> SEQ ID NO 24
<211> LENGTH: 2760
<212> TYPE: DNA
<213> ORGANISM: Artificial Sequence
<220> FEATURE:
<223> OTHER INFORMATION: Codon-optimized CTB-ACE2

<400> SEQUENCE: 24

```
atgacacctc aaaatattac tgatttgtgt gcagaatacc acaacacaca aatacatacg     60
ctaaatgata agatattttc gtatacagaa tctctagctg gaaaaagaga gatggctatc    120
attactttta agaatggtgc aacttttcaa gtagaagtac caggtagtca acatatagat    180
tcacaaaaaa aagcaattga aaggatgaag gataccctga ggattgcata tcttactgaa    240
gctaaagtcg aaaagttatg tgtatggaat aataaaacgc ctcatgcgat tgccgcaatt    300
```

```
agtatggcaa atggtcctgg accacgtcgt aaacgctctg ttatgtctag ttccagctgg      360
ttattgctat ctcttgtagc tgttactgct gcacaatcta ccattgaaga gcaggctaaa      420
acattcctag ataagttcaa ccacgaagca gaggatttat tctaccaatc tagtctagca      480
tcttggaact acaacaccaa cattactgaa gaaaatgttc aaaatatgaa caatgctggt      540
gataaatggt ctgctttcct taaagaacaa tctactttag ctcaaatgta tccattacaa      600
gagattcaaa atttaactgt taaattgcaa ttacaagcac ttcaacagaa tggttctagt      660
gtattaagcg aagataaatc taaacgttta aacacaattc taaacactat gtctaccata      720
tattctactg gtaaagtatg taacccagat aaccctcaag aatgtttatt gttagaacct      780
ggattgaacg agataatggc taactctctt gattacaacg aacgtctatg ggcttgggag      840
tcttggcgca gcgaagttgg caaacaatta cgtcctctat atgaagagta tgttgtacta      900
aaaaatgaaa tggctcgtgc taaccattat gaagactacg gtgattattg gcgtggtgat      960
tacgaggtaa acggagttga tggttacgat tatagtcgtg gtcagctaat tgaagatgtt     1020
gaacacactt tcgaagagat caaacctttg tacgaacatc tacatgctta tgtacgtgct     1080
aaactaatga atgcttatcc ttcttacatt agtcctattg gttgtcttcc agctcatcta     1140 tgggcgata tgtgggtcg tttctggact aacctatact ctctaaccgt acctttcgga      1200
caaaaaccta atattgatgt tactgatgct atggtagatc aagcttggga tgctcaacgt     1260
atcttcaaag aagctgagaa attttttcgta tctgtaggtt tacctaacat gactcaaggt     1320
ttttgggaaa attctatgct taccgatcca ggtaacgttc aaaaagctgt atgtcatcct     1380
accgcttggg atttgggcaa aggtgatttc cgcattctaa tgtgtactaa agtaactatg     1440
gatgacttct taacagctca ccatgaaatg ggtcacatcc aatatgatat ggcttatgct     1500
gcacaacctt tcctattgcg taatggtgct aatgaaggtt ttcatgaagc tgttggagaa     1560
attatgtctt tatctgctgc aactcctaaa catctaaaat ccattggatt attgagccct     1620
gattttcaag aagataacga gaccgaaatt aacttcttgc ttaaacaagc tctaactatc     1680
gttggaactt taccttcac ttatatgttg gaaaaatggc gttggatggt tttcaaaggt      1740
gaaattccta agaccaatg gatgaaaaag tggtgggaaa tgaagcgtga aattgttggt      1800
gtagttgagc cagtaccaca tgatgaaacc tactgcgatc ctgcttcttt attccacgtt     1860
agtaacgatt attcttttat ccgttattac actcgtactc tataccaatt tcaattccaa     1920
gaagctctat gtcaagcagc taaacacgaa ggccctttac acaaatgtga tatttctaat     1980
tctactgagg ctggtcaaaa acttttcaac atgctacgtt tgggtaaatc tgaaccttgg     2040
actttagctt tagaaaacgt tgtaggagct aaaaatatga acgtacgccc tttactaaat     2100
tacttcgaac ctttattcac ttggttaaaa gatcagaaca aaaattcttt cgttggttgg     2160
tccaccgatt ggagccctta tgctgatcaa tctattaaag tacgtatcag tctaaaaagc     2220
gctttaggtg ataaggctta tgagtggaac gataacgaaa tgtacctatt ccgatcagt      2280 gtagcttacg ctatgcgtca gtacttctta aaagttaaaa accaaatgat tttattcggt     2340
gaagaagatg ttcgtgttgc taatcttaaa ccacgtattt ctttcaattt tttcgtaacc     2400
gctccaaaaa acgtttctga cataattcct cgtacagaag tagaaaaagc aatcagaatg     2460
agtcgctccc gaattaatga tgctttcaga ctaaacgata ttctcttga gttcttgggt      2520 attcaaccta ctctaggccc tccaaatcaa ccacctgtat ctatttggtt gatcgttttt     2580
ggtgttgtaa tgggtgttat tgtagtagga attgttatct taattttcac tggtattcga     2640
gatcgtaaaa agaaaaataa ggcacgttct ggtgaaaacc catacgcttc catagatatc     2700
```

```
agtaaaggtg aaaacaatcc tggtttccaa acactgatg acgtacagac ttctttctaa    2760
```

<210> SEQ ID NO 25
<211> LENGTH: 2418
<212> TYPE: DNA
<213> ORGANISM: Artificial Sequence
<220> FEATURE:
<223> OTHER INFORMATION: CTB-ACE2 Native construct

<400> SEQUENCE: 25

```
atgtcaagct cttcctggct ccttctcagc cttgttgctg taactgctgc tcagtccacc      60
attgaggaac aggccaagac attttttggac aagtttaacc acgaagccga agacctgttc    120
tatcaaagtt cacttgcttc ttggaattat aacaccaata ttactgaaga aatgtccaa     180
aacatgaata atgctgggga caaatggtct gccttttttaa aggaacagtc cacacttgcc    240
caaatgtatc cactacaaga aattcagaat ctcacagtca agcttcagct gcaggctctt    300
cagcaaaatg gtcttcagt gctctcagaa gacaagagca acggttgaa cacaattcta     360
aatacaatga gcaccatcta cagtactgga aaagtttgta acccagataa tccacaagaa    420
tgcttattac ttgaaccagg tttgaatgaa ataatggcaa acagtttaga ctacaatgag    480
aggctctggg cttgggaaag ctggagatct gaggtcggca agcagctgag gccattatat    540
gaagagtatg tggtcttgaa aaatgagatg gcaagagcaa atcattatga ggactatggg    600
gattattgga gaggagacta tgaagtaaat ggggtagatg gctatgacta cagccgcggc    660
cagttgattg aagatgtgga acataccttt gaagagatta accattata tgaacatctt    720
catgcctatg tgagggcaaa gttgatgaat gcctatcctt cctatatcag tccaattgga    780
tgcctccctg ctcatttgct tggtgatatg tggggtagat tttggacaaa tctgtactct    840
ttgacagttc cctttggaca gaaaccaaac atagatgtta ctgatgcaat ggtggaccag    900
gcctgggatg cacagagaat attcaaggag gccgagaagt tctttgtatc tgttggtctt    960
cctaatatga ctcaaggatt ctgggaaaat tccatgctaa cggacccagg aaatgttcag    1020
aaagcagtct gccatcccac agcttgggac ctggggaagg gcgacttcag gatccttatg    1080
tgcacaaagg tgacaatgga cgacttcctg acagctcatc atgagatggg gcatatccag    1140
tatgatatgg catatgctgc acaacctttt ctgctaagaa atggagctaa tgaaggattc    1200
catgaagctg ttgggaaat catgtcactt tctgcagcca cacctaagca tttaaaatcc    1260
attggtcttc tgtcacccga tttttcaagaa gacaatgaaa cagaaataaa cttcctgctc    1320
aaacaagcac tcacgattgt tgggactctg ccatttactt acatgttaga gaagtggagg    1380
tggatggtct ttaaagggga aattcccaaa gaccagtgga tgaaaaagtg gtgggagatg    1440
aagcgagaga tagttggggt ggtggaacct gtgccccatg atgaaacata ctgtgacccc    1500
gcatctctgt ccatgttttc taatgattac tcattcattc gatattacac aaggaccctt    1560
taccaattcc agtttcaaga agcactttgt caagcagcta acatgaagg ccctctgcac    1620
aaatgtgaca tctcaaactc tacagaagct ggacagaaac tgttcaatat gctgaggctt    1680
ggaaaatcag aaccctggac cctagcattg gaaaatgttg taggagcaaa gaacatgaat    1740
gtaaggccac tgctcaacta ctttgagccc ttatttaccct ggctgaaaga ccagaacaag    1800
aattcttttg tgggatggag taccgactgg agtccatatg cagaccaaag catcaaagtg    1860
aggataagcc taaaatcagc tcttggagat aaagcatatg aatggaacga caatgaaatg    1920
tacctgttcc gatcatctgt tgcatatgct atgaggcagt actttttaaa agtaaaaat    1980
```

```
cagatgattc tttttgggga ggaggatgtg cgagtggcta atttgaaacc aagaatctcc   2040
tttaatttct ttgtcactgc acctaaaaat gtgtctgata tcattcctag aactgaagtt   2100
gaaaaggcca tcaggatgtc ccggagccgt atcaatgatg ctttccgtct gaatgacaac   2160
agcctagagt ttctggggat acagccaaca cttggacctc ctaaccagcc ccctgtttcc   2220
atatggctga ttgtttttgg agttgtgatg ggagtgatag tggttggcat tgtcatcctg   2280
atcttcactg ggatcagaga tcggaagaag aaaaataaag caagaagtgg agaaaatcct   2340
tatgcctcca tcgatattag caaaggagaa aataatccag gattccaaaa cactgatgat   2400
gttcagacct ccttttag                                                 2418

<210> SEQ ID NO 26
<211> LENGTH: 2418
<212> TYPE: DNA
<213> ORGANISM: Artificial Sequence
<220> FEATURE:
<223> OTHER INFORMATION: CTB-ACE2 Codon Optimized construct

<400> SEQUENCE: 26
atgtctagtt ccagctggtt attgctatct cttgtagctg ttactgctgc acaatctacc     60
attgaagagc aggctaaaac attcctagat aagttcaacc acgaagcaga ggatttattc    120
taccaatcta gtctagcatc ttggaactac aacaccaaca ttactgaaga aaatgttcaa    180
aatatgaaca atgctggtga taaatggtct gctttcctta aagaacaatc tactttagct    240
caaatgtatc cattacaaga gattcaaaat ttaactgtta aattgcaatt acaagcactt    300
caacagaatg gttctagtgt attaagcgaa gataaatcta aacgtttaaa cacaattcta    360
aacactatgt ctaccatata ttctactggt aaagtatgta acccagataa ccctcaagaa    420
tgtttattgt tagaacctgg attgaacgag ataatggcta actctcttga ttacaacgaa    480
cgtctatggg cttgggagtc ttggcgcagc gaagttggca aacaattacg tcctctatat    540
gaagagtatg ttgtactaaa aaatgaaatg gctcgtgcta accattatga agactacggt    600
gattattggc gtggtgatta cgaggtaaac ggagttgatg gttacgatta tagtcgtggt    660
cagctaattg aagatgttga acacactttc gaagagatca aacctttgta cgaacatcta    720
catgcttatg tacgtgctaa actaatgaat gcttatcctt cttacattag tcctattggt    780
tgtcttccag ctcatctatt gggcgatatg tggggtcgtt tctggactaa cctatactct    840
ctaaccgtac ctttcggaca aaaacctaat attgatgtta ctgatgctat ggtagatcaa    900
gcttgggatg ctcaacgtat cttcaaagaa gctgagaaat tttcgtatc tgtaggttta     960 cctaacatga ctcaaggttt ttgggaaaat tctatgctta ccgatccagg taacgttcaa   1020
aaagctgtat gtcatcctac cgcttgggat ttgggcaaag gtgatttccg cattctaatg   1080
tgtactaaag taactatgga tgacttctta acagctcacc atgaaatggg tcacatccaa   1140
tatgatatgg cttatgctgc acaacctttc ctattgcgta atggtgctaa tgaaggtttt   1200
catgaagctg ttggagaaat tatgtcttta tctgctgcaa ctcctaaaca tctaaaatcc   1260
attggattat tgagccctga ttttcaagaa gataacgaga ccgaaattaa cttcttgctt   1320
aaacaagctc taactatcgt tggaacttta cctttcactt atatgttgga aaaatggcgt   1380
tggatggttt tcaaaggtga aattcctaaa gaccaatgga tgaaaaagtg gtgggaaatg   1440
aagcgtgaaa ttgttggtgt agttgagcca gtaccacatg atgaaaccta ctgcgatcct   1500
gcttctttat tccacgttag taacgattat tcttttatcc gttattacac tcgtactcta   1560
taccaatttc aattccaaga agctctatgt caagcagcta aacacgaagg ccctttacac   1620
```

```
aaatgtgata tttctaattc tactgaggct ggtcaaaaac ttttcaacat gctacgtttg   1680
ggtaaatctg aaccttggac tttagcttta gaaaacgttg taggagctaa aaatatgaac   1740 gtacgcccctt tactaaatta cttcgaacct ttattcactt ggttaaaaga tcagaacaaa   1800
aattctttcg ttggttggtc caccgattgg agcccttatg ctgatcaatc tattaaagta   1860
cgtatcagtc taaaaagcgc tttaggtgat aaggcttatg agtggaacga taacgaaatg   1920
tacctattcc gatctagtgt agcttacgct atgcgtcagt acttcttaaa agttaaaaac   1980
caaatgattt tattcggtga agaagatgtt cgtgttgcta atcttaaacc acgtatttct   2040
ttcaattttt tcgtaaccgc tccaaaaaac gtttctgaca taattcctcg tacagaagta   2100
gaaaaagcaa tcagaatgag tcgctcccga attaatgatg ctttcagact aaacgataat   2160
tctcttgagt tcttgggtat tcaacctact ctaggccctc caaatcaacc acctgtatct   2220
atttggttga tcgtttttgg tgttgtaatg ggtgttattg tagtaggaat tgttatctta   2280
attttcactg gtattcgaga tcgtaaaaag aaaaataagg cacgttctgg tgaaaaccca   2340
tacgcttcca tagatatcag taaaggtgaa aacaatcctg gtttccaaaa cactgatgac   2400
gtacagactt ctttctaa                                                  2418
```

```
<210> SEQ ID NO 27
<211> LENGTH: 2418
<212> TYPE: DNA
<213> ORGANISM: Artificial Sequence
<220> FEATURE:
<223> OTHER INFORMATION: CTB-ACE2 Codon Optimized construct

<400> SEQUENCE: 27
atgtcatctt cttcttggtt attattatct ttagttgctg taactgctgc tcaatctact     60
attgaagaac aagctaaaac atttttagat aaatttaatc atgaagctga agatttattt    120
tatcaaagtt cattagcttc ttggaattat aatactaata ttactgaaga aaatgttcaa    180
aatatgaata atgctggtga taaatggtct gctttttttaa aagaacaatc tacattagct   240
caaatgtatc cattacaaga aattcaaaat ttaacagtta aattacaatt acaagcttta    300
caacaaaatg gttcttcagt tttatcagaa gataaatcta aaagattaaa tacaatttta    360
aatacaatgt ctactattta tagtactgga aaagtttgta atccagataa tccacaagaa    420
tgtttattat tagaaccagg tttaaatgaa ataatggcta atagtttaga ttataatgaa    480
agattatggg cttgggaatc ttggagatct gaagttggta aacaattaag accattatat    540
gaagaatatg ttgttttaaa aaatgaaatg gctagagcta atcattatga agattatggt    600
gattattgga gaggagatta tgaagtaaat ggtgtagatg gttatgatta ttctaggggt    660
caattaattg aagatgttga acatactttt gaagaaatta aaccattata tgaacattta    720
catgcttatg ttagagctaa attaatgaat gcttatcctt cttatattag tccaattgga    780
tgtttacctg ctcatttatt aggtgatatg tggggtagat tttggacaaa tttatattct    840
ttaacagttc cttttggaca aaaaccaaat atagatgtta ctgatgctat ggttgatcaa    900
gcttgggatg ctcaaagaat atttaaagaa gctgaaaaat tttttgtatc tgttggttta    960
cctaatatga ctcaaggatt ttgggaaaat tctatgttaa ctgatccagg aaatgttcaa   1020
aaagctgttt gtcatcctac agcttgggat ttaggtaaag gtgattttag aattttaatg   1080
tgtacaaaag ttacaatgga tgattttttta acagctcatc atgaaatggg tcatattcaa  1140
tatgatatgg cttatgctgc tcaacctttt ttattaagaa atggagctaa tgaaggattt   1200
```

-continued

```
catgaagctg ttggtgaaat tatgtcatta tctgctgcta cacctaaaca tttaaaatct   1260
attggtttat tatcacctga ttttcaagaa gataatgaaa cagaaataaa ttttttatta   1320
aaacaagctt taactattgt tggtacttta ccatttactt atatgttaga aaaatggaga   1380
tggatggttt ttaaaggtga aattcctaaa gatcaatgga tgaaaaaatg gtgggaaatg   1440
aaacgagaaa tagttggtgt tgttgaacct gttcctcatg atgaaacata ttgtgatcct   1500
gcttctttat ttcatgtttc taatgattat tcatttattc gatattatac aagaacttta   1560
tatcaatttc aatttcaaga agctttatgt caagctgcta aacatgaagg tcctttacat   1620
aaatgtgata tttcaaattc tacagaagct ggacaaaaat tatttaatat gttaagatta   1680
ggaaaatcag aaccttggac tttagcttta gaaaatgttg taggagctaa aaatatgaat   1740
gtaagaccat tattaaatta ttttgaacct ttatttactt ggttaaaaga tcaaaataaa   1800
aattcttttg ttggatggag tactgattgg agtccttatg ctgatcaatc tattaaagtt   1860
agaatatctt taaaatcagc tttaggagat aaagcttatg aatggaatga taatgaaatg   1920
tatttatttc gatcatctgt tgcttatgct atgagacaat attttttaaa agtaaaaaat   1980
caaatgattt tatttggtga agaagatgtt cgagttgcta atttaaaacc aagaatttct   2040
tttaattttt ttgttactgc tcctaaaaat gtttctgata ttattcctag aactgaagtt   2100
gaaaaagcta ttagaatgtc taggtctcgt attaatgatg cttttcgttt aaatgataat   2160
tctttagaat tttaggtat acaaccaaca ttaggacctc ctaatcaacc tcctgtttct   2220
atatggttaa ttgtttttgg agttgttatg ggagttatag ttgttggtat tgttatttta   2280
atttttactg gtattagaga tagaaaaaaa aaaaataaag ctagaagtgg agaaaatcct   2340
tatgcttcta ttgatatttc taaaggagaa aataatccag gatttcaaaa tactgatgat   2400
gttcaaactt ctttttaa                                                 2418
```

<210> SEQ ID NO 28
<211> LENGTH: 805
<212> TYPE: PRT
<213> ORGANISM: Artificial Sequence
<220> FEATURE:
<223> OTHER INFORMATION: CTB-ACE2

<400> SEQUENCE: 28

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140
```

```
Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
```

-continued

```
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 29
<211> LENGTH: 7
<212> TYPE: PRT
<213> ORGANISM: Homo sapiens

<400> SEQUENCE: 29

Asp Arg Val Tyr Ile His Pro
1               5
```

ORAL DELIVERY OF ANGIOTENSIN CONVERTING ENZYME 2 (ACE2) OR ANGIOTENSIN-(1-7)-BIOENCAPSULATED IN PLANT CELLS ATTENUATES PULMONARY HYPERTENSIONS, CARDIAC DYSFUNCTION AND DEVELOPMENT OF AUTOIMMUNE AND EXPERIMENTALLY INDUCED OCULAR DISORDERS

CROSS-REFERENCE TO RELATED APPLICATIONS

This application is a divisional of U.S. patent application Ser. No. 15/030,377, filed Apr. 18, 2016, which is a continuation-in-part of International Application No. PCT/US2014/061428, filed Oct. 20, 2014, which in turn claims benefit of U.S. Provisional Application Nos. 61/892,717, 61/943,754 and 61/952,078 filed Oct. 18, 2013, Feb. 24, 2014 and Mar. 12, 2014, respectively. Each of these applications is incorporated herein by reference as though set forth in full.

STATEMENT OF FEDERAL FUNDING

This invention was made with government support under grant nos. HL099980, HL102033, HL106687, HL109442, EY021752 and EY21721 awarded by the National Institutes of Health. The U.S. Government has certain tights in the invention.

BACKGROUND OF THE INVENTION

Numerous publications and patent documents, including both published applications and issued patents, are cited throughout the specification in order to describe the state of the art to which this invention pertains. Each of these citations is incorporated herein by reference as though set forth in full.

Pulmonary hypertension (PH) is a devastating lung disease characterized by elevated blood pressure in the pulmonary circulation, which eventually leads to right-heart failure and death.[1] Although significant advances have been made in recent years to improve the quality of life of patients with PH; none of the current treatments are successful in reversing PH or decreasing mortality. This has led to the realization that novel mechanism based therapies must be developed to accomplish this goal.[2]

It is well-recognized that activation of the vasodeleterious axis of the renin angiotensin system (RAS), comprising of angiotensin-converting enzyme (ACE), angiotensin II (AngII) and angiotensin type I receptor (AT1R) is involved in the development of PH.[3,4] However, the clinical use of ACE inhibitors or AT1R blockers have yielded mixed results, thereby failing to reach a consensus opinion regarding their use for PH therapy. Nonetheless, the recent discovery of a close homolog of ACE, angiotensin converting enzyme2 (ACE2) has resulted in the re-evaluation of the role of RAS in PH.[5,6] ACE2 is widely expressed in the lungs,[7] predominantly on the pulmonary vascular endothelium, and catalyzes the conversion of AngII to Angiotensin-(1-7) [Ang-(1-7)]. Ang-(1-7) is a vasoactive heptapeptide that mediates its effects by stimulating the Mas receptor.[8] Thus, ACE2-Ang-(1-7)-Mas receptor constitutes the vasoprotective axis of RAS, which counterbalances the deleterious actions of the ACE-AngII-AT1R axis.

Recent reports indicate that decreased tissue and circulating levels of ACE2 are associated with lung diseases in humans.[9,10] On the other hand, restoration of ACE2 through genetic overexpression, administration of recombinant protein or use of pharmacological ACE2 activators resulted in cardiopulmonary protective effects against animal models of pulmonary diseases.[11-15] These findings provided compelling evidence for initiating clinical trials with recombinant ACE2 or Ang-(1-7) in treating pulmonary disorders. Although clinical trials are currently underway (ClinicalTrials.gov; NCT01884051), the cost of manufacturing, protein stability, repetitive intravenous dosing and patient compliance pose major impediments in realizing full therapeutic potential of this therapy.

The renin-angiotensin system (RAS) plays an important role not only in the cardiovascular homeostasis, but also in the pathogenesis of inflammation and autoimmune dysfunction in which Angiotensin II (Ang II) functions as the potent proinflammatory effector via Angiotensin Type 1 receptor (AT1 receptor). Most components of RAS have been identified in every organ including the eye. The tissue-specific RAS is believed to exert diverse physiological effects locally independent of circulating Ang II (Paul et al., (2006) Physiol Rev. 86:747-803). Several studies have shown that ACE2/Ang-(1-7)/Mas axis also influences inflammatory responses and negatively modulates leukocyte migration, cytokine expression and release, and fibrogenic pathways (Qui et al. (2014) Invest., OPthalmol Vis Sci. 55:3809-3818) We have recently shown that increased expression of ACE2 and Ang-(1-7) reduced diabetes-induced retinopathy and inflammation in both mouse and rat models of diabetic retinopathy (Rawas-Qalaji et al., (2012) Curr Eye Res. 37:345-356), activation of endogenous ACE2 activity reduced endotoxin-induced uveitis (Kwon et al., (2013) Adv. Drug Deliv Rev 65:782-799), providing the proof-of-concept that enhancing the protective axis of RAS is a promising therapeutic strategy for ocular inflammatory diseases.

However, the ability to deliver drugs efficiently to the retina or the brain remains a key challenge due to anatomic barriers and physiological clearance mechanisms [13].

SUMMARY OF INVENTION

In accordance with the present invention a composition comprising lyophilized plant material comprising a therapeutic protein produced in chloroplasts which retains biological function in lyophilized form is provided. Surprisingly oral administration of said material to a patient in need thereof is effective to produce a beneficial therapeutic result. In one embodiment of the invention, the plant material comprises leaves obtained from a homoplasmic plant, and the therapeutic protein is a fusion protein comprising angiotensin-converting enzyme 2 (ACE-2), and cholera non toxic B subunit (CTB) and exerts beneficial cardioprotective effects. In another embodiment, the plant material comprises leaves obtained from a homoplasmic plant, and the therapeutic protein is a fusion protein comprising angiotensin-(1-7) (Ang-(1-7)), and cholera non toxic B subunit (CTB), and provides a cardioprotective effect. The plant species for transgenic expression of said therapeutic protein can include, without limitation, lettuce, carrots, cauliflower, cabbage, grass, low-nicotine tobacco, spinach, kale, and cilantro. The fusion proteins described above can contain a hinge peptide and furin cleavage site between said CTB and said ACE-2 or said Ang1(1-7).

In a particularly preferred embodiment, the lyophilized plant material comprises a combination of ACE-2 and angiotensin-(1-7). In another aspect of this embodiment, the ACE2 sequence is codon optimized and is encoded by SEQ ID NO: 24.

In another aspect, a method for the treatment of pulmonary hypertension comprising administration of an effective amount of the compositions described above to a patient in need thereof is the disclosed wherein the composition exerts a cardioprotective effect comprising at least one of improved right heart function, decreased pulmonary vessel wall thickness, and a lack of altered basal system blood pressure, said method optionally comprising assessing said effects after administration of said composition. In certain embodiments, the patient is assessed for cardioprotective effects.

In another aspect of the invention, the compositions described above can be used to advantage to reduce ocular inflammation. Thus, the present invention also provides a method for treating or delaying the onset of uveoretinitis in a subject in need thereof comprising oral administration of a therapeutically effective amount of the compositions described above, wherein the administration is effect to reduce ocular inflammation in said subject, the method optionally comprising assessing said reduction in ocular inflammation in said subject. In certain embodiments, the subject is assessed for a reduction in ocular inflammation.

BRIEF DESCRIPTION OF DRAWINGS

FIGS. 1A-1G. Characterization, concentration and evaluation of pentameric structure of CTB-ACE2 and CTB-Ang-(1-7) expressed in plant chloroplasts. (FIG. 1A) Schematic representation of CTB-ACE2 and CTB-Ang-(1-7) gene cassettes and flanking regions. Southern blot analysis of (FIG. 1B) CTB-ACE2 and (FIG. 1C) CTB-Ang-(1-7) transplastomic lines. HindIII-digested untransformed (UT) and transformed (lane 1, 2, and 3) genomic DNA was probed with $P^{32}$-labeled flanking sequence. Quantification of (FIG. 1D) CTB-ACE2 and (FIG. 1E) CTB-Ang-(1-7) as a percentage of the total leaf proteins (TLP). (FIG. 1F) GM1 binding assay of CTB-ACE2 and CTB-Ang-(1-7). CTB, non-toxic cholera B subunit (1 ng); UT, untransformed wild type; F, fresh; L, lyophilized; BSA, bovine serum albumin (1%, w/v). (FIG. 1G) Western blot analysis of CTB-Ang-(1-7) in non-reducing condition without boiling and DTT. Lanes 1, 2, and 3:10, 15, and 20 ng of CTB; total homogenate of CTB-Ang-(1-7): 0.2, 0.4, 0.8, and 1.6 µg. The pentameric structures for the CTB alone and the fusion protein are indicated by arrow head and arrow, respectively. Data shown are mean±SD of three independent experiments.

(FIG. 2A) Measurement of right ventricular systolic pressure (RVSP) in normal controls and MCT-challenged rats that were either untreated or orally fed with wild type leaf material or gavaged with bioencapsulated ACE2/Ang-(1-7). (FIG. 2B) Right ventricle (RV) hypertrophy, measured as the ratio of RV to left ventricle (LV) plus interventricular septum (S) weights [RV/(LV+S)]. Measurement of (FIG. 2C) right ventricular end-diastolic pressure (RVEDP), (FIG. 2D)+dP/dt, and (FIG. 2E)−dP/dt. Echocardiography data representing (FIG. 2F) ejection fraction (EF), (FIG. 2G) ratio of the right to left end diastolic area, signifying right heart dilation and (FIG. 2H) the blood flow rate in the right ventricular outflow tract (RVOT). Data shown are mean±SEM. ***P<0.001 vs. control rats and #P<0.05 vs. untreated or wild type leaf fed MCT-rats. n=6-8 animals/group.

(FIG. 3A) End Diastolic Area of Left Ventricle (LV EDA), as visualized by echocardiography. LV EDA was significantly reduced in PH animals and the oral feeding of ACE2 or Ang-(1-7) prevented the reduction in the LV EDA. (FIG. 3B) End Diastolic Area of Right Ventricle (RV EDA), as visualized by echocardiography. RV EDA was significantly increased in the PH animals demonstrating the right ventricular dilation. Oral feeding of ACE2 or Ang-(1-7) significantly reduced the RV dilation and improved the cardiac function. (FIG. 3C) Ejection Fraction of Left Ventricle, as visualized by echocardiography. LV EF was slightly reduced in PH animals. Data represents mean±SEM with n=5 animals. (FIG. 2D) Ejection fraction of Right Ventricle, as visualized by echocardiography. RV EF was significantly reduced in the PH animals demonstrating the cardiac dysfunction. Oral feeding of ACE2 or Ang-(1-7) attenuated the MCT induced decrease in RV ejection function. (MCT+ACE2-P and MCT+Ang-(1-7)-P represents the prevention protocol, while MCT+ACE2-R and MCT+Ang-(1-7)-R represents the reversal protocol. MCT+C-500 and MCT+C-250 represent the combination treatment using 500 mg and 250 mg respectively in the reversal protocol.) In, both figures, data represent mean±SEM with n=5 animals *** denoting p<0.001 as compared with normal controls, while # representing p<0.05 Vs untreated and wild type plant material fed MCT animals as assessed by One-Way ANOVA followed by Newman-Keuls test.

(FIG. 5A) Data indicates significant elevation of right ventricular systolic pressure (RVSP) after 2-weeks of MCT administration, signifying induction of PH (n=5 rats per group). Data are expressed as mean±SEM; * p<0.05 versus controls using student t-test. Measurement of (FIG. 5B) right ventricular end-diastolic pressure (RVEDP), (FIG. 5C)+dP/dt, and (FIG. 5D)−dP/dt in in normal controls and MCT-challenged rats that were either untreated or orally fed with wild type leaf material or gavaged with bioencapsulated ACE2/Ang-(1-7). Data are expressed as mean±SEM; ***p<0.001; versus controls and # p<0.05 versus MCT group. n=5 animals per experimental group.

FIGS. 6A-6C. Oral feeding of bioencapsulated ACE2 or Ang-(1-7) exerts anti-fibrotic and anti-remodeling effects in the prevention protocol. (FIG. 6A) Interstitial collagen deposition in the right ventricle. (FIG. 6B) Staining for α-smooth muscle actin to quantify medial wall thickness of the pulmonary arteries measuring less than 50 µm. Scale bar denotes 10 µm (FIG. 6C) ACE2 activity was measured in rat sera (10 µl) collected from different experimental groups AFU: Arbitrary fluorescence units. Data represents mean±SEM with * denoting p<0.05 Vs other groups, ** denoting p<0.01 as compared with controls, while # representing p<0.05 vs. untreated and wild type plant material fed MCT-rats as assessed by One-Way ANOVA followed by Newman-Keuls test.

FIGS. 7A-7G. Oral treatment with ACE2 or Ang-(1-7) arrests disease progression and attenuates cardiopulmonary remodeling. (FIG. 7A) Individual values of the right ventricle systolic pressure (RVSP) from different experimental groups of the reversal protocol. (FIG. 7B) RV/(LV+S) values from individual animals, denoting right heart hypertrophy. Echocardiography data representing (FIG. 7C) ratio of the right to left ventricle end diastolic area, (FIG. 7D) ejection fraction (EF), and (FIG. 7E) the blood flow rate in the right ventricular outflow tract (RVOT) of the different experimental groups. (FIG. 7F) Representative photographs and quantification of interstitial fibrosis (FIG. 7G) Measurement of vessel wall thickness following α-smooth muscle actin staining of the pulmonary arteries (<50 µm). Scale bar denotes 10 µm. Data shown are mean±SEM.  P<0.01, *P<0.001 vs. control rats and #P<0.05 vs. untreated or wild type leaf fed MCT-rats. n=6-8 animals/group.

(FIG. 8A) Measurement of right ventricular systolic pressure (RVSP) in MCT rats treated with a combination of either 500 mg or 250 mg each of ACE2 and Ang-(1-7). (FIG. 8B) Data representing right ventricular hypertrophy as a ratio of RV/(LV+S). Measurement of (FIG. 8C) right ventricular end-diastolic pressure (RVEDP), (FIG. 8D)+dP/dt, and (FIG. 8E)−dP/dt from the combination study. Echocardiography data representing (FIG. 8F) ejection fraction (EF), (FIG. 8G) ratio of the right to left end diastolic area and (FIG. 8H) the blood flow rate in the right ventricular outflow tract (RVOT). Data shown are mean±SEM. ***P<0.001 vs. control rats and #P<0.05 vs. untreated or wild type leaf fed MCT-rats. n=6-8 animals/group.

FIGS. 9A-9B. Combination of ACE2 and Ang-(1-7) decreases ventricular fibrosis and attenuates pulmonary vascular remodeling. (FIG. 9A) Representative photographs of collagen staining and quantitative analysis of right ventricular fibrosis following 2-week treatment with combination therapy. (FIG. 9B) Measurement of vessel wall thickness of the pulmonary arteries (<50 µm). Scale bar denotes 10 µm. Data are expressed as mean±SEM; **p<0.01; versus controls and # p<0.05 versus untreated and wild type plant material fed MCT-rats. n=5-7 animals per experimental group.

FIGS. 10A-10J. Effects of ACE2 or Ang-(1-7) treatment on the lung renin-angiotensin system (RAS), pro-inflammatory cytokines and autophagy (prevention protocol). Relative change in lung mRNA levels of (FIG. 10A) Angiotensin-converting enzyme (ACE), (FIG. 10B) angiotensin-converting enzyme 2 (ACE2), (FIG. 10C) ACE/ACE2 ratio, (FIG. 10D) AT1R, (FIG. 10E) AT2R and (FIG. 10F) AT1R/AT2R receptor. Relative mRNA levels of lung pro-inflammatory cytokines, (FIG. 10G) tumor necrosis factor (TNF)-α, (FIG. 10H) transforming growth factor (TGF)-β and (FIG. 10I) toll-like receptor-4 (TLR-4) from the MCT study. Autophagy marker, LC3-II is increased in the lungs of MCT-exposed animals. (FIG. 10J) Immunoblot and densitometry analysis of the lung LC3I/II protein expression. Data are expressed as mean±SEM. * P<0.05,  P<0.01, and * P<0.001 versus control rats. # P<0.05 versus MCT group.

FIGS. 11A-11J. Effects of Monotherapy as well as the combination therapy on the lung RAS components, pro-inflammatory cytokines and autophagy in the reversal protocol. Data represent relative changes in lung mRNA levels of (FIG. 11A) Angiotensin-converting enzyme (ACE), (FIG. 11B) angiotensin-converting enzyme 2 (ACE2), (FIG. 11C) ACE/ACE2 ratio, (FIG. 11D) Angiotensin type 1 receptor (AT1R), (FIG. 11E) Angiotensin type 2 receptor (AT2R) and (FIG. 11F) AT1R/AT2R ratio. Relative mRNA levels of lung pro-inflammatory cytokines, (FIG. 11G) tumor necrosis factor (TNF)-α, (FIG. 11H) transforming growth factor (TGF)-β and (FIG. 11I) toll-like receptor-4 (TLR-4) from the same study. (FIG. 11J) Immunoblot and densitometry quantification showing lung LC3I/II protein expression. Data are expressed as mean±SEM. * p<0.05 and ** p<0.01 versus control rats, while # P<0.05 versus MCT group.

FIG. 12A. Western blot analysis to investigate the proper folding and assembly of CTB-Ang-(1-7) expressed in chloroplasts. Four micrograms of total leaf protein were loaded for each lane with (+) or without (−) treatment of denaturing agents. CTB, purified non-toxic cholera B subunit (10 ng); UT, untransformed wild type; DTT, 100 mM; boiling, incubation of samples in boiling water for 3 min; H, homogenate total leaf protein; S, supernatant fraction after centrifugation of the total leaf protein; Arrows and numbers, locations of monomer and oligomers of CTB-Ang-(1-7); P, pentamer-pentamer complexes. FIG. 12B. Western blot analysis for the comparison of the level of CTB-Ang-(1-7) in lyophilized (L) and fresh (F) leaves. Equal amount of lyophilized and fresh leaf material (10 mg) was extracted in same volume (300 µl) of extraction buffer. 1× represents 1 µl of homogenate protein resuspended in extraction buffer. The samples were boiled in DTT prior to loading on SDS acrylamide gel. Purified CTB standard protein was loaded as indicated for densitometric analysis. FIG. 12C. and FIG. 12D. Comparison of the level of CTB-Ang-(1-7) and -ACE2 in lyophilized (L) and fresh (F) leaves. Data are means±SD of three independent experiments. FIG. 12E. GM1 binding assay of CTB-ACE2 and -Ang-(1-7). Extracted total protein samples were serially diluted up to 10 pg/ul, which means 11 on the Y axis, and used for GM1 binding assay. The binding affinity was read at 450 nm then an absorbance of ≥0.1 after background signal substraction was determined as positive. Two and three different batches were examined for fresh and lyophilized leaf materials, respectively, and indicated as black diamond. CTB, purified non-toxic cholera B subunit (black circle); UT, untransformed wild type (black triangle); F, fresh; L, lyophilized; 12 and 15, 12- and 15-month storage at room temperature. *p<0.001 (versus fresh); #p<0.001 (versus WT).

FIG. 13A. Assay buffer containing the substrate was also used as a negative control. FIG. 13B. Increased ACE2 in both serum and retina in mice fed with CTB-ACE2 leaf material detected by Western blotting using an anti-ACE2 polyclonal antibody. FIG. 13C. ACE2 activities in serum and retina from mice fed with either fresh (F, 500 mg/mouse), or lyophilized (L, 50 mg/mouse) CTB-ACE2 leaf materials, compared to mice fed with wild type (WT) leaf materials; (n=5 per group). The experiment was repeated at least twice with similar results.

* p<0.05 (versus WT leaf). FIG. 13D. A graph showing results from an ELISA assay demonstrating the presence of Ang-(1-7) in plasma and retina after oral administration.

FIG. 14A. Representative photographs of the iris ciliary body, anterior chamber and posterior chamber. Original magnifications 20×. Bar=50 µm. FIG. 14B. Histopathologic score evaluation. Inflammatory cells per section in the iris ciliary body, anterior chamber and posterior chamber were counted from H&E stained paraffin sections from eyes at 24 h after EIU induction. Values on y-axis represent no. of infiltrating inflammatory cells/section. Results are given as mean+SD; (n=6 per group); *P<0.05 (versus WT+LPS group). FIG. 14C. Histological evaluation of EIU mice. The mice were orally administered with different doses of lyophilized plant cells expressing CTB-ACE2 for four days before LPS (25 ng/eye) injection. Eyes were enucleated 24 hr after LPS injection, fixed and processed for sections and stained with H&E and Histopathologic score was evaluated by at least two individuals. Inflammatory cells per section in the iris ciliary body, anterior chamber and posterior chamber were counted from H&E stained sections from eyes at 24 h after EIU induction. Values on y-axis represent no. of infiltrating inflammatory cells/section. Results are given as mean+SD; (n=6 per group); *P<0.05 (versus WT+LPS group).

FIGS. 16A-16G. Clinical evaluation of EAU from fundoscopic photographs. EAU was induced in B10.RIII mice by immunization with IRBP in CFA. The fundoscopic images were obtained on day 14 after immunization. Representative fundus image from WT leaf fed mice (FIG. 16a, FIG. 16b); CTB-ACE2 expressed leaf fed mice (FIG. 16c, FIG. 16d); and CTB-Ang-(1-7) expressed leaf fed mice (FIG. 16e, FIG. 16f). FIG. 16G. Clinical EAU scores. Clinical EAU score was evaluated on a scale of 0-4. Values on y-axis represent the average of clinical scores given on fundus images. Results are given as mean+SD; (n=5 per group); *P<0.05 (versus WT fed group).

FIG. 17A. Representative fundus projection (left panel) and B-scan (right panel) images from WT leaf fed mice; CTB-ACE2 expressed leaf fed mice; and CTB-Ang-(1-7) expressed leaf fed mice. FIG. 17B. Retinal thickness measured from OCT images. Values on y-axis represent the average of retinal thickness calculated manually from B-scan OCT images. Results are given as mean+SD; (n=5 per group); *P<0.05 (versus WT fed group).

FIG. 18A. Representative micrographs from animals fed with WT leaf fed mice, CTB-ACE2, and CTB-Ang-(1-7) leaf materials. Images of histological analysis show severe retinal folding, loss of the photoreceptor layer and massive inflammatory cell inflammation in the vitreous, retina and subretinal space in WT leaf fed group; moderate to minimum infiltration, photoreceptor damage, retinal folding was observed in CTB-ACE2 expressed leaf fed group; a minor infiltration of cells and retinal folding was observed in the CTB-Ang-(1-7) leaf fed group. FIG. 18B. Histopathology scores. CTB-ACE2 and CTB-Ang-(1-7) leaf fed groups showed a reduced EAU histological grade compared to controls fed with WT leaf. FIG. 18C. Evaluation of infiltrating inflammatory cells in the posterior chamber. Inflammatory cells/section in the posterior chamber were counted on 14th day after EAU induction. Values on y-axis represent no. of infiltrating inflammatory cells/section. Results are given as mean+SD; (n=5 per group); *P<0.05 (versus WT leaf fed group).

FIG. 19A. Clinical EAU scores. Clinical EAU score was evaluated on a scale of 0-4. FIG. 19B. Retinal thickness measured from OCT images. Horizontal and cross sectional OCT images were obtained on day 14 after immunization. The retinal thickness was measured and averaged from five different frames of horizontal OCT scan images of single eye. FIG. 19C. Histopathology scores. CTB-Ang-(1-7) leaf fed groups showed a reduced EAU histological grade compared to controls fed with WT leaf. Values on y-axis represent the average of clinical scores given on fundus images. Results are given as mean+SD; (n=6 per group); *p<0.05 (versus WT fed group).

Figure 20A:
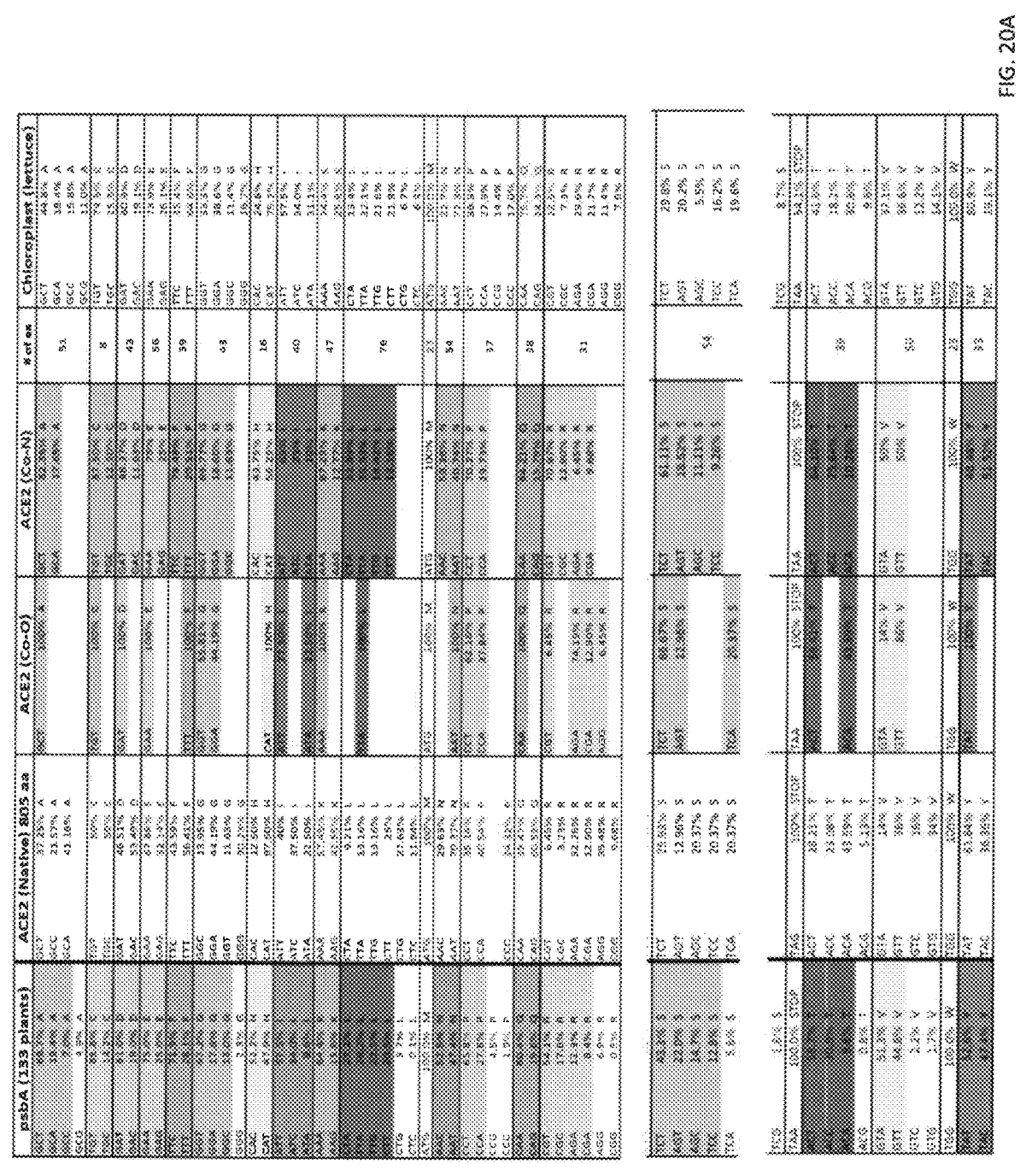
Figure 20B:
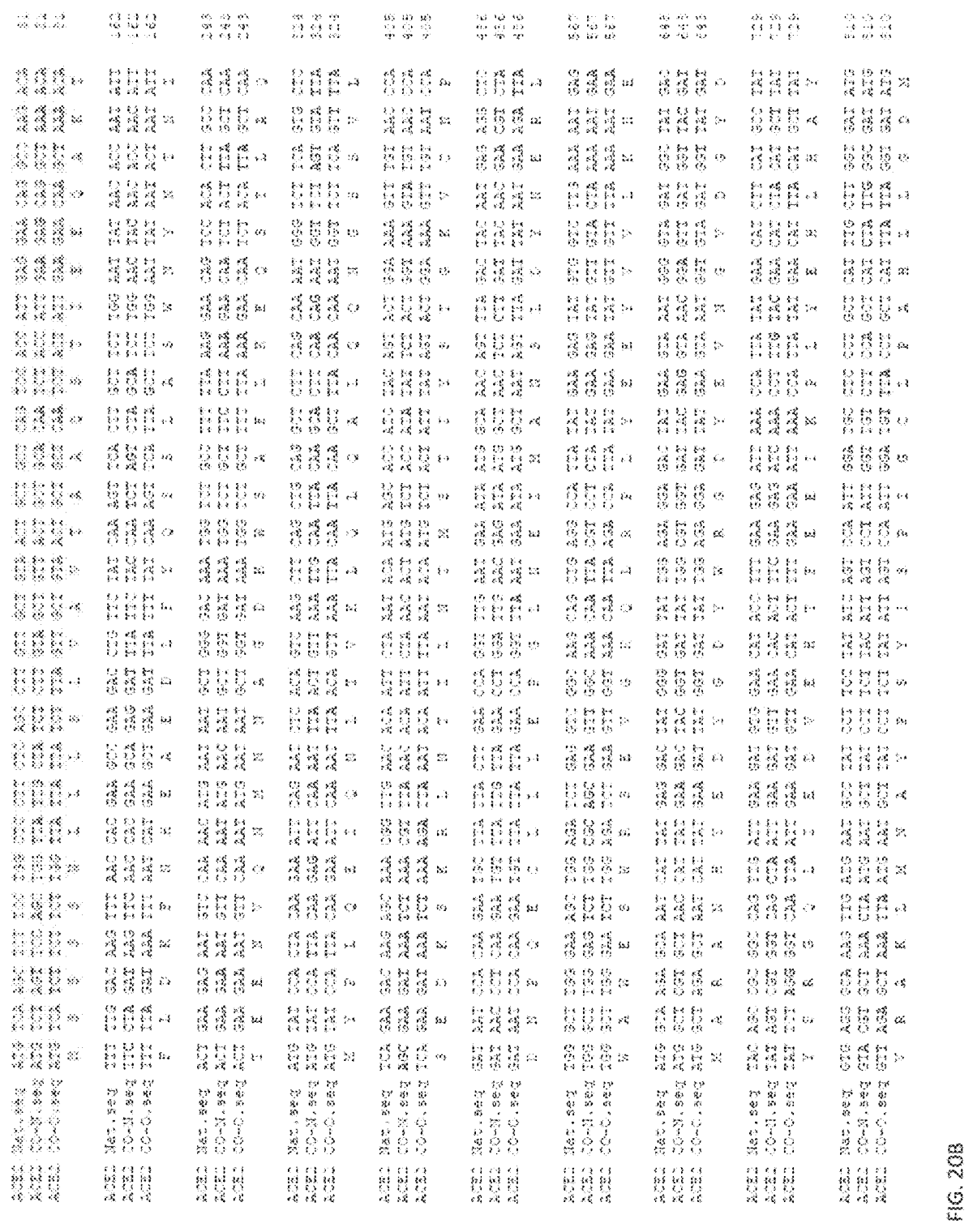
Figure 20C:
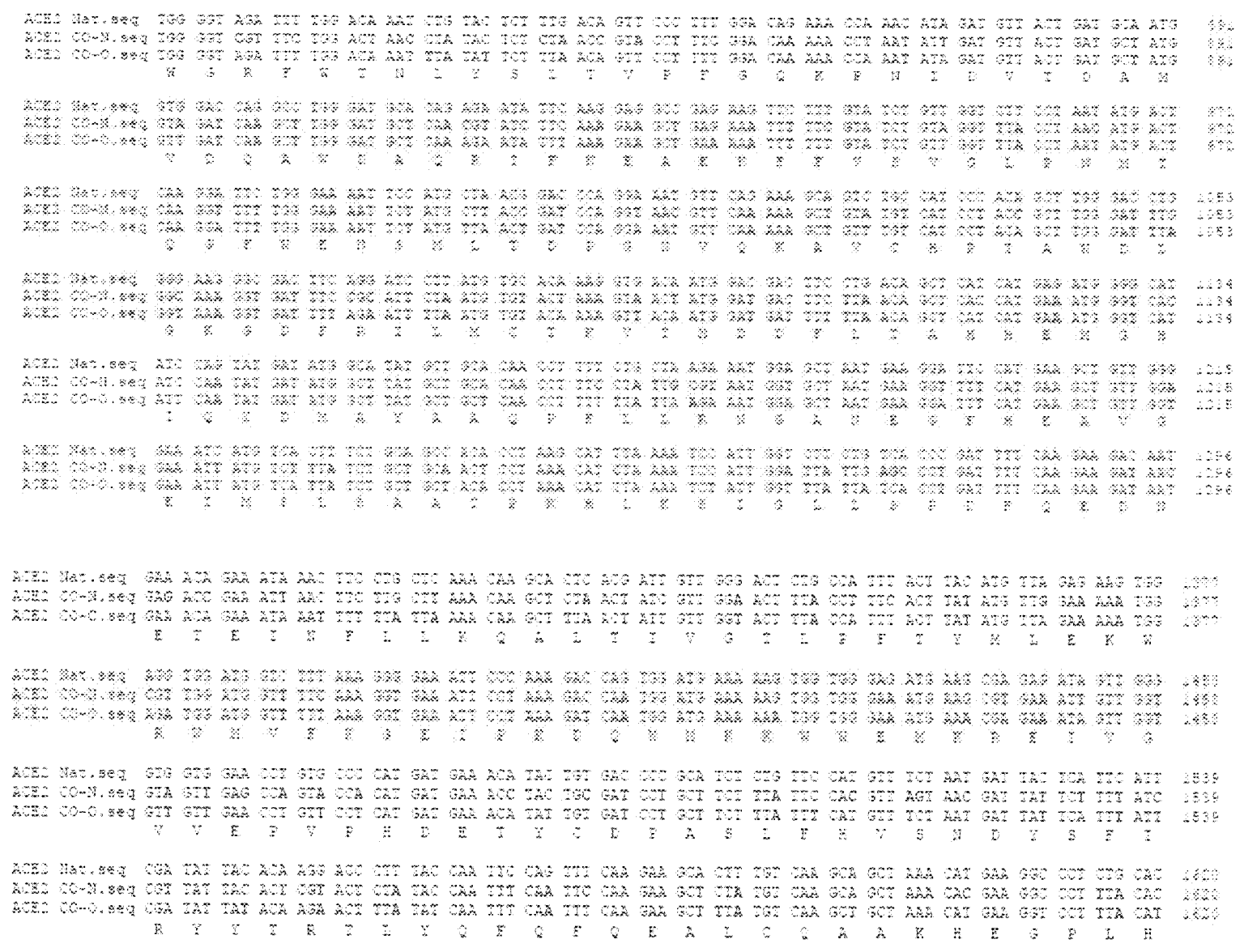
Figure 20D:
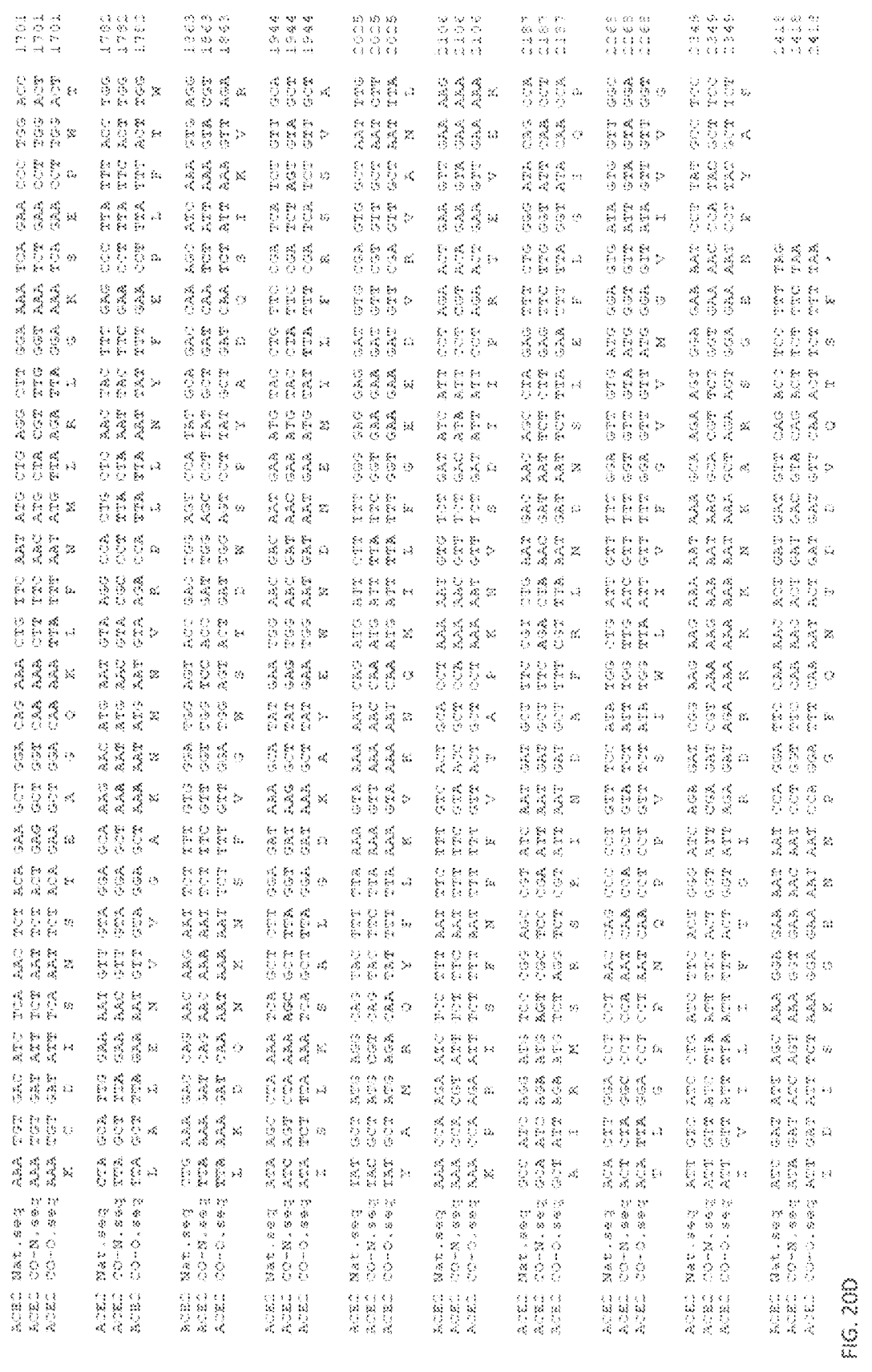

FIGS. 20A-20D. Codon distribution of psbA (FIG. 20A), chloroplast based codon tables, native and codon-optimized (N and O) ACE2 gene. Codon-optimized ACE2 were optimized by changing the rare codons and codons usage frequency to resemble the chloroplast psbA gene (FIGS. 20B, C and D). Sequence alignments of native and codon-optimized (N and O) ACE2 gene. Any different nucleotides of codon-optimized sequences are marked in light grey. Nat: native sequence; CO—N: codon-optimized sequence obtained from new version of optimizer; CO—O: codon-optimized sequence obtained from old version of optimizer.

Figure 21B:
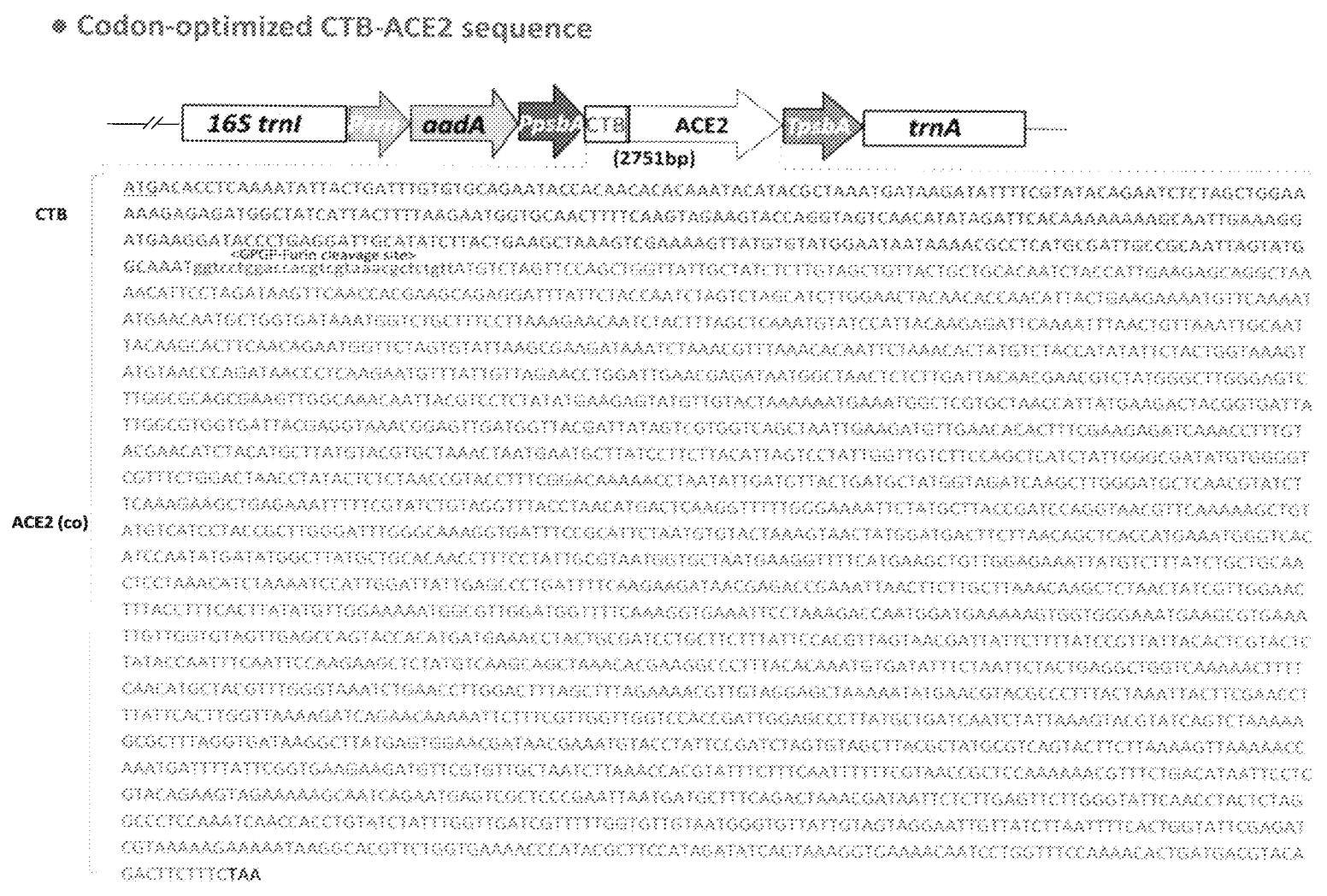

FIGS. 21A and 21B. Native and Optimized CTB-ACE2 Constructs and Sequences. FIG. 21A. Native sequence (SEQ ID NO: 23). FIG. 21B. Codon optimized sequence (SEQ ID NO: 24).

FIGS. 22A-22D. Selection and regeneration of CTB-ACE2 transplastomic lettuce. (FIG. 22A) transplastomic lettuce shoots undergoing first round of selection; (FIG. 22B) second rounds of selection; CTB-ACE2 lettuce acclimated in growth chamber (FIG. 22C) and grown in greenhouse (FIG. 22D).

DETAILED DESCRIPTION OF THE INVENTION

Figure 2A:
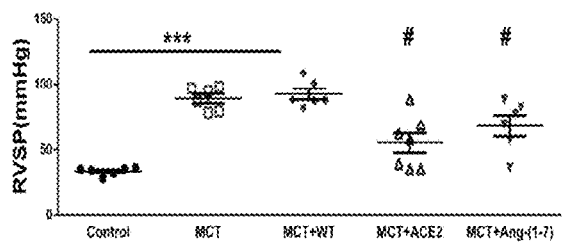
FIGS. 2A-2H. Oral administration of bioencapsulated ACE2 or Ang-(1-7) prevents MCT-induced PH.

Embodiments disclosed herein provide a method for treating subjects suffering from chronic diseases such as cardiovascular disease, cardiopulmonary disease, and other lung diseases involving pulmonary fibrosis, diabetes-related micro- and macro-vascular diseases, metabolic syndrome, stress-related disorders and ocular disorders. For example, studies have shown that overexpression of ACE2 or Ang-(1-7) in the lungs or its activation by small molecule activators prevents pulmonary hypertension-induced lung pathophysiology (Shenoy et al, Curr Opin Pharmacol 2011, 11:150-5. Shenoy et al, Am J Respir Crit Care Med. 2013, 187(6):648-57). In addition, ACE2 activators attenuate ischemia-induced cardiac pathophysiology (Qi et al, Hypertension. 2013, 62(4):746-52) and produce beneficial effects on dysfunctional diabetic EPCs (Jarajapu et al, Diabetes, 2013, 62, 1258-69. Since this enzyme is a protein, the only effective way to increase its levels in a diseased state is to administer it intravenously or intramuscularly. Both of these methods of delivery are extremely inefficient, and cost prohibitive in a pre-clinical trials and subsequent use in therapeutics. Chloroplast-derived ACE2 and Ang-(1-7) should reduce cost and facilitate oral delivery of these therapeutic proteins, thus making it attractive for clinical trials for above mentioned chronic diseases.

In Example 2, we described methods for enhancing the systemic and local activity of the protective axis of the RAS by oral delivery of ACE2 and Ang-(1-7) bioencapsulated in plant cells for conferring protection against endotoxin induced uveitis (EIU) and experimental autoimmune uveoretinitis (EAU). Both ACE2 and Ang-(1-7), fused with the non-toxic cholera B subunit B (CTB) were expressed in plant chloroplasts. The effects of orally delivered CTB-ACE2/Ang-(1-7) on EIU and EAU models in C57B6/J and B10.RIII mice respectively were examined. Increased levels of ACE2 and Ang-(1-7) were observed in circulation and retina after oral administration of CTB-ACE2/Ang-(1-7) leaf materials. Oral feeding of mice with bioencapsulated ACE2 or Ang-(1-7) significantly reduced LPS induced infiltration of inflammatory cells and expression of inflammatory cytokines in the eye; this treatment also dramatically decreased cellular infiltration, retinal vasculitis, damage and folding in EAU eyes. Thus, enhancing the protective axis of RAS by oral delivery of ACE2/Ang-(1-7) bioencapsulated in plant cells provide an innovative, more efficient and cost-effective therapeutic strategy for ocular inflammation such as uveitis and autoimmune uveoretinitis.

Definitions

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "disease," "disorder," or "complication" refers to any deviation from a normal state in a subject.

As used herein, by the term "effective amount" "amount effective," or the like, it is meant an amount effective at dosages and for periods of time necessary to achieve the desired result.

As used herein, the term "inhibiting" or "preventing" means causing the clinical symptoms of the disease state not to worsen or develop, e.g., inhibiting the onset of disease, in a subject that may be exposed to or predisposed to the disease state, but does not yet experience or display symptoms of the disease state.

As used herein, the term "expression" in the context of a gene or polynucleotide involves the transcription of the gene or polynucleotide into RNA. The term can also, but not necessarily, involves the subsequent translation of the RNA into polypeptide chains and their assembly into proteins.

A plant remnant may include one or more molecules (such as, but not limited to, proteins and fragments thereof, minerals, nucleotides and fragments thereof, plant structural components, etc.) derived from the plant in which the protein of interest was expressed. Accordingly, a composition pertaining to whole plant material (e.g., whole or portions of plant leafs, stems, fruit, etc.) or crude plant extract would certainly contain a high concentration of plant remnants, as well as a composition comprising purified protein of interest that has one or more detectable plant remnants. In a specific embodiment, the plant remnant is rubisco.

In another embodiment, the invention pertains to an administrable composition for treating or preventing pulmonary hypertension or pulmonary hypertension-induced lung pathophysiology. The composition comprises a therapeutically-effective amount of ACE2, Ang-(1-7), CTB-ACE2 or CTB-Ang-(1-7), or a combination thereof having been expressed by a plant and a plant remnant. The compositions of the invention may also be used to advantage to treat ocular inflammation.

Methods, vectors, and compositions for transforming plants and plant cells are taught for example in WO 01/72959; WO 03/057834; and WO 04/005467. WO 01/64023 discusses use of marker free gene constructs.

Proteins expressed in accord with certain embodiments taught herein may be used in vivo by administration to a subject, human or animal in a variety of ways. The pharmaceutical compositions may be administered orally or parenterally, i.e., subcutaneously, intramuscularly or intravenously, though oral administration is preferred.

Oral compositions of the present invention can be administered via the consumption of a foodstuff that has been manufactured with the transgenic plant producing the plastid derived therapeutic protein. The edible part of the plant, or portion thereof, is used as a dietary component. The therapeutic compositions can be formulated in a classical manner using solid or liquid vehicles, diluents and additives appropriate to the desired mode of administration. Orally, the composition can be administered in the form of tablets, capsules, granules, powders and the like with at least one vehicle, e.g., starch, calcium carbonate, sucrose, lactose, gelatin, etc. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol or the like and combination thereof. In addition, if desired, the compositions may contain minor amounts of auxiliary substances such as wetting or emulsifying agents, pH buffering agents, or adjuvants. In a preferred embodiment the edible plant, juice, grain, leaves, tubers, stems, seeds, roots or other plant parts of the pharmaceutical producing transgenic plant is ingested by a human or an animal thus providing a very inexpensive means of treatment of or immunization against disease.

In a specific embodiment, plant material (e.g. lettuce material) comprising chloroplasts capable of expressing ACE2, Ang-(1-7), CTB-ACE2 or CTB-Ang-(1-7), or a combination thereof, is homogenized, lyophilized and encapsulated. In one specific embodiment, an extract of the lettuce material is encapsulated. In an alternative embodiment, the lettuce material is powderized before encapsulation.

In alternative embodiments, the compositions may be provided with the juice of the transgenic plants for the convenience of administration. For said purpose, the plants to be transformed are preferably selected from the edible plants consisting of tomato, carrot and apple, among others, which are consumed usually in the form of juice.

According to another embodiment, the subject invention pertains to a transformed chloroplast genome that has been transformed with a vector comprising a heterologous gene that expresses a peptide as disclosed herein.

Of particular present interest is a chloroplast genome that has been transformed with a vector comprising a heterologous gene that expresses one or more polypeptides selected from ACE2, Ang-(1-7), CTB-ACE2 or CTB-Ang-(1-7), or a combination thereof. In a related embodiment, the subject invention pertains to a plant comprising at least one cell transformed to express a peptide as disclosed herein.

Reference to CTB and ACE2 or Ang-(1-7) sequences herein relate to the known full length amino acid sequences as well as at least 12, 15, 25, 50, 75, 100, 125, 150, 175, 200, 225, 250 or 265 contiguous amino acids selected from such amino acid sequences, or biologically active variants thereof. Typically, the polypeptide sequences relate to the known human versions of the sequences.

Variants which are biologically active, refer to those, in the case of oral tolerance, that activate T-cells and/or induce a Th2 cell response, characterized by the upregulation of immunosuppressive cytokines (such as IL10 and IL4) and serum antibodies (such as IgG1), or, in the case of desiring the native function of the protein, is a variant which maintains the native function of the protein. Preferably, naturally or non-naturally occurring polypeptide variants have amino acid sequences which are at least about 55, 60, 65, or 70, preferably about 75, 80, 85, 90, 96, 96, or 98% identical to the full-length amino acid sequence or a fragment thereof. Percent identity between a putative polypeptide variant and a full length amino acid sequence is determined using the Blast2 alignment program (Blosum62, Expect 10, standard genetic codes). Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of polypeptide can be found using computer programs well known in the art, such as DNASTAR software. Whether an amino acid change results in a biologically active LecA polypeptide can readily be determined by assaying for native activity, as described for example, in the specific Examples, below.

Reference to genetic sequences herein refers to single- or double-stranded nucleic acid sequences and comprises a coding sequence or the complement of a coding sequence for polypeptide of interest. Degenerate nucleic acid sequences encoding polypeptides, as well as homologous nucleotide sequences which are at least about 50, 55, 60, 65, 60, preferably about 75, 90, 96, or 98% identical to the cDNA may be used in accordance with the teachings herein polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of nucleic acid sequences which encode biologically active polypeptides also are useful polynucleotides.

Variants and homologs of the nucleic acid sequences described above also are useful nucleic acid sequences. Typically, homologous polynucleotide sequences can be identified by hybridization of candidate polynucleotides to known polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of polynucleotides referred to herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Nucleotide sequences which hybridize to polynucleotides of interest, or their complements following stringent hybridization and/or wash conditions also are also useful polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between a polynucleotide of interest or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m=81.5°\ C.-16.6(\log_{10}[Na^+])+0.41(\%\ G+C)-0.63(\%\ \text{formamide})-600/l),$$

where l=the length of the hybrid in basepairs. Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

The Examples set forth below are provided to illustrate certain embodiments of the invention. They are not intended to limit the invention in any way.

Example 1

Creation of Transplastomic Plants Expressing CTB-ACE2 and CTB-Ang-(1-7)

In the present example, we describe a low cost oral delivery system for administering ACE2 or Ang-(1-7) and test its efficacy in an experimental model of PH. We took advantage of transplastomic technology which enables chloroplasts to generate high levels of therapeutic proteins within plant leaves.[16,21] This technology presents minimal risk of human pathogen or endotoxin contamination, eliminates complex protein purification steps, and abolishes cold chain and sterile delivery requirements that are commonly associated with protein therapy.[22-24] Efficacy of plant-based pharmaceuticals has been validated by the fact that FDA has recently approved the use of taliglucerase alfa (Trade name: Elelyso) in the treatment of Gaucher's disease.[25] This study provides evidence for the development of an oral delivery system to administer ACE2 and Ang-(1-7) using transplastomic technology, and demonstrates its efficacy in an established rat model of monocrotaline (MCT)-induced PH.

The following materials and methods are provided to facilitate the practice of Example 1.

Chloroplast Transformation Vector Construction and Regeneration of Transplastomic Lines The cDNA for ACE2 (accession: NM_021804) was used as the template to clone CTB-ACE2 fusion gene into the intermediate vector. To clone CTB-Ang-(1-7) fusion gene, CTB-containing vector was used as template with a forward primer specific to CTB and a reverse primer specific to CTB but including nucleotide sequence corresponding to 7 amino acid of Ang-(1-7) peptide. The sequence-confirmed chimeric gene was cloned into chloroplast transformation vector, pLD.

Southern Blot Analysis

To investigate transgene integration and homoplasmy, Southern blot analysis was performed as previously described.[1] Total genomic DNA was digested with HindIIII, separated on a 0.8% agarose gel at 15 V overnight, transferred onto nylon membrane. The 0.8-kb flanking region probe was generated by digesting the pUC-CT vector DNA with BamHI and BglII. The probe was labeled with dCTP using Klenow fragment (Promega M220A) and random primers (Promega C1181). After labeling the probe, the blotted membrane was hybridized with hybridization solution [0.5 M phosphate buffer pH 7.2, 1 mM EDTA pH 8.0, 7% (w/v) SDS, 1% (w/v) bovine serum albumin] at overnight at 65° C. then washed with 2×SSC, 0.2% SDS for 30 min once and 1×SSC, 0.1% SDS for 15 min twice each. Radioisotope-labelled blots were exposed to X-ray film at −80° C. for 8 h.

Quantification of CTB-ACE2 and CTB-Ang-(1-7) Fusion Protein

Leaves ground in liquid nitrogen was resuspened in extraction buffer [100 mM NaCl, 10 mM EDTA, 200 mM Tris-Cl pH 8.0, 0.1% (v/v) Triton X-100, 400 mM sucrose, 2 mM PMSF, and proteinase inhibitor cocktail] in a ratio of 100 mg to 300 μL, then vigorously mixed using vortex (~30 s) and sonicated twice (pulse on for 5 s and pulse off for 10 s). Homogenate protein was quantified using Bradford assay. For the quantification of CTB-ACE2 protein, ELISA was performed. Ninety-six-well plates were coated with serially diluted CTB standard (25-12.5-6.25-3.13-1.56-0.781-0.391-0.195 pg/μL; Sigma C9903) and CTB-ACE2 proteins (4,000-8,000-16,000) in bicarbonate buffer (15 mM $Na_2CO_3$, 35 mM $NaHCO_3$, 3.08 mM $NaN_3$, pH 9.6), then incubated overnight at 4° C. After washing the plates with 1× phosphate buffered saline (Fisher IC-N2810307) containing 0.05% (v/v) Tween 20 (1×PBST), the coated plates were blocked with 1×PBST containing 3% skim milk (PTM) for one and half hr at 37° C. and incubated with rabbit anti-CTB polyclonal antibody (1:10,000 in PTM; GenWay 18-511-245283) overnight at 4° C. The plates were followed by incubating with goat anti-rabbit IgG-HRP secondary antibody (1:4,000 in PTM; Southern Biotechnology 4030-05) for one and half hr at 37° C. after washing with 1×PBST thrice. The antibody-bound plates were washed with 1×PBST thrice and 1×PBS once before adding the 100 μL of tetramethyl benzidine (TMB) solution substrate (American Qualex Antibodies UCFL-05801). The reaction was stopped by adding the 50 μL of 2N $H_2SO_4$ and read on a plate reader at 450 nm. CTB-Ang-(1-7) was quantified using western blot and densitometric analysis. Total homogenate protein (0.5 μg) and CTB standards (3, 6, and 9 ng) was separated on SDS-PAGE and transferred to nitrocellulose membranes. Rabbit anti-CTB polyclonal antibody (1:10,000 in PTM; GenWay) and goat anti-rabbit IgG-HRP secondary antibody (1:4,000 in PTM; Southern Biotechnology) was used to detect the fusion proteins. SuperSignal West Pico Chemiluminescent Substrate (Pierce 34080) was used for autoradiographic detection. Then the developed films were analyzed by densitometry using Image J (IJ 1.46r; NIH). The known amounts of CTB standard were plotted and then the protein samples were interpolated on the graph. For the separation of proteins under non-reducing conditions, proteins were extracted as described above. The extracted proteins were combined with tricine sample buffer (Bio-Rad 161-0730), in the absence of reducing agents and without boiling prior to running on SDS-PAGE gels.

GM1 Binding Assay

To evaluate pentameric structure, GM1 binding assay was performed. Ninety-six-well plates were coated with monosialoganglioside-GM1 (Sigma G-7641) (3.0 μg/mL in bicarbonate buffer: 15 mM $Na_2CO_3$, 35 mM $NaHCO_3$, pH 9.6) overnight at 4° C. The plates were washed with PBST thrice and blocked with PTM. After washing the plates with 1×PBST, homogenate plant protein was diluted to concentration of 0.1 μg/μL with the same plant extraction buffer and incubated in the GM1 coated plates overnight at 4° C., along with CTB (1 ng/Sigma), bovine serum albumin (1% w/v BSA) and untransformed wild type plant protein (0.1 μg/μL) as controls. The plates were blocked with PTM for one and half hr at 37° C. After discarding the PTM, rabbit anti-CTB polyclonal antibody (1:10,000 in PTM; GenWay) was incubated overnight at 4° C. Following washing three times with 1×PBST, goat anti-rabbit IgG-HRP secondary antibody (1:4,000 in PTM; Southern Biotechnology) was incubated for one and half hr at 37° C. The plates were washed with PBST thrice and with PBS once and 100 μL of tetramethyl benzidine (TMB) solution substrate (American Qualex Antibodies UCFL-05801) was added to the wells and incubated under dark for 5 min. The reaction was stopped by adding 50 μL of 2N $H_2SO_4$, and read the absorbance at 450 nm using plate reader (Bio-rad Model 680).

Lyophilization

Frozen leaf tissues stored at −80° C. were crumbled into small pieces and transferred to 200 ml containers and sealed with porous 3M Millipore Medical Tape. The plant samples were freeze-dried in vacuum at −52° C. at 0.036 mBar for three days, with the aid of VirTis BenchTop 6K freeze dryer system. Lyophilized leaf material was stored in sealed container at room temperature with silica gel.

PH Study Design

We used the monocrotaline (MCT) animal model of PH to evaluate the therapeutic efficacy of oral feeding of ACE2, Ang-(1-7) or their combination against disease pathogenesis. Animals were randomly assigned to respective experimental groups based on their body weights at the time of MCI administration. The study design consisted of prevention and reversal protocol s. All animal procedures were approved by the Institutional Animal Care and Use Committee at the University of Florida and complied with National Institutes of Health guidelines.

Gavage Feeding of MCT Rats with Bioencapsulated ACE2 or Ang-(1-7)

8-week-old male Sprague Dawley rats (Charles River Laboratories) were injected with a single subcutaneous dose of MCT (50 mg/kg, Sigma Aldrich, USA). Control animals received an equivalent amount of sterile saline (~500 For the prevention protocol, a subset of MCT animals was simultaneously orally gavaged with wild type leafy material, bioencapsulated ACE2 or Ang-(1-7) [500 mg, twice daily in sterile phosphate-buffered saline (PBS)] for a period of 28 days. For the reversal protocol, ACE2, Ang-(1-7) or their combination [500 mg or 250 mg each of ACE2 and Ang-(1-7)] was gavage-fed after 2 weeks of MCT administration and continued for additional 15 days.

Echocardiography Measurement

Four weeks after MCT injection, transthoracic echocardiography was performed using GE vivid7 ultrasound machine with a 12-MHz transducer (GE Healthcare, NJ, USA). Rats were anesthetized with the 2% isoflurane-oxygen mixture. M-mode echocardiography was measured at the parasternal short-axis view at the level of papillary muscles. Left ventricular ejection fraction (LVEF) was calculated from the M-mode. Further, at this view, right and left ventricular end diastolic area (RVEDA and LVEDA) and right ventricular ejection fraction (RVEF) were also measured. Pulsed Doppler recordings performed at the parasternal short-axis view at the base of the heart to measure the right ventricle outflow tract (RVOT $V_{max}$). ECG was recorded simultaneously for all the assessments. All the recordings were performed in triplicates. Ejection fraction was obtained from both right and left ventricles and was represented as the ratio between right and left ventricle. Similarly, end diastolic area was also represented as the ratio between right and left ventricle. Blood flow at the right ventricular outflow tract was represented as RVOT Vmax (m/s). Three consecutive cycles from each recording (totally 9 cycles) were averaged to assess each parameter. Following the echocardiographic measurements, animals were subjected to hemodynamic measurements.

Right Ventricular Systolic Pressure (RVSP) Measurements

The RVSP was measured in anesthetized animals [subcutaneous injection of a mixture of ketamine (30 mg/Kg) and Xylazine (6 mg/Kg)] using a fluid-filled silastic catheter, which was inserted inside the right descending jugular vein and advanced to the right ventricle. The catheter was connected to a pressure transducer that was interfaced to a PowerLab (AD Instruments, USA) signal transduction unit. The waveform was used to confirm the positioning of the catheter in the right ventricle. RVSP, +dP/dt, −dP/dt and right ventricular end diastolic pressure (RVEDP) were obtained using the Chart program supplied along with the PowerLab system. For both prevention and reversal protocols RVSP was measured after 4 weeks of MCT-challenge.

Hypertrophy and Histological Analysis

Following RVSP measurements, a thoracotomy was performed, and after exsanguination, the heart and lungs were removed en bloc. To calculate right ventricular hypertrophy (RVH), the wet weight of RV and left ventricle plus ventricular septum (LV+S) was determined. RVH was expressed as the ratio of RV/[LV+S] weights. The RV was further processed for histological analysis of collagen content. Briefly, RV was fixed in 10% neutral buffered formalin, embedded in paraffin, sectioned at 5 µm and stained with picro-sirius red. Interstitial fibrosis was determined at 100× magnification using the ImageJ program from National Institutes of Health, as previously described.[2] A minimum of 5-8 separate images from different (non-overlapping) regions of the right ventricle were obtained. The results for each animal were then averaged for subsequent statistical analysis. To carry out histological examination of the lung, the left lung alone was perfused with PBS followed by 10% neutral buffered formalin. For measuring pulmonary medial wall thickness, 5 µm thick lung sections were cut paraffin embedded and stained for α-smooth muscle actin (1:600, clone 1A4, Sigma Aldrich, USA). Vessels with an external diameter of <50 µm were considered to measure the medial wall thickness. For each rat, around 10 vessels were counted and the average was calculated. The percent medial wall thickness was calculated using the formula: % Medial wall thickness=[(medial thickness×2)/external diameter]×100 (n=5 rats per group) Media thickness was defined as the distance between the lamina elastica interna and lamina elastica externa.

Real-Time RT-PCR Analysis

Semi-quantitative real time RT-PCR was used to determine mRNA levels of the renin-angiotensin system components viz. ACE, ACE2, AT1R, and AT2R, and pro-inflammatory cytokines (PICs) viz. Tumor Necrosis Factor-alpha (TNF-α), Transforming Growth Factor-beta (TGF-β) and toll-like receptor-4 (TLR-4) as described previously.[2] Total RNA isolation, cDNA synthesis and RT-PCR were performed as previously described. In brief, total RNA was isolated from punched tissues using TRIzol reagent (Invitrogen, USA) according to the manufacturer's specifications. The RNA concentration was calculated from the absorbance at 260 nm and RNA quality was assured by 260/280 ratio. Only RNA samples exhibiting an absorbance ratio (260/280) of >1.6 were used for further experiments. The RNA samples were treated with DNase I (Ambion, USA) to remove any genomic DNA. First strand cDNA was synthesized from 2 µg RNA with iScript cDNA synthesis kit (Bio-Rad, USA). Real-time RT-PCR was performed in 384-well PCR plates using iTaq SYBR Green Super mix with ROX (Bio-Rad) in triplicate using the ABI Prism 7900 sequence detection system (Applied Biosystems, USA). The PCR cycling conditions were as follows: 50° C. for 2 min, 95° C. for 3 min, followed for 45 cycles (15 s at 95° C., and 1 min at 60° C.). To confirm the specific PCR product, a dissociation step (15 s at 95° C., 15 s at 60° C., and 15 s at 95° C.) was added to check the melting temperature. Gene expression was measured by the ΔΔCT method and was normalized to 18S mRNA levels. The data are presented as the fold change of the gene of interest relative to that of control animals.

Measurement of Ang-(1-7):

Circulating levels of Ang-(1-7) were measured using a commercially available EIA kit from Bachem Laboratories as per manufacturer's instructions.

Statistics

Prism 5 (GraphPad) was used for all analyses. Values are presented as means±SEM. Data were analyzed using one-way ANOVA followed by the Newman-Keuls test for multiple comparisons. P values less than 0.05 were considered statistically significant.

Results

Creation and Characterization of CTB-ACE2 and CTB-Ang-(1-7) Expressed in Plant Chloroplasts The native human ACE2 cDNA and synthetic Ang-(1-7) DNA sequences were cloned into the chloroplast transformation vector (pLDutr) (FIG. 1A). For efficient delivery of the proteins into circulation, a carrier protein, cholera non-toxic B subunit (CTB), was fused to the N-terminal of both therapeutic proteins (FIG. 1A), which facilitates their trans-mucosal delivery by binding to monosialotetrahexosylganglioside receptors (GM1) present on the intestinal epithelial cells. Hinge (Gly-Pro-Gly-Pro; SEQ ID NO: 1) and furin cleavage site (Arg-Arg-Lys-Arg; SEQ ID NO: 2) were placed between CTB and therapeutic proteins (FIG. 1A) to eliminate steric hindrance and aid systemic release of these therapeutic proteins after they are internalized via ligand-receptor complex formation on the surface of epithelial cells. The expression of the fusion genes was driven by light regulated strong chloroplast psbA promoter and the transcripts were stabilized by placing the psbA UTR at the 3' end of the fusion genes (FIG. 1A). To select the chloroplast transformed with the fusion genes, aminoglycoside-3"-adenylyl-transferase gene (aadA), driven by the chloroplast ribosomal RNA promoter (Prrn), was incorporated into the expression cassette to confer the transformants resistance to spectinomycin (FIG. 1A). This expression cassette was flanked by DNA sequences of isoleucyl-tRNA synthetase (trnI) and alanyl-tRNA synthetase (trnA) genes, identical to the native chloroplast genome at both flanks (FIG. 1A). The flanking sequences serve to facilitate transgene integration into the chloroplast genome (FIG. 1A) via double homologous recombination. Chloroplast transformation vectors expressing the ACE2 and Ang-(1-7) genes were coated onto gold particles and delivered into chloroplasts using the biolistic particle delivery system.[26] The bombarded plant leaves were then grown on spectinomycin containing plant regeneration media. The shoots regenerated from the media were investigated for the site specific integration of the transgenes into chloroplast genome and homoplasmy of the transgenes (absence of untransformed genomes) using Southern blot analysis with the radioisotope-labelled probe spanning trnI and trnA flanking sequences.[26] HindIII-digested chloroplast genomic DNA from three independent transplastomic lines for each transplastomic line showed two hybridizing fragments at 8.59 and 3.44 kb for CTB-ACE2 due to an internal Hind III site of ACE2 (FIG. 1A) and a fragment at 9.71 kb for CTB-Ang-(1-7), which confirm the absence of untransformed chloroplast genomes (FIGS. 1B and 1C). Thus, stable integration of the transgenes was confirmed and the homoplasmic lines were used for further studies. The confirmed homoplasmic lines were multiplied using another round of antibiotic selection under aseptic conditions. Then they were cultivated in a controlled greenhouse for increasing biomass. CTB-ACE2 expression varied between 1.69% and 2.14% of the total leaf proteins (TLP) (FIG. 1D), depending upon the harvest time because this transgene is regulated by light via the chloroplastpsbA promoter. Similarly, the expression level of CTB-Ang-(1-7) varied between 6.0% and 8.7% of TLP (FIG. 1E), at different durations of illumination, reaching maximum expression at the end of the day. Hence, for performing in vivo experimental studies, the therapeutic leaf materials were harvested at 6 pm and powdered in liquid nitrogen.

Both the therapeutic proteins were fused to the transmucosal carrier, CTB. The B subunit has a single intra-subunit disulfide bond which stabilizes the CTB monomer.[25] The monomers then assemble to form ring-shaped pentameric structure via inter-subunit interactions including hydrogen bonds, salt bridges, and hydrophobic interactions. Upon oral administration, only the pentameric form of CTB binds to the gut epithelial GM1 receptor for internalization.[27] Hence, we investigated the proper formation of pentameric structure of the CTB fused proteins and their binding affinity to GM1 receptor using GM1-ELISA. The binding affinity between CTB pentamers and the receptor was measured spectrophotometrically as a function of absorbance at 450 nm. The therapeutic proteins from the fresh leaf materials showed comparable absorbance to CTB (FIG. 1F), confirming that chloroplasts form disulfide-bridges, fold, and assemble these fusion proteins. We also lyophilized the leaves expressing ACE2 and Ang-(1-7), and evaluated their affinity to the GM1 receptor (FIG. 1F). Lyophilization not only maintained proper folding, disulfide bond and pentamer assembly but also facilitated long-term storage at room temperature (FIG. 1F). Furthermore, the Western blot assay performed under non-reducing conditions without DTT and boiling showed that there was no monomeric form or cleaved fragments of CTB-Ang-(1-7) (FIG. 1G). In the Western blot image, the major bands for pentameric assembly of CTB were detected around ~50 kDa (FIG. 1G, arrow head) and the expected bands for pentameric assembly of CTB-Ang-(1-7) were detected (FIG. 1G, arrow). Therefore, these results confirm that the therapeutic proteins expressed in chloroplasts exist in an intact and pentameric form.

Oral Feeding of Bioencapsulated ACE2 or Ang-(1-7) Prevents MCT-Induced PH

Figure 2B:
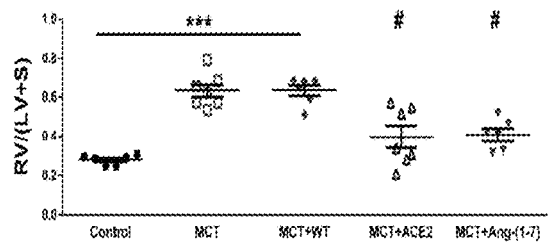
Figure 2C:
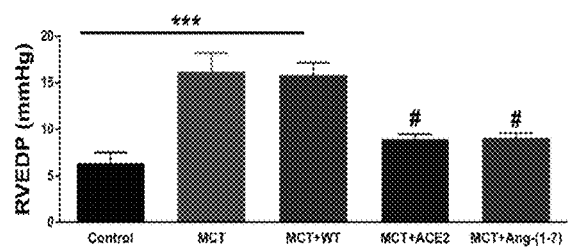
Figure 2D:
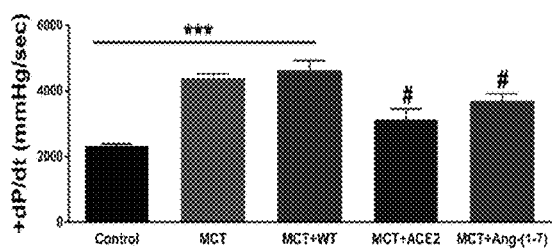
Figure 2E:
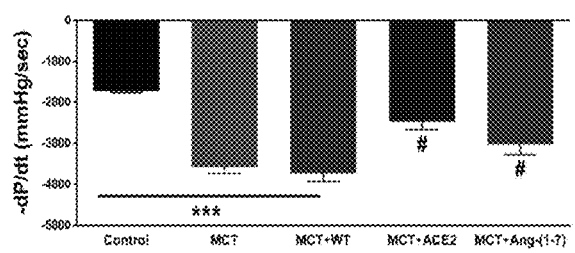
Figure 2F:
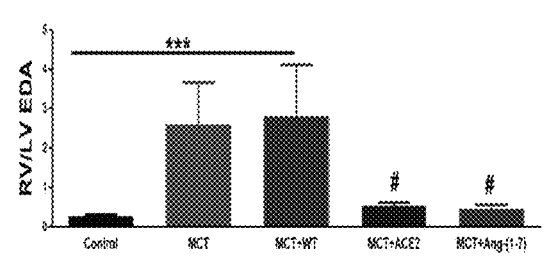
Figure 2G:
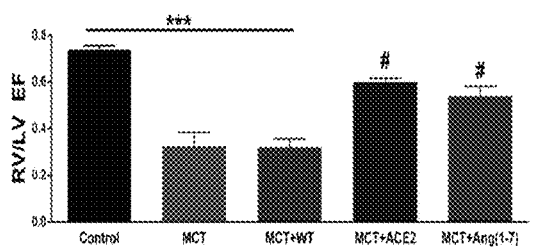
Figure 2H:
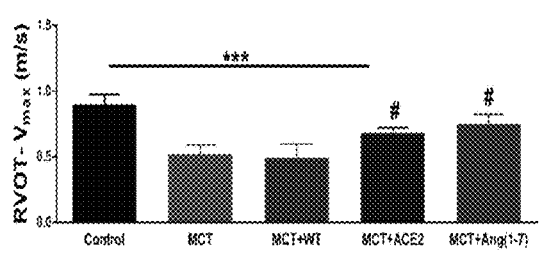
Figure 3A:
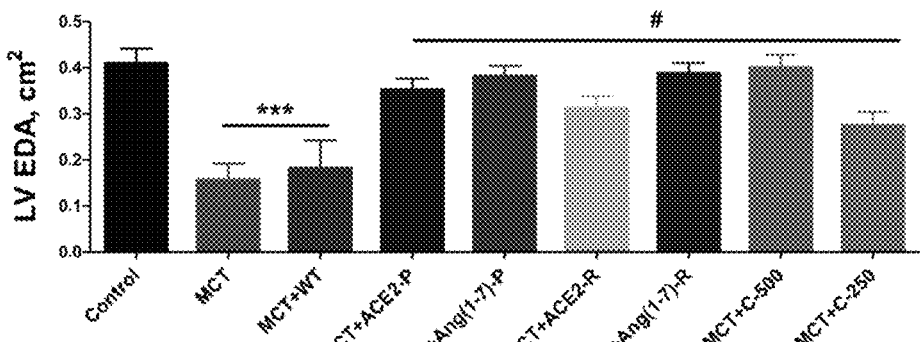
FIGS. 3A-3D. Oral feeding of bioencapsulated ACE2 or Ang-(1-7) improves cardiac function in PH as measured by echocardiography. Echocardiography was performed at the end of the study in M mode at the parasternal short axis view at the papillary muscle level as described in the Methods. Ejection fraction of the left ventricle was calculated using the following formula: (End Diastolic Volume−End Systolic Volume/End Diastolic Volume)×100. In the parasternal short axis view, the transducer was slightly angled to record the image of both right and left ventricle and this image was used to analyze the right and left ventricular end diastolic area.
Figure 3B:
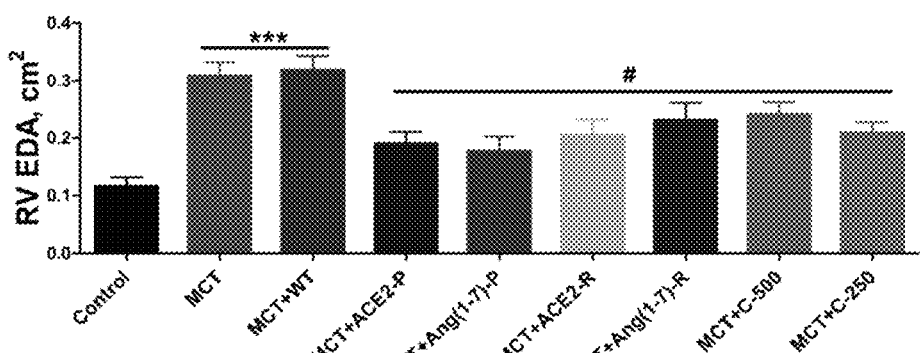
Figure 3C:
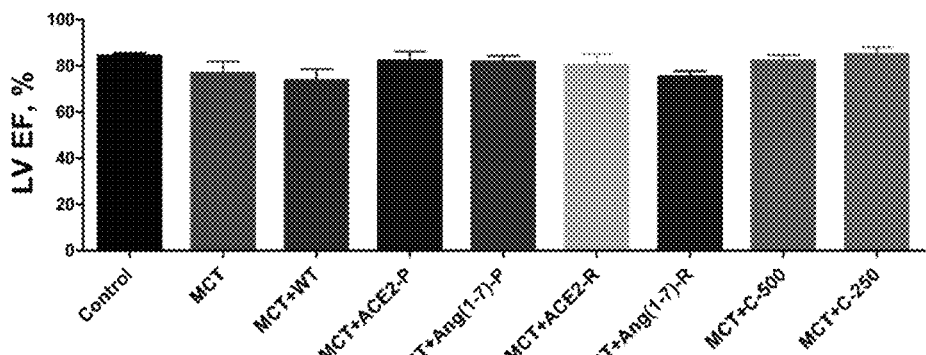
Figure 3D:
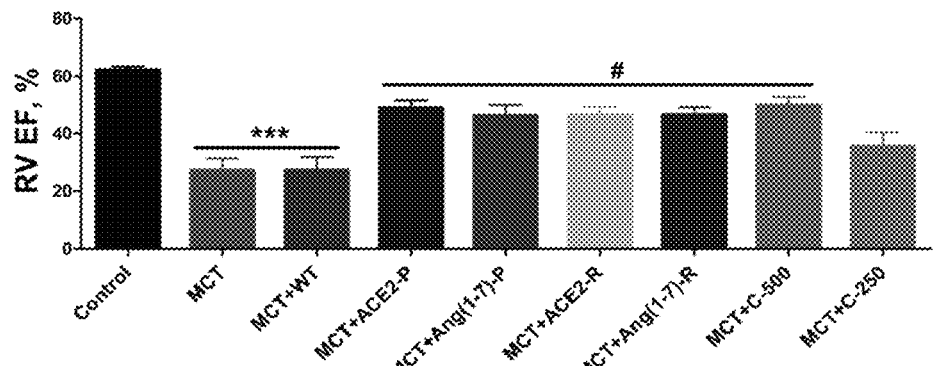

Oral gavage of the frozen powdered leaves (500 mg in sterile phosphate buffered saline) from untransformed wild type, CTB-ACE2 or CTB-Ang-(1-7) transplastomic plants was performed twice daily for 4-weeks in MCT-challenged rats. MCT injection caused robust elevation in right ventricular systolic pressure (RVSP; FIG. 2A) that was associated with the development of right ventricular hypertrophy (RVH) (FIG. 2B). In contrast, MCT animals gavaged with either ACE2 or Ang-(1-7) showed considerable reduction in RVSP and RVH (FIGS. 2A and 2B). Furthermore, measurement of hemodynamic parameters in MCT animals revealed increases in right ventricular end diastolic pressure (RVEDP; 153%), +dP/dt (88%) and −dP/dt (107%). Conversely, treatment with ACE2 or Ang-(1-7) restored all these parameters to near-control levels (FIGS. 2C, 2D, and 2E). Echocardiography of MCT rats revealed an increase in the ratio of right ventricle to left ventricle end diastolic area (RV/LV EDA), implying dilation of the right heart (FIG. 2F, and FIGS. 3A and 3B), which was accompanied with a decrease in ejection fraction (EF), measured as a ratio of RV/LV EF (FIG. 2G and FIGS. 3C and 3D). In addition, the pulsed Doppler blood flow measurement revealed decreased flow rate in the right ventricle outflow tract (RVOT) (FIG. 2H). Furthermore, video of the echocardiography revealed maladaptive structural remodeling in MCT rat hearts as compared with controls. However, oral delivery of ACE2 or Ang-(1-7) exhibited improved cardioprotective effects. Both ACE2 and Ang-(1-7) were effective in decreasing RV dilation (FIG. 2F), increasing EF (FIG. 2G) and preventing MCT-induced decrease in RVOT blood flow (FIG. 2H).

Figure 4:
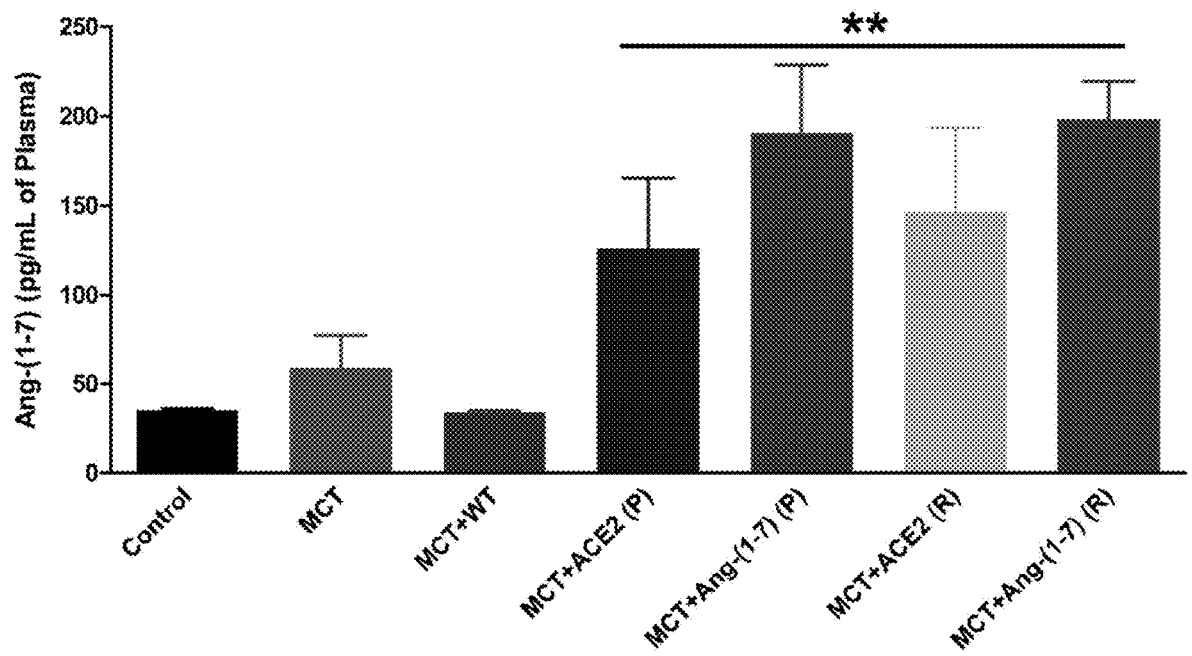
FIG. 4. Oral feeding of bioencapsulated ACE2 or Ang-(1-7) increases circulating levels of Ang-(1-7) in both prevention and reversal protocols. (A) Data indicates significant elevation in circulating levels of Ang-(1-7) in both prevention and reversal protocols (n=5 rats per group). (MCT+ACE2 (P) and MCT+Ang-(1-7) (P) represents the prevention protocol, while MCT+ACE2 (R) and MCT+Ang-(1-7) (R) represents the reversal protocol. Data represent mean±SEM with n=5 animals ** denoting p<0.01 as compared with normal controls, untreated and wild type plant material fed MCT animals as assessed by One-Way ANOVA followed by Newman-Keuls test.

These beneficial effects were associated with reduced cardiac remodeling as evidenced by echocardiography videos. Concurrently, RV fibrosis and pulmonary vessel wall thickness were also decreased (FIGS. 6A and 6B). Oral ACE2 feeding was associated with ~37% increase in circulating ACE2 activity as compared with MCT alone rats (FIG. 6C) and a two-fold increase in circulating levels of Ang-(1-7; FIG. 4). Interestingly, ACE2 or Ang-(1-7) did not alter the basal systemic blood pressure (SBP: Control, 120±5; MCT, 123±7; MCT±ACE2, 118±2; MCT±Ang-(1-7), 116±4; n=5/ experimental group).

Oral ACE2/Ang-(1-7) Treatment Arrests the Progression of Established PH

Figure 5A:
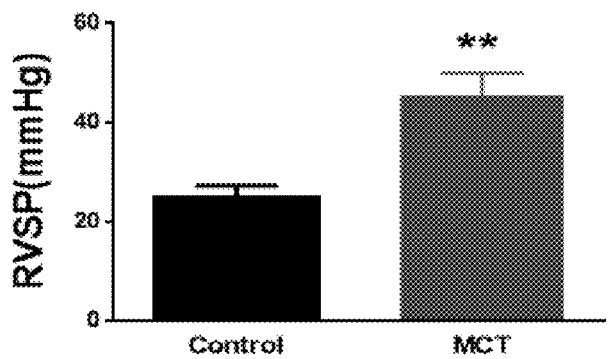
FIGS. 5A-5D. Oral feeding of bioencapsulated ACE2 or Ang-(1-7) exerts cardioprotective effects.
Figure 5B:
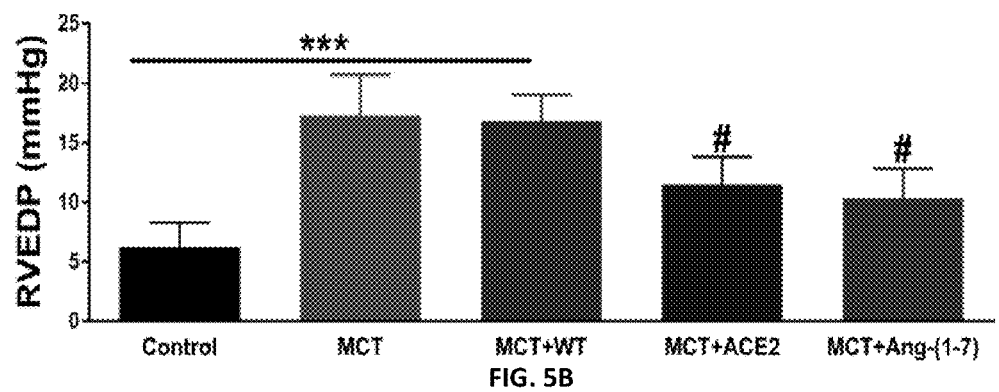
Figure 5C:
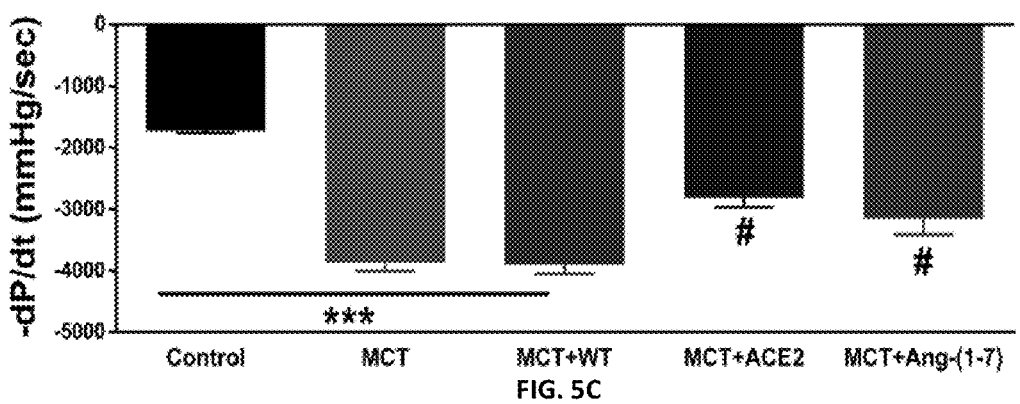
Figure 5D:
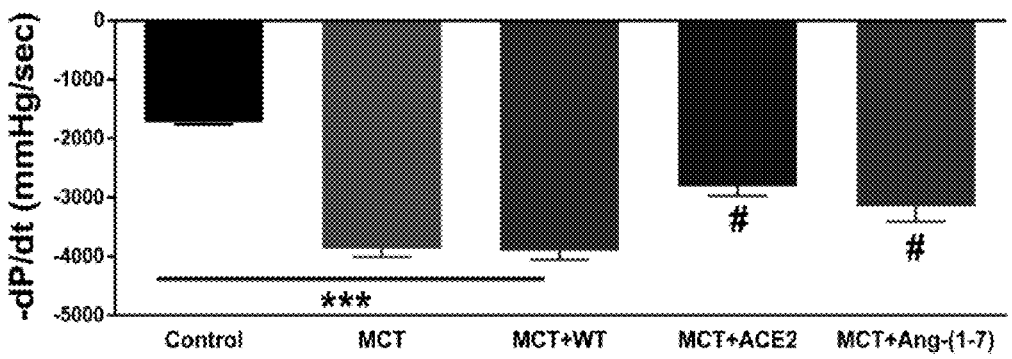

We next tested whether oral feeding of ACE2 or Ang-(1-7) after the initiation of PH could arrest the disease-progression. We observed that two-weeks of MCT challenge induces significant elevation in RVSP (>45 mmHg) as compared with controls (FIG. 5A) Hence, for this study, oral therapy was initiated after two-weeks of MCT challenge, and the treatment continued for additional 15-days. This regime of treatment with ACE2 or Ang-(1-7) inhibited further elevation in MCT-induced RVSP and RVH (FIGS. 7A and 7B), and was associated with increased circulating levels of Ang-(1-7; FIG. 4). Improvements in hemodynamic parameters with regard to lowering RVEDP, decreasing +dP/dt, and reducing −dP/dt were also observed (FIGS. 5B and 5D). In addition, ACE2/Ang-(1-7) therapy decreased RV dilation (FIG. 7C, and FIGS. 3A and 3B) and increased RVEF (FIG. 7D and FIGS. 3C and 3D), which was supported by echocardiography video. Subsequently, blood flow in the RVOT was also improved (FIG. 7E). Finally, RV fibrosis and pulmonary vessel wall thickening were significantly attenuated in ACE2/Ang-(1-7) treated animals (FIGS. 7F and 7G).

Combination Therapy with Oral ACE2 and Ang-(1-7) Feeding Rescues Established PH

Figure 8A:
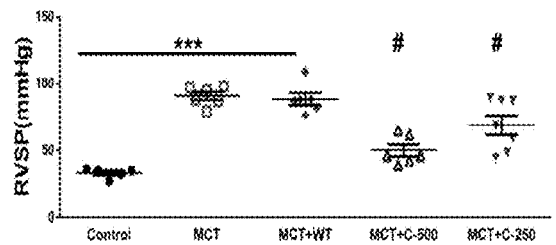
FIG. 8A-8H. Combination therapy with ACE2 and Ang-(1-7) rescues established PH.
Figure 8B:
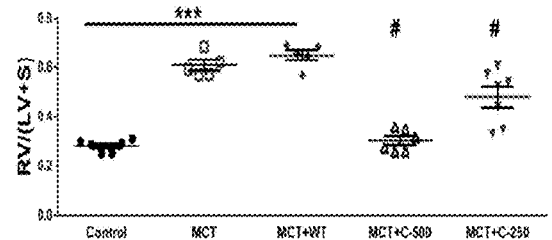
Figure 8C:
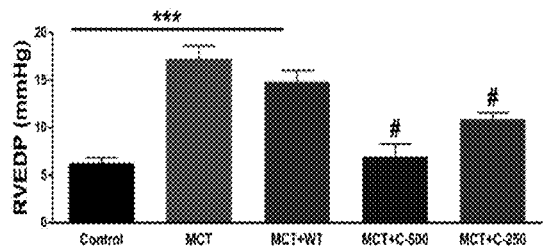
Figure 8D:
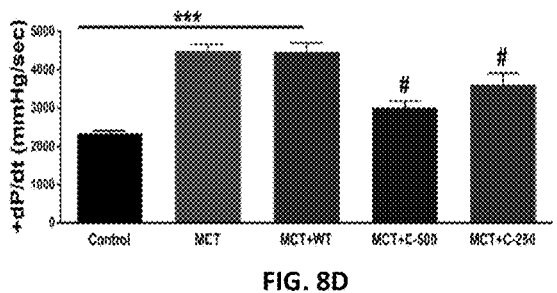
Figure 8E:
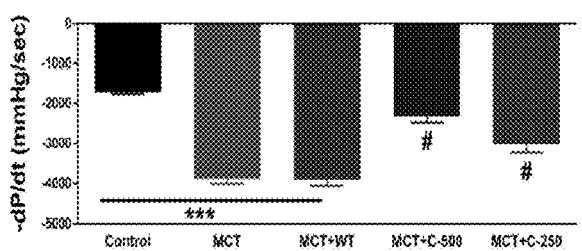
Figure 8F:
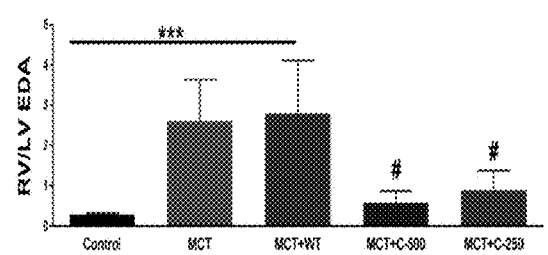
Figure 8G:
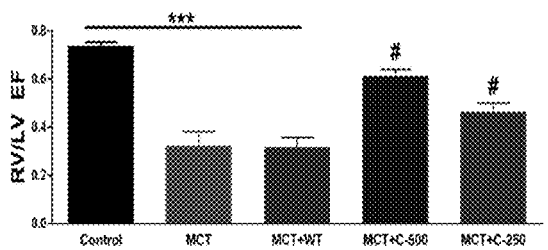
Figure 8H:
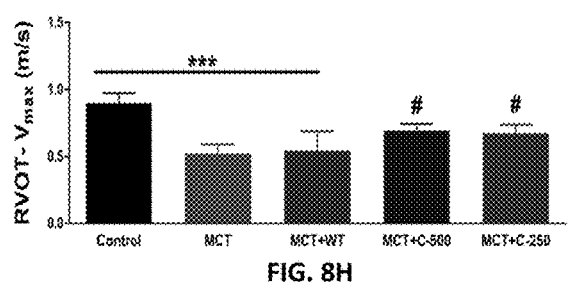

Next, we evaluated the effects of a combination therapy with ACE2 and Ang-(1-7), wherein 500 mg or 250 mg each of ACE2 and Ang-(1-7) plant material was combined. Reversal protocol was followed for this study, wherein the combination therapy was initiated after two-weeks of MCT challenge, and the treatment continued for the next 15 days. As expected, we observed better protective effects with the 500 mg combination. This combination showed 18% more reduction in RVSP and 25% additional decrease in RV/(LV+S) ratio when compared with the 250 mg combination (FIGS. 8A and 8B). Similarly, enhanced beneficial effects of the 500 mg combination were observed for other hemodynamic parameters such as RVEDP, +dP/dt, and −dP/dt (FIG. 8C to 8E). Both doses of the combination therapy were effective in decreasing RV dilatation (FIG. 8F, and FIGS. 3A and 3B), and increasing EF (FIG. 5G, and FIGS. 3C and 3D), which was accompanied by greater RVOT blood flow (FIG. 8H). All these observations were supported by echocardiography video. Consistent with this were the improvement in RV fibrosis and pulmonary vessel wall thickness following combination therapy (FIGS. 9A and 9B).

Beneficial Effects of ACE2/Ang-(1-7) Oral Therapy Involve Inhibition of Pro-Inflammatory Cytokines and Autophagy We demonstrate herein that oral delivery of ACE2 or Ang-(1-7) corrects RAS imbalance and inhibit pro-inflammatory cytokines. Data in FIG. 10 support this hypothesis. MCT rats revealed increased pulmonary mRNA levels of ACE and AT1R (FIGS. 10A and 10D), which resulted in 8-fold and 4-fold increases in the ACE/ACE2 and AT1R/AT2R ratios respectively (FIGS. 10C and 10F). Conversely, mRNA levels of ACE2 and AT2R were increased, while that of AT1R was decreased in the ACE2 or Ang-(1-7) fed MCT rats, resulting in decreased ACE/ACE2 and AT1R/AT2R ratios. Furthermore, MCT-challenged animals showed increased mRNA levels of TNF-α (4-fold), TGF-β (4-fold) and TLR-4 (5-fold), all of which were markedly reduced by ACE2 or Ang-(1-7) treatment (FIGS. 10G, 10H and 10I). Recent reports indicate that the autophagic protein degradation pathway is activated in MCT-challenged animals.[28] Accordingly, we observed that the lung LC3B-II protein, an autophagy marker, was significantly increased in MCT-challenged rats (FIG. 10J). However, ACE2 or Ang-(1-7) decreased LC3B-II levels, implying inhibition of autophagy. Similar results with respect to RAS modulation, anti-inflammatory properties and inhibition of autophagy were observed in the reversal protocol with monotherapy [either ACE2 or Ang-(1-7)] or combination therapy (FIG. 11A to 11J).

Discussion

Human ACE2 and Ang-(1-7) has been expressed within plant chloroplasts using transplastomic technology. Oral administration of transplastomic plant material to rats attenuates PH. While previous genetic interventions with ACE2/Ang-(1-7) have demonstrated beneficial effects in animals,[11,12] there are several challenges that limit the clinical development of such approaches. The incidence of PH is increasing among the elderly global population, necessitating affordable medication for the masses. While drugs made in plant cells have been approved by the FDA and are currently marketed,[25] targeted gene therapy is still in the experimental stage and far away from clinical applications. Even if gene therapy is approved as a valid approach, it would still be available to <1% of the global population due to the limited expertise available in hospitals for gene therapy. In contrast, oral delivery of capsules containing therapeutic proteins produced in plant chloroplasts is feasible and very much affordable. Accordingly, drug delivery is as important as drug discovery and this study focuses on the development of a novel low cost delivery system for administering therapeutic proteins like ACE2/Ang-(1-7), which have been found to be effective against experimental models of lung diseases, but not yet clinically approved. Injectable delivery of ACE2/Ang-(1-7) poses some unique challenges with respect to cost of manufacturing, protein stability, cold storage, shelf life, sterile delivery and requirement of health professionals/hospitals for their administration. Most of these concerns are easily eliminated by orally delivering therapeutic proteins bioencapsulated in plant cells. Currently produced injectable protein drugs are not affordable to more than half of the global population, despite decades of optimization of their process development. By developing an oral delivery system for administering ACE2 and Ang-(1-7), as reported here, we have made a tremendous advancement to move the field for the treatment of pulmonary diseases forward.

ACE2 and Ang-(1-7) were expressed in plant chloroplasts as fusion proteins with CTB. Though Ang-(1-7) is not a gene product, a synthetic gene encoding for Ang-(1-7), was used in this study.[29] We have used CTB as the transmucosal carrier to facilitate the uptake of ACE2 and Ang-(1-7) into circulation. Both CTB fusion proteins are disulfide bonded, form pentamers and properly folded, as observed for other CTB fusion proteins.[17,18] CTB is an approved adjuvant[39] that has been used in several clinical settings. Administration of CTB fused antigen (BD peptide) in humans with autoimmune eye disorders induced immunological tolerance by suppressing abnormal T cell reactivity against the peptide.[40] Also, immune suppression to autoantigens (proinsulin and factor IX) linked to CTB have been observed in animal studies following oral administration.[19,20] Likewise, other studies have shown immune-suppressive effects when CTB was fused to autoimmune or allergic causative agents.[41] The GM1 receptors present on intestinal epithelial cells make CTB the most appropriate carrier for transporting therapeutic proteins into systemic circulation as this receptor is widely distributed over the intestinal mucosa[42,43] with a rapid turnover rate.[44]

The half-life of native Ang-(1-7) is very short.[45,46] However, in this study, the stability of Ang-(1-7) was found to increase in sera. In plant cells, CTB stabilizes Ang-(1-7) by formation of pentamers (FIG. 1G), and thus confers protection from plant proteases. However, only monomers are observed in sera after delivery into the sera. While furin cleavage site (NH2-R—R—K—R—COOH) should facilitate removal of CTB, efficiency of cleavage depends upon the flanking amino acid sequence of the fused protein.[47] Ang-(1-7) fused to CTB didn't provide optimal furin cleavage site because it is not flanked by furin preferred basic amino acids at N-terminal side and serine-valine at C-terminal side. Therefore, it is anticipated that furin cleavage will not be rapid or efficient. This offers greater N-terminal protection to Ang-(1-7) and extends its stability for several hours in the sera as compared with injectable Ang-(1-7). Actually, chronic treatment with bioencapsulated Ang-(1-7) showed significant increases of the circulating levels of the peptide (FIG. 4), which suggests that an oral gavage twice daily of bioencapsulated Ang-(1-7) results in sustained elevated plasma levels of Ang-(1-7) in the treated animals. Ang-(1-7) concentration in frozen leaf materials was found to be 584 μg/g, which translates to 292 μg in 500 mg. This dose compares well with previous studies, wherein, 750-1000 μg/Kg of Ang-(1-7) peptide was administered to rats (~300 ug per 300 gms rat).

Oral feeding of bioencapsulated ACE2 or Ang-(1-7) prevents the development, and most importantly, retards the progression of MCT-induced PH. An upregulation of the deleterious ACE-AngII-AT1R axis and downregulation of the protective ACE2-Ang-(1-7)-Mas axis contributes to PH pathogenesis.[48] Thus, maintaining equilibrium between these two axes is crucial for preserving pulmonary vascular homeostasis. Oral delivery of ACE2 or Ang-(1-7) increased ACE2/ACE and decreased AT1R/AT2R ratios, signifying improvement in pulmonary RAS balance. In addition, the ACE2-fed MCT rats prevented the decrease in serum ACE2 activity observed in PH animals. Also, about 2-3 fold increase in the circulating levels of Ang-(1-7) in ACE2 treated animals was observed, which could possibly contribute to the protective effects (FIG. 4). ACE2 fed rats exhibited 37% increase in the enzymatic activity as compared with MCT alone animals. This increase in disease treated animals restored the enzymatic activity of circulating ACE2 to that of normal healthy rats. Most importantly, this increase was sufficient to exert beneficial effects against PH pathophysiology. Previous experimental studies have shown that exogenous administration of recombinant ACE2 increases serum ACE2 activity to exert therapeutic efficacy in several disease models.[49-51] Increasing serum ACE2 levels is also clinically significant since abnormally low levels of serum ACE2 have been associated with PH.[10] Surprisingly, pulmonary ACE2 mRNA levels were increased with oral ACE2 feeding. We speculate this increase to be a positive feed forward mechanism, since similar increases in ACE2 have been reported previously.[14,15] Also, AT2R levels were increased with ACE2 treatment, which is consistent with previous studies showing a protective role of this receptor in cardiopulmonary disease.[52] Furthermore, the favorable RAS modulation by ACE2 or Ang-(1-7) was associated with reduced lung inflammatory cytokines. Proinflammatory cytokines contribute to thickening of the pulmonary arterioles leading to heightened pulmonary pressure.[53] In line with these findings, we observed marked increases in vessel wall thickness in MCT-challenged animals. However, ACE2 or Ang-(1-7) treatment significantly inhibited medial wall thickness. The observed effects of ACE2/Ang-(1-7) could be attributed to reduction in proinflammatory cytokines as well as direct anti-proliferative actions on the vascular smooth muscle cells, a contention supported by earlier studies.[54] Recent studies have implicated autophagy in PH.[26] We observed an increase in LC3B-II, an autophagy marker, in MCT rats, which was significantly decreased with ACE2 or Ang-(1-7) treatment.

Collectively, the aforementioned findings indicate that oral delivery of ACE2 or Ang-(1-7) corrects a dysregulated pulmonary RAS, reduces inflammation, decreases vascular remodeling and inhibits autophagy to exert lung-protective effects. Importantly, ACE2/Ang-(1-7) treatment did not lower basal systemic blood pressure, which is important since induction of systemic hypotension can be detrimental in patients with PH. Similar phenomenon has also been observed in other studies, wherein, chronic administration of Ang-(1-7) fails to decrease systemic BP in a variety of models of hypertension[55-57]. One possibility may be related to pulmonary vasculature being more sensitive to Ang-(1-7) or that abundant receptors for Ang-(1-7) are present on the pulmonary vessels. Furthermore, a combination of ACE2 and Ang-(1-7) treatment produced beneficial effects on the cardiopulmonary system. We observed that the higher dose combination yielded better effects than the lower dose.

Of particular interest are the cardioprotective effects of oral ACE2/Ang-(1-7) therapy. Sustained pressure overload on the right heart induces ventricular remodeling and dysfunction.[58] Echocardiography of MCT rats revealed prominent structural changes in the heart. The RV assumed a round shape, with a shift in the intraventricular septum causing RV dilation with reduced EF. In addition, the pulmonary artery flow was significantly lowered in the MCT group. All these changes were associated with development of RVH, increased interstitial fibrosis and cardiac dysfunction. However, ACE2 or Ang-(1-7) treatment restored normal heart structure, inhibited RV dilatation and improved EF. Also, RVH and interstitial fibrosis were significantly reduced, along with preserved cardiac function. Moreover, the combination therapy with ACE2 and Ang-(1-7) was found to exert superior cardioprotective effects.

REFERENCES FOR EXAMPLE 1

1. Schermuly R T, Ghofrani H A, Wilkins M R, Grimminger F. Mechanisms of disease: pulmonary arterial hypertension. *Nat Rev Cardiol* 2011; 8:443-455.
2. Sutendra G, Michelakis E D. Pulmonary arterial hypertension: Challenges in translational research and a vision for change. *Sci Transl Med* 2013; 5:208sr5.
3. de Man F S, Tu L, Handoko M L, Rain S, Ruiter G, Francois C, Schalij I, Dorfmüller P, Simonneau G, Fadel E, Perros F, Boonstra A, Postmus P E, van der Velden J, Vonk-Noordegraaf A et al. Dysregulated renin-angiotensin-aldosterone system contributes to pulmonary arterial hypertension. *Am J Respir Crit Care Med* 2012; 186:780-789.
4. Morrell N W, Atochina E N, Morris K G, Danilov S M, Stenmark K R. Angiotensin converting enzyme expression is increased in small pulmonary arteries of rats with hypoxia-induced pulmonary hypertension. *J Clin Invest* 1995; 96:1823-1833.
5. Donoghue M, Hsieh F, Baronas E, Godbout K, Gosselin M, Stagliano N, Donovan M, Woolf B, Robison K, Jeyaseelan R, Breitbart R E, Acton S. A novel angiotensin-converting enzyme-related carboxypeptidase (ACE2) converts angiotensin I to angiotensin 1-9. *Circ Res* 2000; 87:e1-e9.
6. Tipnis S R, Hooper N M, Hyde R, Karran E, Christie G, Turner A J. A human homolog of angiotensin-converting enzyme: cloning and functional expression as a captopril-insensitive carboxypeptidase. *J Biol Chem* 2000; 275: 33238-33243.
7. Hamming I, Timens W, Bulthuis M L, Lely A T, Navis G, van Goor H. Tissue distribution of ACE2 protein, the functional receptor for SARS coronavirus. A first step in understanding SARS pathogenesis. *J Pathol* 2004; 203: 631-637.
8. Santos R A, Simoes e Silva A C, Maric C, Silva D M, Machado R P, de Buhr I, Heringer-Walther S, Pinheiro S V, Lopes M T, Bader M, Mendes E P, Lemos V S, Campagnole-Santos M J, Schultheiss H P, Speth R et al. Angiotensin-(1-7) is an endogenous ligand for the G protein-coupled receptor Mas. *Proc Natl Acad Sci USA* 2003; 100:8258-8263.
9. Li X, Molina-Molina M, Abdul-Hafez A, Uhal V, Xaubet A, Uhal B D. Angiotensin converting enzyme-2 is protective but downregulated in human and experimental lung fibrosis. *Am J Physiol Lung Cell Mol Physiol.* 2008; 295:L178-185.
10. Dai H L, Guo Y, Guang X F, Xiao Z C, Zhang M, Yin X L. The changes of serum angiotensin-converting enzyme 2 in patients with pulmonary arterial hypertension due to congenital heart disease. *Cardiology* 2013; 12:208-212.
11. Yamazato Y, Ferreira A J, Hong K H, Sriramula S, Francis J, Yamazato M, Yuan L, Bradford C N, Shenoy V, Oh S P, Katovich M J, Raizada M K. Prevention of pulmonary hypertension by angiotensin-converting enzyme-2 gene transfer. *Hypertension* 2009; 54:365-371.
12. Shenoy V, Ferreira A J, Qi Y, Fraga-Silva R A, Diez-Freire C, Dooies A, Jun J Y, Sriramula S, Mariappan N, Pourang D, Venugopal C S, Francis J, Reudelhuber T, Santos R A, Patel J M, et al. The angiotensin converting enzyme 2/angiotensin-(1-7)/Mas axis confers cardiopulmonary protection against lung fibrosis and pulmonary hypertension. *Am J Respir Crit Care Med* 2010; 182: 1065-1072.
13. Kleinsasser A, Pircher I, Treml B, Schwienbacher M, Schuster M, Janzek E, Loibner H, Penninger J M, Loeckinger A. Recombinant angiotensin-converting enzyme 2 suppresses pulmonary vasoconstriction in acute hypoxia. *Wilderness Environ Med* 2012; 23:24-30.
14. Ferreira A J, Shenoy V, Yamazato Y, Sriramula S, Francis J, Yuan L, Castellano R K, Ostrov D A, Oh S P, Katovich M J, Raizada M K. Evidence for angiotensin-converting enzyme 2 as a therapeutic target for the prevention of pulmonary hypertension. *Am J Respir Crit Care Med* 2009; 179:1048-1054.
15. Shenoy V, Gjymishka A, Jarajapu Y P, Qi Y, Afzal A, Rigatto K, Ferreira A J, Fraga-Silva R A, Kearns P, Douglas J Y, Agarwal D, Mubarak K K, Bradford C, Kennedy W R, Jun J Y, et al. Diminazene attenuates pulmonary hypertension and improves angiogenic progenitor cell functions in experimental models. *Am J Respir Crit Care Med* 2013; 187:648-657.
16. Ruhlman T, Verma D, Samson N, Daniell H. The role of heterologous chloroplast sequence elements in transgene integration and expression. *Plant Physiol* 2010; 152: 2088-2104.
17. Boyhan D, Daniell H. Low-cost production of proinsulin in tobacco and lettuce chloroplasts for injectable or oral delivery of functional insulin and C-peptide. *Plant Biotechnol J* 2011; 9: 585-598.
18. Kwon K C, Nityanandam R, New J S, Daniell H. Oral delivery of bioencapsulated exendin-4 expressed in chloroplasts lowers blood glucose level in mice and stimulates insulin secretion in beta-TC6 cells. *Plant Biotechnol J* 2013; 11:77-86.
19. Ruhlman T, Ahangari R, Devine A, Samsam M, Daniell H. Expression of cholera toxin B-proinsulin fusion protein in lettuce and tobacco chloroplasts-oral administration protects against development of insulitis in non-obese diabetic mice. *Plant Biotechnol J* 2007; 5:495-510.
20. Verma D, Moghimi B, LoDuca P A, Singh H D, Hoffman B E, Herzog R W, Daniell H. Oral delivery of bioencapsulated coagulation factor IX prevents inhibitor formation and fatal anaphylaxis in hemophilia B mice. *Proc Natl Acad Sci USA* 2010; 107:7101-7106.
21. Kwon K C, Verma D, Singh N D, Herzog R W, Daniell H. Oral delivery of human biopharmaceuticals, autoantigens and vaccine antigens bioencapsulated in plant cells. *Adv Drug Deliv Rev* 2013; 65:782-799.
22. Daniell H. Transgene containment by maternal inheritance: Effective or elusive? *Proc Natl Acad Sci USA* 2007; 104:6879-6880.
23. Daniell H, Singh N D, Mason H, Streatfield S J. Plant-made vaccine antigens and biopharmaceuticals. *Trends Plant Sci* 2009; 14:669-679.
24. Lakshmi P S, Verma D, Yang X, Lloyd B, Daniell H. Low cost tuberculosis vaccine antigens in capsules: expression in chloroplasts, bio-encapsulation, stability and functional evaluation in vitro. *PLoS ONE* 2013; 8:e54708.
25. Zimran A, Brill-Almon E, Chertkoff R, Petakov M, Blanco-Favela F, Muñoz E T, Solorio-Meza S E, Amato D, Duran G, Giona F, Heitner R, Rosenbaum H, Giraldo P, Mehta A, Park G, et al. Pivotal trial with plant-cell-expressed recombinant glucocerebrosidase, taliglucerase alfa, a novel enzyme replacement therapy for Gaucher disease. *Blood* 2011; 118:5767-5773.
26. Verma D, Samson N P, Koya V, Daniell H. A protocol for expression of foreign genes in chloroplasts. *Nat Protoc* 2008; 3:739-758.
27. Zhang R G, Westbrook M L, Westbrook E M, Scott D L, Otwinowski Z, Maulik P R, Reed R A, Shipley G G. The 2.4 Å crystal structure of cholera toxin B subunit pentamer: choleragenoid. *J Mol Biol* 1995; 251:550-562.
28. Long L, Yang X, Southwood M, Lu J, Marciniak S J, Dunmore B J, Morrell M W. Chloroquine prevents progression of experimental pulmonary hypertension via inhibition of autophagy and lysosomal bone morphogenetic protein type II receptor degradation. *Circ Res* 2013; 112:1159-1170.
29. Santos R A, Ferreira A J, Nadu A P, Braga A N, de Almeida A P, Campagnole-Santos M J, Baltatu O, Iliescu R, Reudelhuber T L, Bader M. Expression of an angio- 29. tensin-(1-7)-producing fusion protein produces cardioprotective effects in rats. *Physiol Genomics* 2004; 17:292-299.
30. Ruiz O N, Alvarez D, Torres C, Roman L, Daniell H. Metallothionein expression in chloroplasts enhances mercury accumulation and phytoremediation capability. *Plant Biotechnol J* 2011; 9:609-617.
31. Mager I, Roberts T C, Wood M J, El Andaloussi, S. From gut to brain: bioencapsulated therapeutic protein reduces amyloid load upon oral delivery. *Mol Ther* 2014; 22: 485-486.
32. Kohli N, Westerveld D R, Ayache A C, Verma A, Shil P, Prasad T, Zhu P, Chan S L, Li Q, Daniell H. Oral delivery of bioencapsulated proteins across blood-brain and blood-retinal barriers. *Mol Ther* 2014; 22: 535-546.
33. Morton B R. Chloroplast DNA codon use: Evidence for selection at the psbA locus based on tRNA availability. *J Mol Evol* 1993; 37:273-280.
34. Karlin S, Mrazek J. What drives codon choices in human genes? *J Mol Biol* 1996; 262:459-472.
35. De Cosa B, Moar W, Lee S B, Miller M, Daniell H. Overexpression of the Bt cry2Aa2 operon in chloroplasts leads to formation of insecticidal crystals. *Nat Biotechnol* 2001; 19:71-74.
36. Daniell H, Ruiz G, Denes B, Sandberg L, Langridge W. Optimization of codon composition and regulatory elements for expression of human insulin like growth factor-1 in transgenic chloroplasts and evaluation of structural identity and function. *BMC Biotechnol* 2009; 9:23.
37. Arlen P A, Falconer R, Cherukumilli S, Cole A, Cole A M, Oishi K K, Daniell H. Field production and functional evaluation of chloroplast-derived interferon-alpha2b. *Plant Biotechnol J* 2007; 5:511-525.
38. Verma D, Moghimi B, LoDuca P A, Singh H D, Hoffman B E, Herzog R W, Daniell H. Oral delivery of bioencapsulated coagulation factor IX prevents inhibitor formation and fatal anaphylaxis in hemophilia B mice. *Proc Natl Acad Sci USA* 2010; 107:710-716.
39. Hill D R, Ford L, Lalloo D G. Oral cholera vaccines: use in clinical practice. *Lancet Infect Dis* 2006; 6:361-73.
40. Stanford M, Whittall T, Bergmeier L A, Lindblad M, Lundin S, Shinnick T, Mizushima Y, Holmgren J, Lehner T. Oral tolerization with peptide 336-351 linked to cholera toxin B subunit in preventing relapses of uveitis in Behcet's disease. *Clin Exp Immunol* 2004; 137:201-208.
41. Sun J B, Czerkinsky C, Holmgren J. Mucosally induced immunological tolerance, regulatory T Cells and the adjuvant effect by cholera toxin B subunit. *Scand J Immunol* 2010; 71:1-11.
42. Wilson J P. Surface area of the small intestine in man. *Gut* 1967; 8:618-621.
43. Holmgren J, Lönnroth I, Månsson J, Svennerholm L. Interaction of cholera toxin and membrane GM1 ganglioside of small intestine. *Proc Natl Acad Sci USA* 1975; 72:2520-2524.
44. Fishman P H, Bradley R M, Hom B E, Moss J. Uptake and metabolism of exogenous gangliosides by cultured cells: effect of choleragen on the turnover of GM1. *J Lipid Res* 1983; 24:1002-1011.
45. Yamada K, Iyer S N, Chappell M C, Ganten D, Ferrario C M. Converting enzyme determines plasma clearance of angiotensin-(1-7). *Hypertension* 1998; 32:496-502.
46. Allred A J, Diz D I, Ferrario C M, Chappell M C. Pathways for angiotensin-(1-7) metabolism in pulmonary and renal tissues. *Am J Physiol Renal Physiol* 2000; 279:F841-850.
47. Duckert P, Brunak S, Blom N. Prediction of protein convertase cleavage sites. *Protein Eng Des Sel* 2004; 17:107-112.
48. Bradford C N, Ely D R, Raizada M K. Targeting the vasoprotective axis of the renin-angiotensin system: a novel strategic approach to pulmonary hypertensive therapy. *Curr Hypertens Rep* 2010; 12:212-219.
49. Oudit G Y, Liu G C, Zhong J, Basu R, Chow F L, Zhou J, Loibner H, Janzek E, Schuster M, Penninger J M, Herzenberg A M, Kassiri Z, Scholey J W. Human recombinant ACE2 reduces the progression of diabetic nephropathy. *Diabetes* 2010; 59:529-538.
50. Zou Z, Yan Y, Shu Y, Gao R, Sun Y, Li X, Ju X, Liang Z, Liu Q, Zhao Y, Guo F, Bai T, Han Z, Zhu J, Zhou H, et al. Angiotensin-converting enzyme 2 protects from lethal avian influenza A H5N1 infections. *Nat Commun* 2014; 5:3594
51. Zhong J, Guo D, Chen C B, Wang W, Schuster M, Loibner H, Penninger J M, Scholey J W, Kassiri Z, Oudit G Y. Prevention of angiotensin II-mediated renal oxidative stress, inflammation, and fibrosis by angiotensin-converting enzyme 2. *Hypertension* 2011; 57(2):314-322.
52. Wagenaar G T, Laghmaniel H, Fidder M, Sengers R M, de Visser Y P, de Vries L, Rink R, Roks A J, Folkerts G, Walther F J, Agonists of MAS oncogene and angiotensin II type 2 receptors attenuate cardiopulmonary disease in rats with neonatal hyperoxia-induced lung injury. *Am J Physiol Lung Cell Mol Physiol* 2013; 305:L341-351.
53. Dorfmüller P, Perros F, Balabanian K, Humbert M. Inflammation in pulmonary arterial hypertension. *Eur Respir J* 2003; 22:358-363.
54. Freemann E J, Chisolm G M, Ferrario C M, Tallant E A. Angiotensin-(1-7) inhibits vascular smooth muscle cell growth. *Hypertension* 1996; 28:104-108.
55. Velkoska E, Dean R G, Griggs K, Burchill L, Burrell L M. Angiotensin-(1-7) infusion is associated with increased blood pressure and adverse cardiac remodelling in rats with subtotal nephrectomy. *Clin Sci (Lond)* 2011; 120:335-345.
56. Grobe J L, Mecca A P, Mao H, Katovich M J. Chronic angiotensin-(1-7) prevents cardiac fibrosis in DOCA-salt model of hypertension. *Am J Physiol Heart Circ Physiol* 2006; 290:H2417-H2423.
57. Grobe J L, Mecca A P, Lingis M, Shenoy V, Bolton T A, Machado J M, Speth R C, Raizada M K, Katovich M J. Prevention of angiotensin II-induced cardiac remodeling by angiotensin-(1-7). *Am J Physiol Heart Circ Physiol* 2007; 292:H736-H742.
58. Simon M A. Assessment and treatment of right ventricular failure. *Nat Rev Cardiol* 2013; 10:204-218.

Example 2

Oral Delivery of ACE2/Ang-(1-7) Bioencapsulated in Plant Cells Protects Against Experimental Uveitis and Autoimmune Uveoretinitis The following materials and methods are provided to facilitate the practice of Example II.

Chloroplast Transformation Vector Construction and Regeneration of Transplastomic Lines Performed as described above in Example I.

Animals and Experimental Procedures

Wild-type C57Bl/6J mice (6-8 weeks old)) and B10.RIII mice (8-10 weeks old) were purchased from Jackson Laboratories (Bar Harbor, Me.) and maintained at the Animal Care Service at the University of Florida. All procedures adhered to the ARVO statement for the use of Animals in Ophthalmic and Vision Research, and the protocol was approved by the Animal Care and Use Committee of the University of Florida. The animals were fed standard laboratory chow and allowed free access to water in an air-conditioned room with a 12-12-hr light dark cycle.

The mice were divided in three groups for EIU model and orally gavaged with control (untransformed wild-type, WT) tobacco leaves, CTB-ACE2, and CTB-Ang-(1-7) expressing transplastomic tobacco leaves. The mice were given ~500 mg of the specified tobacco leaf material suspended in sterile PBS, by careful gavage into the hypopharynx twice in a day for 5 days. For preparation of the gavage material, leaves were frozen and ground in liquid nitrogen. EIU was induced by a single intravitreal injection of *Escherichia coli* LPS (25 ng/eye) (Sigma-Aldrich, Inc., St. Louis, Mo.) dissolved in sterile pyrogen-free saline, on the fifth day of feeding. All animals were anesthetized and pupils were dilated before intraocular injections. Each experimental group included at least 4-6 animals and each experiment was performed at least twice.

For the EAU model, the mice were divided in three groups and orally gavaged with ~500 mg of the control wild-type tobacco leaves, CTB-ACE2, CTB-Ang-(1-7) expressing transplastomic tobacco leaves once daily for 15 days. EAU was induced by active immunization with ~50 μg of IRBP (161-180) (SGIPYIISYLHPGNTILHVD) (Genscript, Piscataway, N.J.) with CFA (Sigma-Aldrich, Inc., St. Louis, Mo.) (1:1 vol/vol) subcutaneously, on the second day of feeding. Each experimental group included at least 4-6 animals and each experiment was performed at least twice to ensure reproducibility.

Different Doses of Lyophilized CTB-ACE2 Plant Cell Oral Gavage and Induction of EIU In another approach, the mice were divided in three groups and orally gavaged with varying dosage of lyophilized CTB-ACE2 expressing transplastomic tobacco leaves. The mice were given 12.5 mg, 25 mg and 50 mg of the specified lyophilized plant cells suspended in sterile PBS, by careful gavage into the hypopharynx once in a day for 4 days EIU was induced by a single intravitreal injection of *Escherichia coli* LPS (25 ng/eye) (Sigma-Aldrich, Inc., St. Louis, Mo.) dissolved in sterile pyrogen-free saline, on the fourth day of feeding. All animals were anesthetized and pupils were dilated before intraocular injections. Each experimental group included at least 4-6 animals and each experiment was performed at least twice.

Delaying of Oral Gavage and Induction of EAU

The mice were divided in three groups and orally gavaged with ~50 mg of the lyophilized plant cells expressing CTB-Ang-(1-7) once daily. The treatment with CTB-Ang-(1-7) started at day 5 and day 10 after IRBP injection to induce EAU, and continued daily till day 14. EAU was induced by active immunization with ~50 μg of IRBP (161-180) (SGIPYIISYLHPGNTILHVD; SEQ ID NO: 22) (Genscript, Piscataway, N.J.) with CFA (Sigma-Aldrich, Inc., St. Louis, Mo.) (1:1 vol/vol) subcutaneously. Each experimental group included at least 4-6 animals and each experiment was performed at least twice to ensure reproducibility.

Histopathological Evaluation

The EIU mice were euthanized 24 hr after LPS injection and the eyes were enucleated immediately and fixed in 4% paraformaldehyde freshly made in PBS overnight at 4° C. and processed for paraffin embedding and sections. Sagittal sections (4 μm) from every 50 μm were cut and stained with hematoxylin and eosin (H&E). The anterior and posterior chambers were examined under light microscope and the infiltrating inflammatory cells were counted in a masked fashion. The number of infiltrating inflammatory cells in five sections per eye was averaged and recorded. EIU clinical data shown were representatives of three sets of experiments.

The EAU mice were euthanized and the eyes were harvested on 14th day after immunization, followed by fixation, paraffin embedment and stained with H&E. The severity of EAU was evaluated in a masked fashion on a scale of 0-4 using previously published criteria based on the number, type and size of lesions [32] and the inflammatory cells were counted as described above. EAU clinical data shown were representatives of two sets of experiments, 5 animals each experimental group.

ACE2 Activity Assay

Representative retinas from each group of mice were dissected and homogenized by sonication in ACE2 assay buffer. The ACE2 activity assay was performed using 100 μg of retinal protein in black 96-well opaque plates with 50 μM ACE2-specific fluorogenic peptide substrate VI (R&D Systems, Inc., Minneapolis, Minn.) in a final volume of 100 μl per well reaction mixture. The enzymatic activity was recorded in a SpectraMax M3 fluorescence microplate reader (Molecular Devices, LLC, Sunnyvale, Calif.) for 2 hr with excitation at 340 nm and emission at 400 nm as described previously [10]. For the sera samples, 10 μl sera were used in a 100 μl reaction. All measurements were performed in duplicate and the data represent the mean of three assay results.

Ang-(1-7) Estimation by Enzyme Immunoassay (EIA)

The level of Ang-(1-7) in plasma and retina were measured using a commercial EIA kit (Bachem, San Carlos, Calif.), according to the manufacturer's instructions. All measurements were performed in duplicate and the data represent the mean of two separate assay results.

Real Time RT-PCR Analysis

Total RNA was isolated from freshly enucleated eyes using Trizol Reagent (Invitrogen, Carlsbad, Calif.) according to manufacturer's instructions. Reverse transcription was performed using Enhanced Avian HS RT-PCR kit (Sigma-Aldrich, Inc., St. Louis, Mo.) following manufacturer's instructions. Real time PCR was carried out on real time thermal cycler (iCycler, Bio-Rad Life Sciences, Hercules, Calif.) using iQTM Sybr Green Supermix (Bio-Rad Life Sciences, Hercules, Calif.). The threshold cycle number (Ct) for real-time PCR was set by the cycler software. Optimal primer concentration for PCR was determined separately for each primer pair. Each reaction was run in duplicate or in triplicate, and reaction tubes with target primers and those with Actin primers were always included in the same PCR run. To test the primer efficiencies, the one-step reverse-transcriptase-PCR was run with each target primer. Relative quantification was achieved by the comparative $2^{-\Delta\Delta Ct}$ method 1. The relative increase/decrease of mRNA target X in the experimental group (EG) was calculated using the control group as the calibrator: $2^{-\Delta\Delta Ct}$, where $\Delta\Delta$ Ct is {Ct.x [EG]−Ct. Actin [EG]}−{Ct.x [control]−Ct. Actin [control]}. Primer sequences used in this study are shown in Table 1. All the reactions were repeated at least twice.

TABLE 1

Primers used for Real-Time RT-PCR analysis

| Gene name | Accession number | Sequences | | |
|---|---|---|---|---|
| Interleukin-6 | NM_031168.1 | Forward: | 5'-TCGGCAAACCTAGTGCGTTA-3' | (4)* |
| | | Reverse: | 5'-CCAAGAAACCATCTGGCTAGG-3' | (5) |
| IL-1β | NM_008361.3 | Forward: | 5'-AAAGCCTCGTGCTGTCGGACC-3' | (6) |
| | | Reverse: | 5'-CAGCTGCAGGGTGGGTGTGC-3' | (7) |
| TNF-α | NM_013693.2 | Forward: | 5'-AGGCGCCACATCTCCCTCCA-3' | (8) |
| | | Reverse: | 5'-CGGTGTGGGTGAGGAGCACG-3' | (9) |
| ICAM-1 | NM_010493 | Forward: | 5'-AGATGACCTGCAGACGGAAG-3' | (10) |
| | | Reverse: | 5'-GGCTGAGGGTAAATGCTGTC-3' | (11) |
| MCP-1 | NM_011333 | Forward: | 5'-CCCCACTCACCTGCTGCTACT-3' | (12) |
| | | Reverse: | 5'-GGCATCACAGTCCGAGTCACA-3' | (13) |
| β-Actin | X03672 | Forward: | 5'-AGCAGATGTGGATCAGCAAG-3' | (14) |
| | | Reverse: | 5'-ACAGAAGCAATGCTGTCACC-3' | (15) |
| MAS receptor | NM_008552 | Forward: | 5'-AGGGTGACTGACTGAGTTTGG-3' | (16) |
| | | Reverse: | 5'-GAAGGTAAGAGGACAGGAGC-3' | (17) |
| AT1Ra | NM_177322 | Forward: | 5'-ATCGGACTAAATGGCTCACG-3' | (18) |
| | | Reverse: | 5'-ACGTGGGTCTCCATTGCTAA-3' | (19) |
| AT1Rb | AK087228 | Forward: | 5'-AGTGGAGTGAGAGGGTTCAA-3' | (20) |
| | | Reverse: | 5'-GGGCATTGAAGACATGGTAT-3' | (21) |

*Numbers in parentheses are SEQ ID NOS.

Fundus Imaging and Assessment of EAU

Fundus assessment of EAU was performed at day 14 after EAU induction. The pupils were dilated using atropine sulfate and phenylephrine hydrochloride. The mice were anesthetized by intraperitoneal injection of ketamine (75 mg/kg) and xylazine (5 mg/kg) mixture, and Gonak Hypromellose demulcent ophthalmic solution (Akorn, Inc., Buffalo Grove, Ill.) was used on ocular surface. The fundus was imaged using the Micron II small animal retinal imaging AD camera (Phoenix Research Laboratories, Pleasanton, Calif.). Eyes were examined for vasculitis, focal lesions, linear lesions, retinal hemorrhages and retinal detachment. Clinical EAU scoring was performed on a scale of 0-4, as described in detail previously [31]. EAU clinical data shown was representative of two sets of experiments.

Spectral Domain Optical Coherence Tomography (SD-OCT) Imaging and Assessment of EAU Mice Mice were anesthetized and the pupil dilated as described above. Artificial tears (Systane Ultra, Alcon, Fort Worth, Tex.) were used throughout the procedure to maintain corneal moisture and clarity. SD-OCT images were obtained in mice on 14th day after immunization using the Bioptigen Spectral Domain Ophthalmic Imaging System (Bioptigen, Inc., Durham, N.C.). Images acquired by the software provided from the company. The average single B scan and volume scans were obtained with images centered on optic nerve head. The retinal thickness was measured from five frames of the volume of OCT images and averaged from the intensity peak of boundary corresponding to the vitreo-retinal interface to the intensity peak corresponding to the retinal pigmented epithelium [53]. EAU clinical data shown was representative of two sets of experiments.

Statistical Analysis

Data are expressed as the mean+SD of at least two independent experiments. Differences between mean values of multiple groups were analyzed by one-way analysis of variance with Dunnett's test for post hoc comparisons. A p-value less than 0.05 was considered statistically significant.

Results

Hyperactivity of the renin-angiotensin system (RAS) resulting in elevated Angiotensin II (Ang II) contributes to all stages of inflammatory responses including ocular inflammation. The discovery of angiotensin-converting enzyme 2 (ACE2) has established a protective axis of RAS involving ACE2/Ang-(1-7)/Mas that counteracts the proinflammatory and hypertrophic effects of the deleterious ACE/AngII/AT1R axis. In the present example, we demonstrate that enhancing the systemic and local activity of the protective axis of the RAS by oral delivery of ACE2 and Ang-(1-7) bioencapsulated in plant cells confers protection against ocular inflammation. Both ACE2 and Ang-(1-7), fused with the non-toxic cholera toxin subunit B (CTB) were expressed in plant chloroplasts as described in Example I. In the present example, we show that increased levels of ACE2 and Ang-(1-7) were observed in circulation and retina after oral administration of CTB-ACE2/Ang-(1-7) expressing plant cells. Oral feeding of mice with bioencapsulated ACE2 or Ang-(1-7) significantly reduced endotoxin-induced uveitis (EIU) in mice. Treatment with bioencapsulated ACE2 or Ang-(1-7) also dramatically decreased cellular infiltration, retinal vasculitis, damage and folding in experimental autoimmune uveoretinitis (EAU). Thus, enhancing the protective axis of RAS by oral delivery of ACE2/Ang-(1-7) bioencapsulated in plant cells provide an innovative, highly efficient and cost-effective therapeutic strategy for ocular inflammation such as EIU and EAU.

The ability to deliver drugs efficiently to the retina or the brain remains a key challenge due to anatomic barriers and physiological clearance mechanisms [13]. The Plant chloroplast genetic engineering system to express therapeutic proteins is emerging as a highly efficient, cost-effective approach for therapeutic interventions of many pathologic conditions [12, 14]. In contrast to current protein production systems (mammalian, yeast, or bacteria), the transplastomic system requires no complex production/purification steps [14]. Current biopharmaceuticals are not affordable to more than half of the global population because of use of prohibitively expensive production, purification and delivery systems [14]. However, chloroplasts produce the same biopharmaceuticals at a significantly lower cost by eliminating fermentation, purification, cold chain and sterile delivery systems. Such cGMP facilities to produce plants for human clinical studies are already in use in the US (e.g. Fraunhofer, Del., Kentucky Bioprocessing, etc.). Ultimately, the therapeutic proteins will be provided to patients as capsules after lyophilization of plant cells, facilitating prolonged storage at room temperature. In addition, bioencapsulation of therapeutic proteins within plant cell walls enable oral delivery by their protection in the digestive system [14,15]. The bioencapsulated proteins that pass through the stomach are released in the intestine with the aid of commensal bacteria [16,17]. Bacteria inhabiting the human gut have evolved to utilize complex carbohydrates in plant cell wall and are capable of utilizing almost all of plant glycans. So the gut microbes recognize, import, and digest plant cell wall consisting of cellulose, hemicellulose, and pectin. Up to 10% daily energy is obtained from polysaccharide fiber via the symbiotic bacteria living in human gut. These polysaccharides are broken down to sugars and fermented to short fatty acids then absorbed by human gut. Therapeutic proteins enter circulation by receptor monosialotetrahexosylganglioside (GM1) mediated delivery when fused with the non-toxic subunit B of cholera toxin (CTB) as the transmucosal carrier [14,18-22]. The use of CTB as a transmucosal carrier can facilitate the transportation of conjugated proteins into circulation through its strong binding to GM1 because large mucosal area of human intestine (approximately 1.8-2.7 m2 [23] facilitates CTB to bind an intestinal epithelium cell up to a maximum of 15,000 CTB [24] and the rapid turnover of cell-associated GM1 receptor on the cell [25]. Furthermore, the GM1 gangliosides receptors are also found in the plasma membranes of most cells, particularly most abundant in the nervous system and retina [26], allowing efficient uptake of CTB fusion protein in the brain and retinal cells as observed in our recent study [12]. Considering the proven anti-inflammatory actions of ACE2 and Ang-(1-7) and the ability of CTB to cross the epithelial barrier and facilitate neuronal uptake, we hypothesized that oral delivery of ACE2 and Ang-(1-7) fused with CTB bioencapsulated in plant cells will enhance both systemic and local activity of the protective axis of RAS and confer protection against ocular inflammation. In this example, we tested this hypothesis in two mouse models of ocular inflammation. We observed that oral administration of CTB-ACE2/Ang-(1-7) bioencapsulated in plant cells reduced ocular inflammation in both EIU and EAU models, providing proof-of-concept that enhancing the protective axis of RAS by oral delivery of ACE2/Ang-(1-7) bioencapsulated in plant cells provides an innovative, highly efficient and cost-effective therapeutic strategy for ocular inflammation such as uveitis and auto-immune uveoretinitis.

Results

Creation of Transplastomic Plants Expressing CTB-ACE2/-Ang-(1-7)

The CTB-fused therapeutic genes were cloned into the chloroplast transformation vector, pLD. The hinge site (FIG. 1) was introduced between CTB and therapeutic proteins to avoid steric hindrance and facilitate formation of pentameric structure of CTB fused to therapeutic proteins, when expressed in chloroplasts. Pentameric structure of CTB plays a critical role in translocating fusion proteins into epithelial cells via the GM1 receptor. Furin cleavage site (FIG. 1a) facilitates release of therapeutic proteins from CTB after transmucosal delivery. The furin protease is ubiquitously present in all cell and tissue types and the consensus cleavage site is well characterized [27]. The introduction of the consensus furin cleavage site between CTB and fused proteins will ensure efficient release of the therapeutic proteins from CTB into the circulation. For the site-specific integration of the CTB-ACE2/-Ang-(1-7) expression cassette into chloroplast genome, the cassette was flanked by trnI and trnA sequence, which are homologous to endogenous chloroplast sequence. Light regulated strong chloroplast promoter, PsbA, was used to express the fusion gene. To screen chloroplast transformants, aminoglycoside 3'-adenylyltransferase gene (aadA) was driven under the control of ribosomal rRNA promoter (Prrn) to disarm the inhibitory action of spectinomycin on chloroplast translation (FIG. 1). The sequence-confirmed chloroplast transformation vectors were bombarded onto leaves to create the transplastomic plants expressing CTB-ACE2 and CTB-Ang-(1-7), using biolistic particle delivery system. Shoots emerged from spectinomycin containing regeneration medium were investigated for the site specific integration of the expression cassette into the chloroplast genome, using PCR analysis. The specific primer sets were designed to amplify fragments in the size of ~1.65 kb with 3P/3M for both CTB-ACE2 and CTB-Ang-(1-7), ~4.5 and ~2.2 kb with 5P/2M for CTB-ACE2 and CTB-Ang-(1-7), respectively, and ~3.0 and ~1.1 kb with 5P/R for CTB-ACE2 and CTB-Ang-(1-7), respectively. Positive shoots displaying the expected right size fragments were subjected to two more rounds of tissue culture under antibiotic selection to achieve homoplasmy. The homoplasmic plants were confirmed by Southern blot analysis (data not shown), transferred and grown in a temperature- and humidity-controlled greenhouse. The expression level of CTB-fused therapeutic proteins of mature leaves was measured quantitatively using densitometry and Image J or ELISA with known amount of CTB proteins to generate the standard curve. The expression level was up to 2.14% and 8.7% of total leaf protein for CTB-ACE2 and CTB-Ang-(1-7) at their peak, respectively (data not shown). For consistency of batches between harvests, leaves were always harvested at 6 pm to maximize accumulation of therapeutic proteins expressed under the control of a light regulated promoter (psbA). Also, only mature leaves were chosen for harvest to maintain similar expression levels of the proteins between batches. While it is difficult to precisely control expression levels at the time of harvest, dosage is precisely determined after lyophilization and the same dose is delivered by varying the weight of lyophilized powder in each capsule or gavage.

Characterization of CTB-Fused Therapeutic Proteins Expressed in Chloroplasts

Figure 12A:
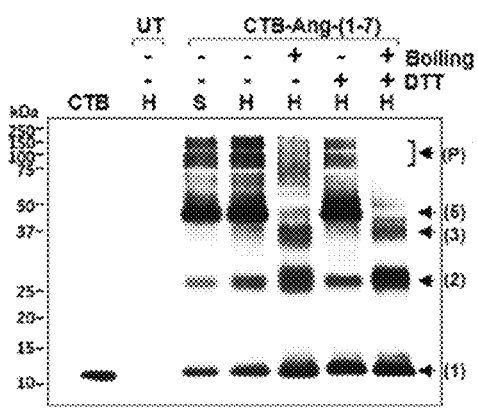
FIGS. 12A-12E. Evaluation of proper formation of pentameric structure and lyophilization for the CTB fusion proteins.

CTB was used as a carrier to allow therapeutic proteins to pass through both epithelial and blood-retinal barrier [12], which is mediated by the interaction between pentameric CTB and GM1 receptor. To investigate the proper folding and assembly of the pentameric structure of CTB-fused therapeutic proteins in chloroplasts, western blot analysis was performed with CTB-Ang-(1-7). Proteins were extracted under non-denaturing conditions, followed by either treatment with or without denaturing agents, prior to separation on SDS-acrylamide gel. There was negligible change in polypeptide profile oligomeric structures of CTB-Ang-(1-7) when protein was treated with DTT alone (FIG. 12a). In contrast, boiling samples showed dramatic change in polypeptide patterns (FIG. 12a). This is consistent with the previous studies on dissociation of CTB pentameric structure [28]. Multiple interactions between CTB monomers, such as 30 hydrogen bonds, 7 salt bridges and hydrophobic interactions, make pentameric structure of CTB highly resistant to the dissociation so the pentamer structure is not affected by denaturants such as SDS and DTT. However, the structure can be dissociated by using heat energy. This could be due to the difference in accessibility of denaturing agents to their targets. The access of DTT to the intramolecular disulfide bond of monomer is not easy unless pentameric structure dissociates first, due to the intimate interactions between monomers described above. As expected, both denaturing agents showed no high molecular weight oligomers (pentamer-pentmer interactions), but dimeric and monomeric forms of CTB-Ang-(1-7) were observed (FIG. 12a). The intramolecular disulfide bond of CTB monomer was easily disrupted by DTT after boiling than either boiling alone or DTT alone (FIG. 12a). Boiling allowed easy access of DTT to the internal disulfide bond by breaking intimate interactions between CTB monomers (hydrogen bonds and salt bridges) (FIG. 12a). From these results, it is evident that the disulfide bond of CTB-Ang-(1-7) monomer was properly formed and the interactions between the monomers of pentameric structure of CTB-Ang-(1-7) were well established in chloroplasts.

Figure 12B:
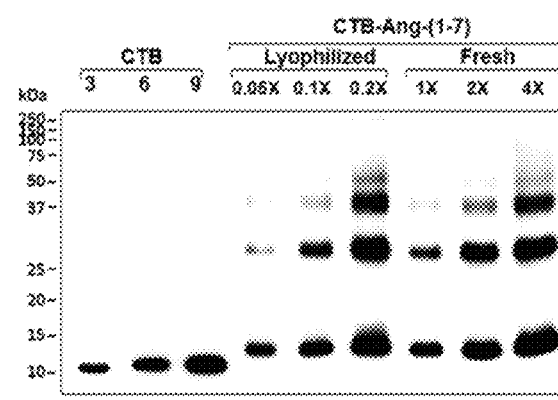
Figure 12C:
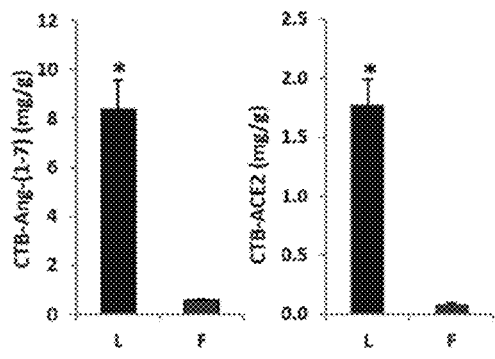
Figure 12D:
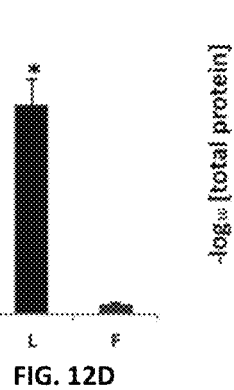

For clinical application, long-shelf life and stability of therapeutic protein expressed in plants are very important for successful and cost-effective treatment. Therefore, lyophilized CTB-fused therapeutic protein leaves were fully characterized. The weight of lyophilized leaf is usually reduced by 90% to 95% as a result of removal of water from plant cells, leading to more total protein per mg of leaf powder. Extraction of concentrated proteins from lyophilized leaf materials needs more volume of the extraction buffer because the amount of water lost in the process of lyophilization is slowly reabsorbed by the dried materials. For quantitation of lyophilized leaf materials, 10 mg of lyophilized powered leaf materials were resuspended in 300 µl extraction buffer in contrast to 100 mg of fresh leaf materials in the same volume of extraction buffer. Then the extracted total proteins were used for quantification for comparison between fresh and lyophilized leaf materials. Western blot analysis of the CTB-Ang-(1-7) showed that the band patterns between fresh and 3-month old lyophilized leaf materials were identical (FIG. 12b), confirming stability during lyophilization and prolonged storage at room temperature. As seen in the blot, twenty-time less lyophilized protein sample loaded showed similar band intensities to fresh leaf proteins (FIG. 12b). The quantity of CTB-Ang1-7 in fresh and lyophilized leaves was measured using immunoblots (FIG. 12b) and Image J software; the quantity of CTB-Ang-(1-7) increased 14.3 times in lyophilized leaves when compared to fresh leaves (FIG. 12c). The lyophilized CTB-ACE2 leaves showed 20.5 fold more CTB-Ace2 than fresh leaves when quantified using ELISA (FIG. 12d).

Figure 12E:
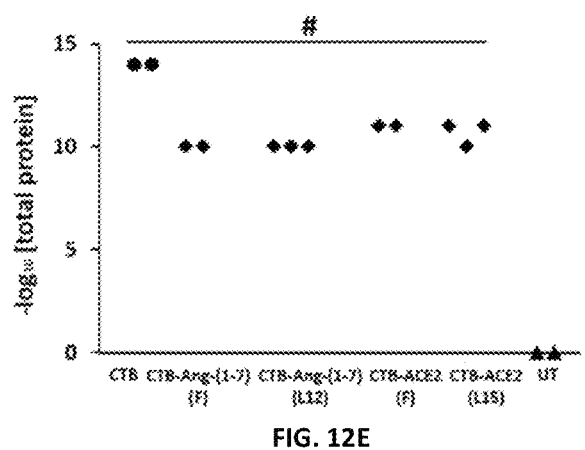

In this study, we observed that there was no damage or loss of the fusion protein (FIG. 12b) under the optimized lyophilization conditions. Moreover, the intactness of the pentameric structure of the lyophilized CTB-fused proteins was well preserved up to 15 months at room temperature, as confirmed in GM1 binding assay which showed binding affinity of the lyophilized CTB-fused proteins to GM1 as compared to respective positive control, CTB (FIG. 12e). Taken together, the homoplasmic transplastomic plants expressing CTB-ACE2 and -Ang-(1-7) were created and the fusion protein was properly expressed, folded, and assembled in chloroplasts. The folding, assembly and functionality of therapeutic proteins were well preserved in lyophilized leaves.

Figure 13A:
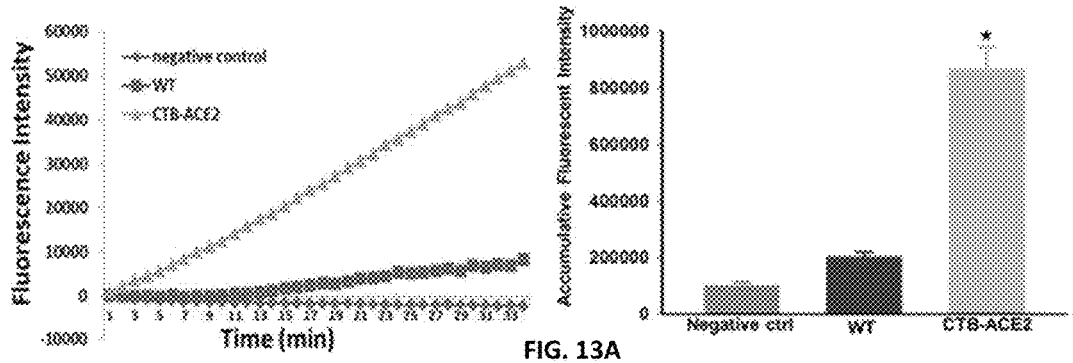
FIGS. 13A-13D. ACE2 activity assay using protein samples extracted from CTB-ACE2 transplastomic and untransformed leaf materials (WT).
Figure 13B:
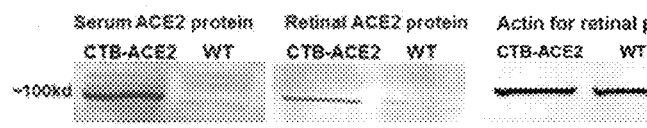
Figure 13C:
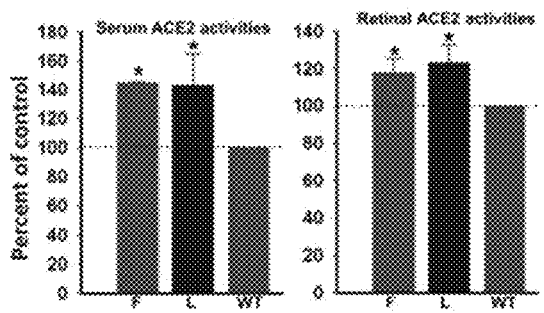
Figure 13D:
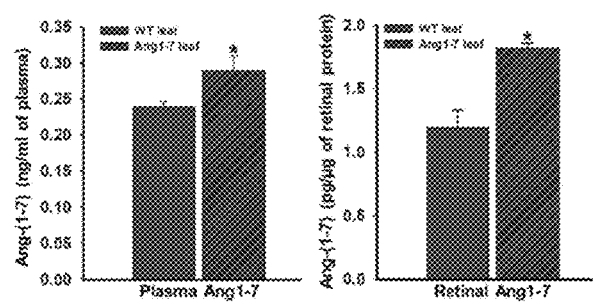

ACE2 activity assay using protein extracts isolated from plant leaves showed that plant cell expressed human ACE2 is enzymatically active (FIG. 13a). To investigate the in vivo potential of CTB-ACE2 and CTB-Ang-(1-7) to cross the intestinal barrier and tissue uptake, wild type C57Bl/6J mice were fed with either fresh (F, ~500 mg/mouse), or ten-fold less lyophilized (L, ~50 mg/mouse) CTB-ACE2, or control untransformed (WT) leaf materials for three days, mice were sacrificed at 5 hr after the last gavage. Circulatory and retinal ACE2 and Ang-(1-7) levels were measured by ACE2 activity assay, EIA and Western blotting (FIG. 13). ACE2 protein can be detected in both serum and retina 5 hours after oral gavage (FIG. 13b). Oral administration of either fresh frozen (F) or lyophilized (L) CTB-ACE2 transgenic leaf materials resulted in an increase of approximately 40% and >20% in ACE2 enzymatic activity in serum and retina, respectively when compared to WT leaf fed mice (FIG. 13c). There was a 15% increase in plasma and nearly 50% increase in Ang-(1-7) peptide level in the retina in CTB-Ang-(1-7) expressed leaf material fed group, detected by Ang-(1-7) specific EIA kit (FIG. 13d).

Figure 14A:
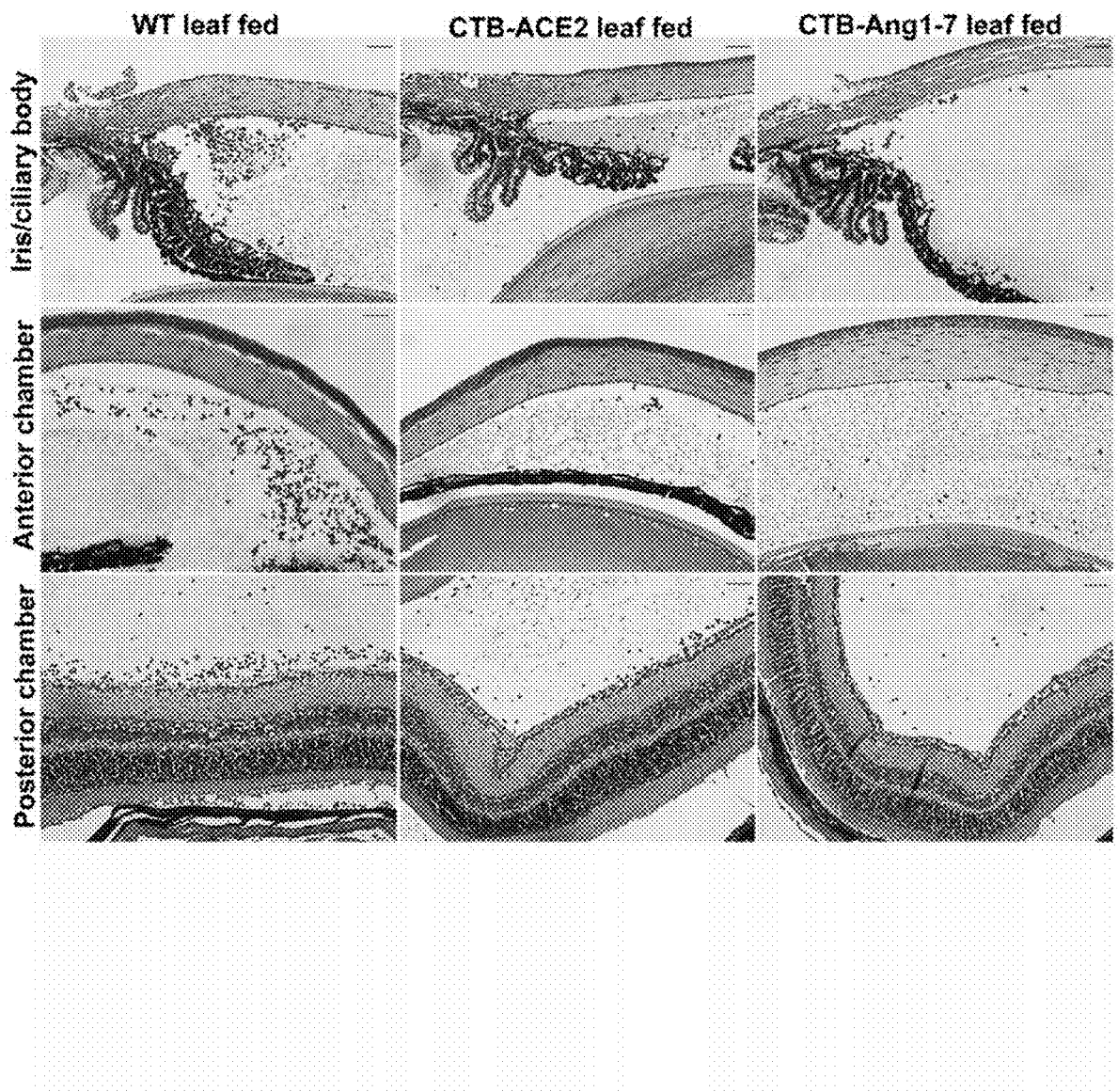
FIGS. 14A-14C. Histological evaluation of EIU mice. The mice were orally administered with Wild-type, CTB-ACE2 and CTB-Ang-(1-7) expressed leaf material for five days before LPS (25 ng/eye) injection. Eyes were enucleated 24 hr after LPS injection, fixed and processed for paraffin sections and stained with H&E.
Figure 14B:
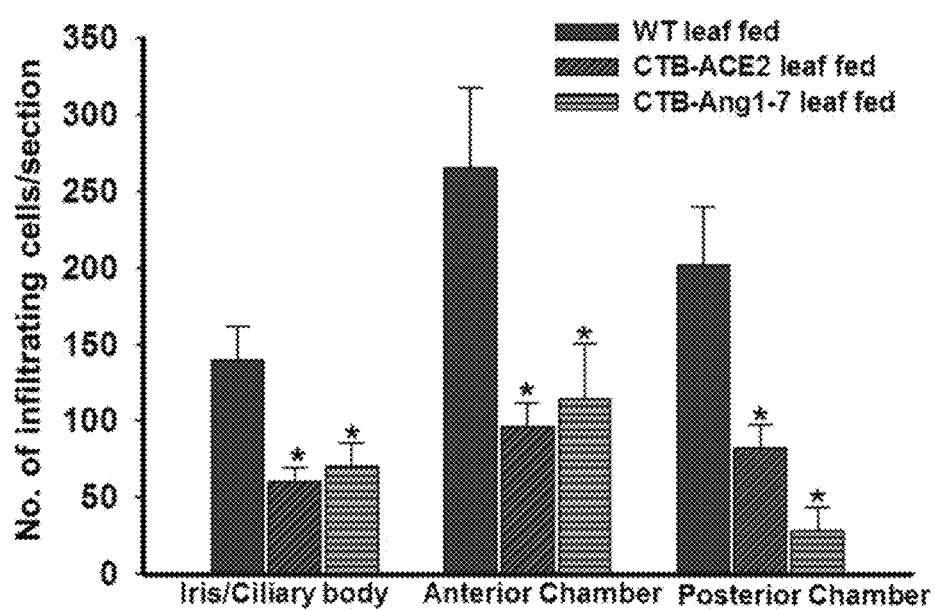

Oral Administration of Bioencapsulated CTB-ACE2 and CTB-Ang-(1-7) Reduced the Infiltration of Inflammatory Cells Induced by EIU We next examined the effects of ACE2 and Ang-(1-7) on endotoxin-induced infiltration of inflammatory cells such as leucocytes and monocytes in the iris, ciliary body, anterior chamber, and posterior chamber of the eye. Sagittal sections were stained with H&E and examined under bright field microscope. The histological evaluation of LPS injected eyes from mice fed with WT leaf revealed severe signs of uveitis with massive infiltration of inflammatory cells into the iris and ciliary body (ICB) (140±21 cells/section), anterior chamber (265±52 cells/section) and the posterior chamber (202±37 cells/section) (FIG. 14). Prophylactic treatment with CTB-ACE2 showed significantly diminished uveitis and reduced number of inflammatory cells into the ICB (60±09 cells/section), anterior chamber (96±15 cells/section) and also into the posterior chamber (82±15 cells/section). Similar results were observed in ICB (70±15 cells/section), anterior chamber (114±36 cells/section) and the posterior chamber (28±15 cells/section) when animals pretreated with CTB-Ang-(1-7) expressed leaf material (FIG. 14).

Figure 14C:
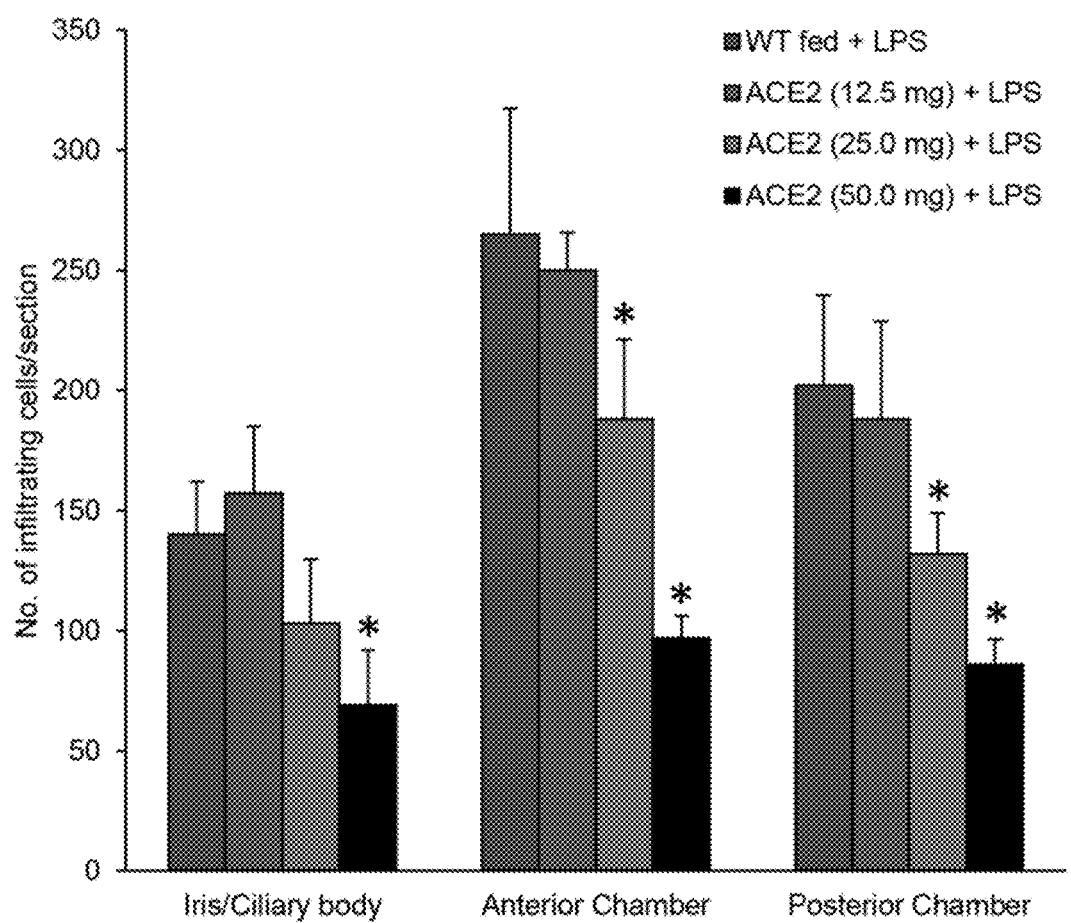

The therapeutic effect of different doses of CTB-ACE2 in EIU was evaluated using lyophilized leaf materials. Oral feeding of lyophilized CTB-ACE2 at 50 mg/day significantly prevented inflammatory cell infiltration into the iris and ciliary body, anterior chamber and posterior chamber to the same extent as the fresh leaf material at 500 mg/day; CTB-ACE2 feeding at 25 mg/day had moderate but significant protection, whereas 12.5 mg/day did not show any protective effect in EIU (FIG. 14C).

Figure 15A:
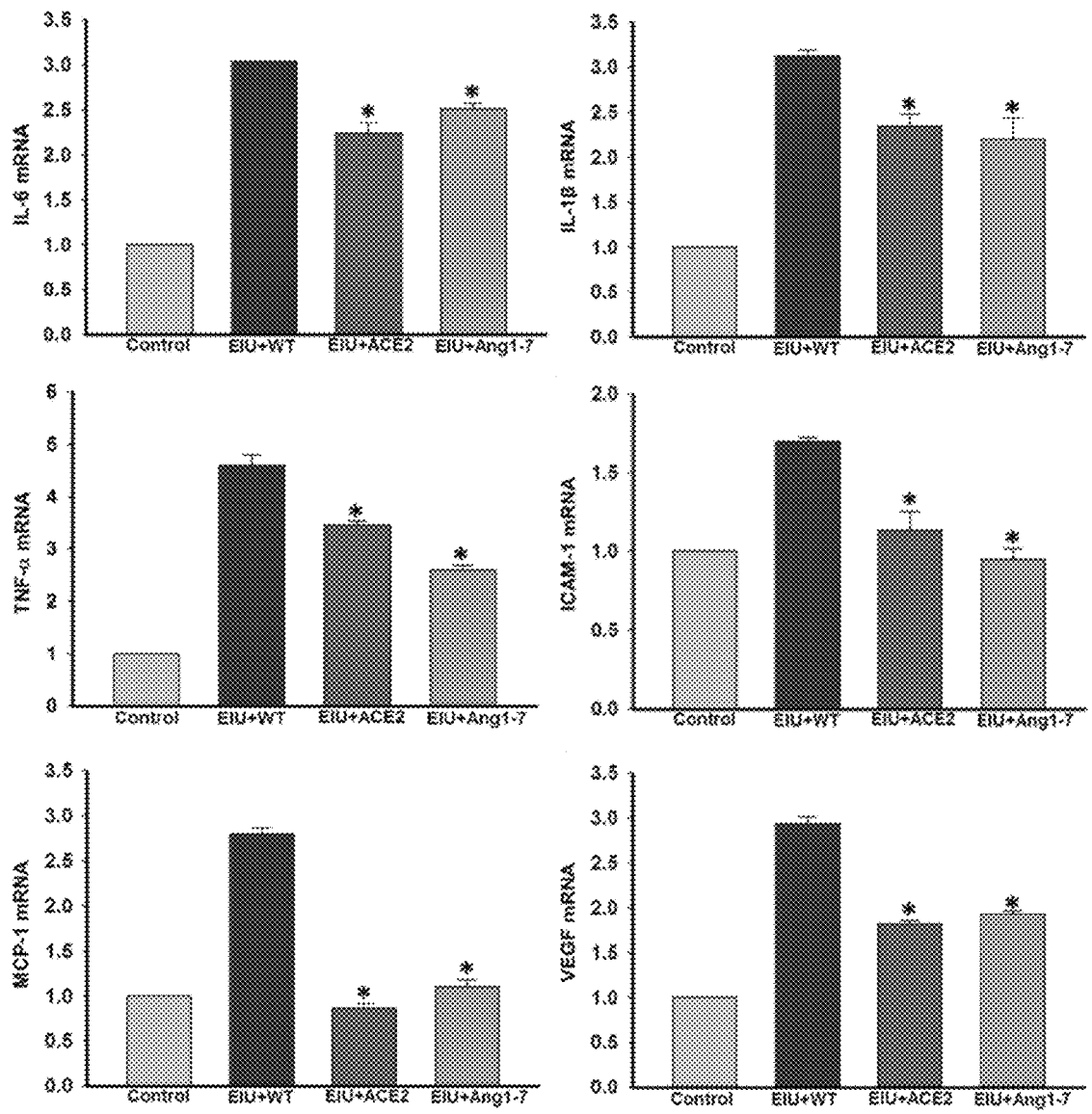
FIGS. 15A-15B. Real-time reverse transcriptase (RT)-PCR analysis of ocular mRNA levels of inflammatory cytokines (FIG. 15A) and RAS genes (FIG. 15B). Values on y-axis represent fold difference compared to age-matched wild-type control ocular samples for each gene. WT ctrl, non-fed wild-type control; WT+LPS, WT leaf fed & LPS injected; ACE2+LPS, CTB-ACE2 expressed leaf fed & LPS injected; Ang-(1-7)+LPS, CTB-Ang-(1-7) expressed leaf fed & LPS injected. Data expressed as mean+SD; (n=4 per group); * P<0.05 (versus WT+LPS group).

Oral Administration of Bioencapsulated CTB-ACE2 and CTB-Ang-(1-7) Reduced the Expression of the Inflammatory Cytokines in EIU Eyes To investigate the effects of ACE2 and Ang-(1-7) on the expression of inflammatory cytokines in EIU eyes, the mRNA levels of cytokine genes were determined by real-time RT-PCR. In the WT leaf fed mice, LPS caused a significant increase in mRNA levels of Interleukin-6 (IL-6), Interleukin-1β (IL-1β), Tumor necrosis factor-α (TNF-α) and vascular endothelial growth factor (VEGF) and this increase was reduced in mice fed with ACE2 or Ang-(1-7) leaf materials (FIG. 15a). These results suggest that ACE2 and Ang-(1-7) reduced infiltration of inflammatory cells and cytokine production through suppressing their gene expressions during EIU. To investigate the molecular mechanisms of leucocyte recruitment, the mRNA levels of intercellular adhesion molecule-1 (ICAM-1) and monocyte chemoattractant protein (MCP-1) were measured in EIU eyes. The expression of both ICAM-1 and MCP-1 was significantly increased in LPS induced EIU eyes in mice treated with WT leaf material and was significantly reduced in mice fed with CTB-ACE2 or CTB-Ang-(1-7) (FIG. 15a).

Figure 15B:
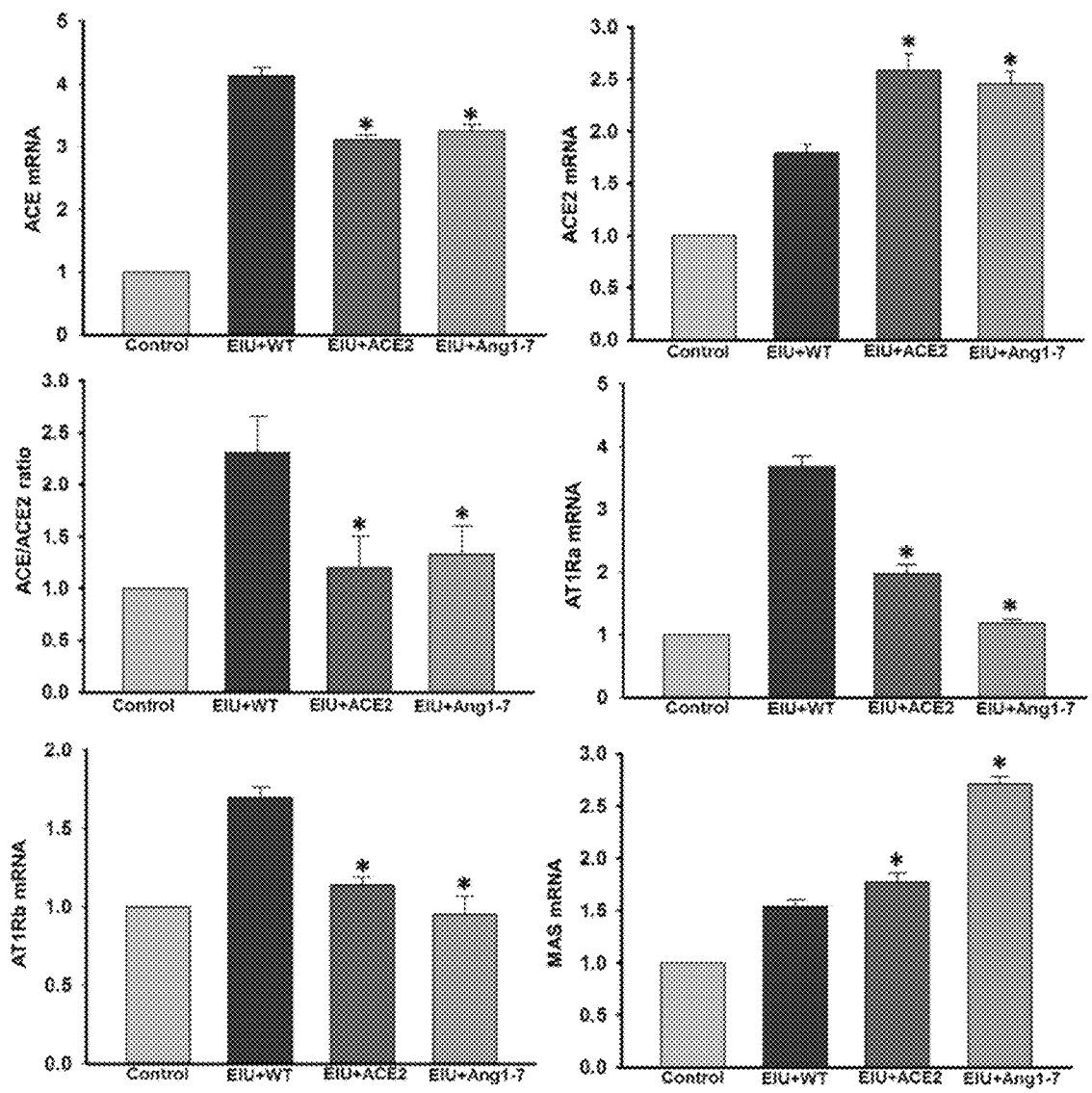

The Impact of Oral Administration of Bioencapsulated CTB-ACE2 and CTB-Ang-(1-7) on the Expression of the Retinal RAS Genes During EIU In addition to circulating RAS, all components of RAS have been detected in the retina and a local retina RAS may play an important role in modulating local immune responses [10,11,29]. We compared ocular mRNA levels of the key RAS genes in animals fed with ACE2 and Ang-(1-7) expressing leaf materials as well as untransformed WT leaf materials. LPS-induced EIU resulted in increased expression of both ACE and ACE2, however prominent increase in ACE (more than 4-fold increase) than ACE2 (less than 2-fold increase), resulted in increased ratio of ACE/ACE2 (FIG. 15b). CTB-ACE2 or CTB-Ang-(1-7) oral feeding normalized the shift of ACE/ACE2 ratio (FIG. 15b). The mRNA levels for receptors for Ang II (AT1Ra, AT1Rb) were also increased in EIU mice fed with control leaf material (~4-fold and 1.7-fold respectively) (FIG. 15b), both of which were significantly decreased in mice fed with CTB-ACE2 or CTB-Ang (1-7). There was a slight but significant increase in Mas, the receptor for Ang-(1-7). Interestingly the Mas mRNA level in the retina was further increased in mice fed with CTB-ACE2 (~2-fold increase), and even more increase in mice fed with CTB-Ang-(1-7) leaf material (~3-fold increase) (FIG. 15b), suggesting a possible feed-forward regulatory response in local retinal RAS.

Oral Delivery of Bioencapsulated CTB-ACE2 and CTB-Ang-(1-7) Attenuated Autoantigen Induced Uveoretinitis Experimental autoimmune uveoretinitis was induced in an autoimmune susceptible B10.RIII mouse strain by active immunization using a peptide derived from the retinal protein IRBP [30]. Evident inflammatory reactions such as mild to severe vasculitis, focal lesions, large confluent lesions, retinal hemorrhages and folding, corneal edema etc., were observed in WT leaf fed animals by fundoscopy examination at day 14 of EAU induction (FIG. 16A, a-b). However, mice fed with CTB-ACE2 or -Ang-(1-7) leaf materials showed significantly reduced inflammatory reactions (FIG. 16A, c-d, and e-f). The clinical scoring, using the criteria reported by Copland et al [31], showed that eyes from CTB-ACE2 or CTB-Ang-(1-7) fed animals had significantly improved clinical scores (EAU grade, 2.3±1.2 and 2.3±1.3 respectively) compared to eyes from animals fed with WT leaf (EAU grade, 3.4±0.53) (FIG. 16B).

Figure 17A:
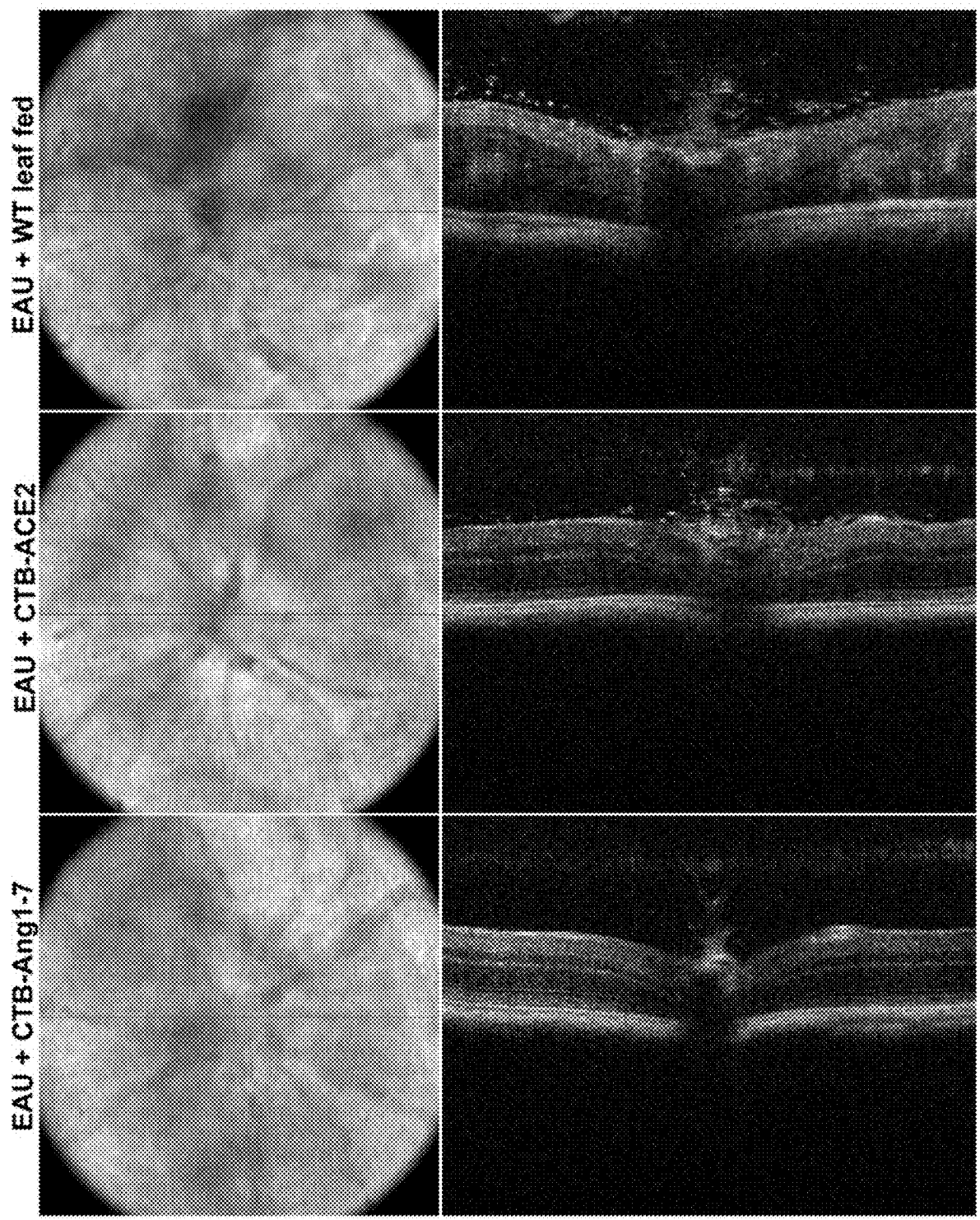
FIGS. 17A-17B. Assessment of retinal thickness on OCT images from EAU mice. Horizontal and cross sectional OCT images were obtained on day 14 after immunization. The retinal thickness was measured and averaged from five different frames of horizontal OCT scan images of single eye.
Figure 17B:
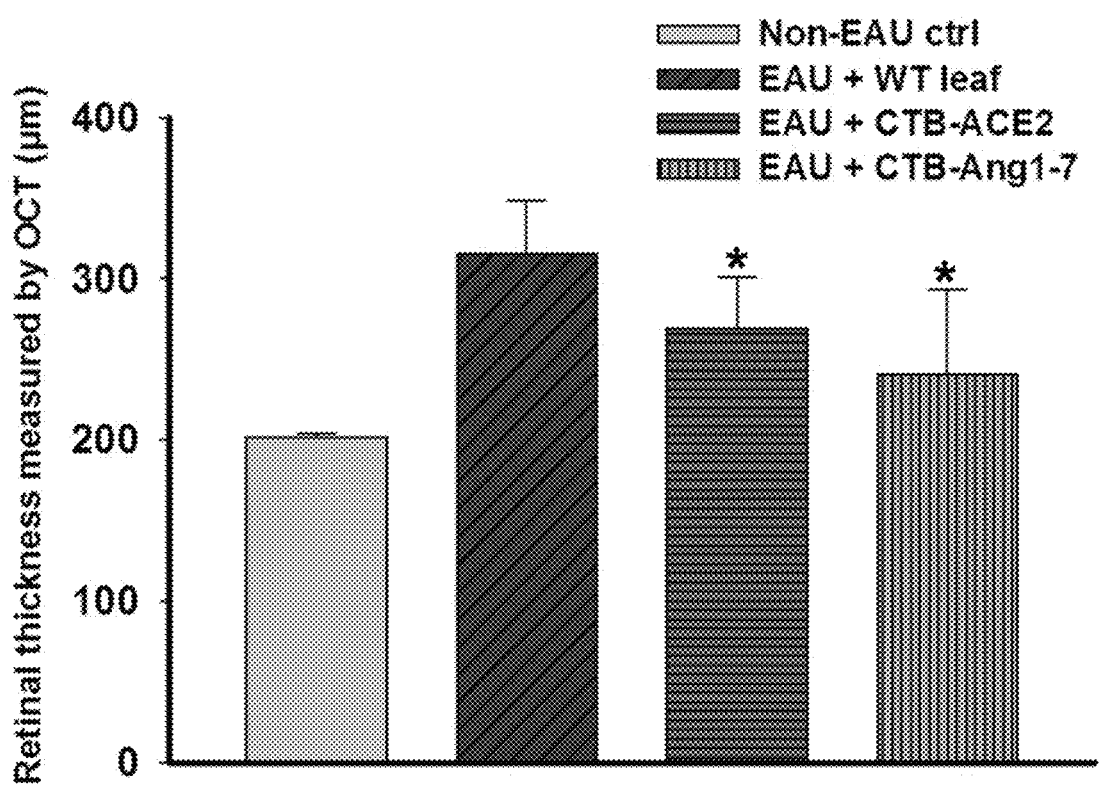

The uveoretinitis was also evaluated by OCT imaging on day 14 after immunization with IRBP. In few cases severe retinal pathology such as high level of cellular infiltration, edema, folds, and hemorrhages limited OCT resolution of retinal layers. In most cases, intravitreal cellular infiltration, retinal vasculitis, disorganized retinal layers and increased retinal thickness due to retinal folds and edema, can be easily visualized with OCT imaging as shown in FIG. 17a in untreated or WT leaf material treated animals, these pathologies are much improved in mice treated with CTB-ACE2 or Ang-(1-7) (FIG. 17a). Treatment with CTB-ACE2 or CTB-Ang-(1-7) leaf materials significantly reduced EAU-induced increased retinal thickness (269±32 μm and 241±52 μm respectively) compared to eyes treated with WT leaf (316±32 μm) (FIG. 17b).

Figure 18A:
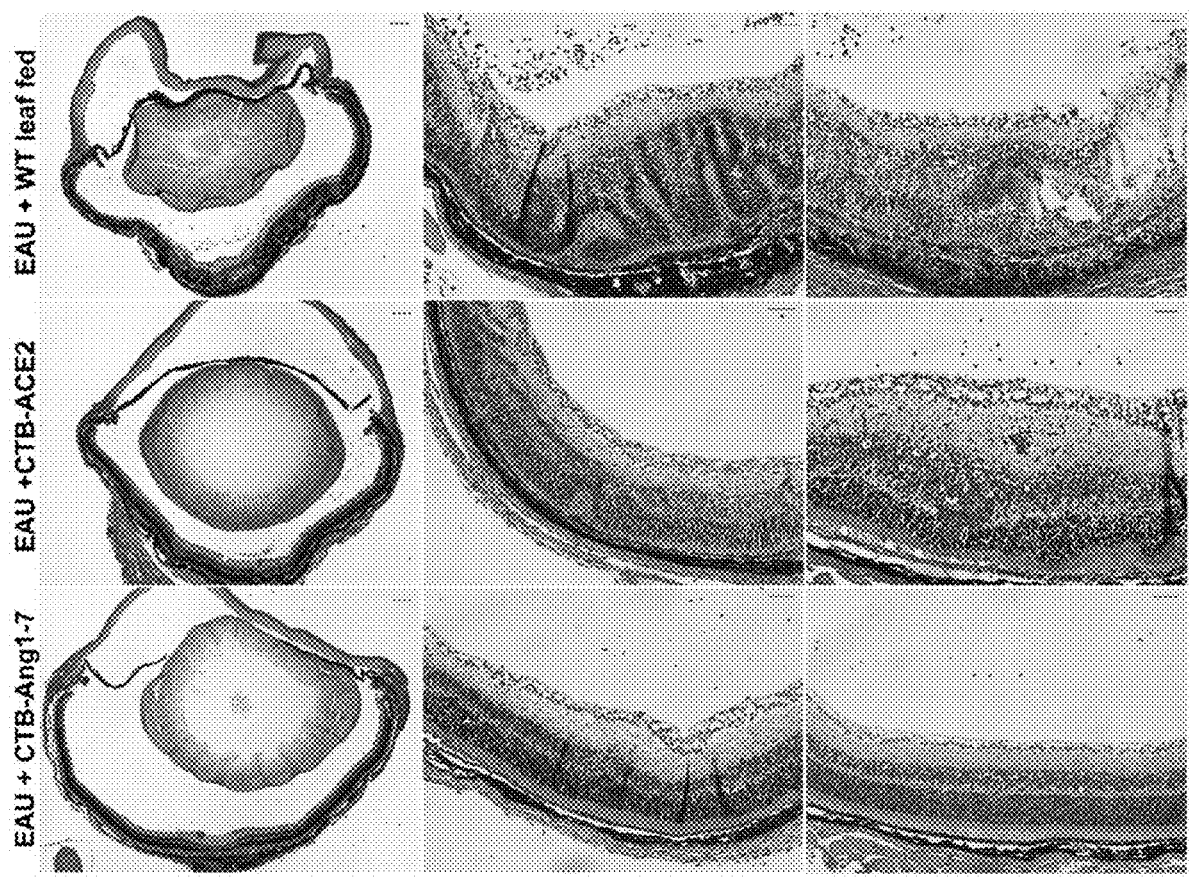
FIGS. 18A-18C. Histological evaluation of EAU. H&E staining, magnifications 4×, Bar=200 µm; and 20×, Bar=50 µm.
Figure 18B:
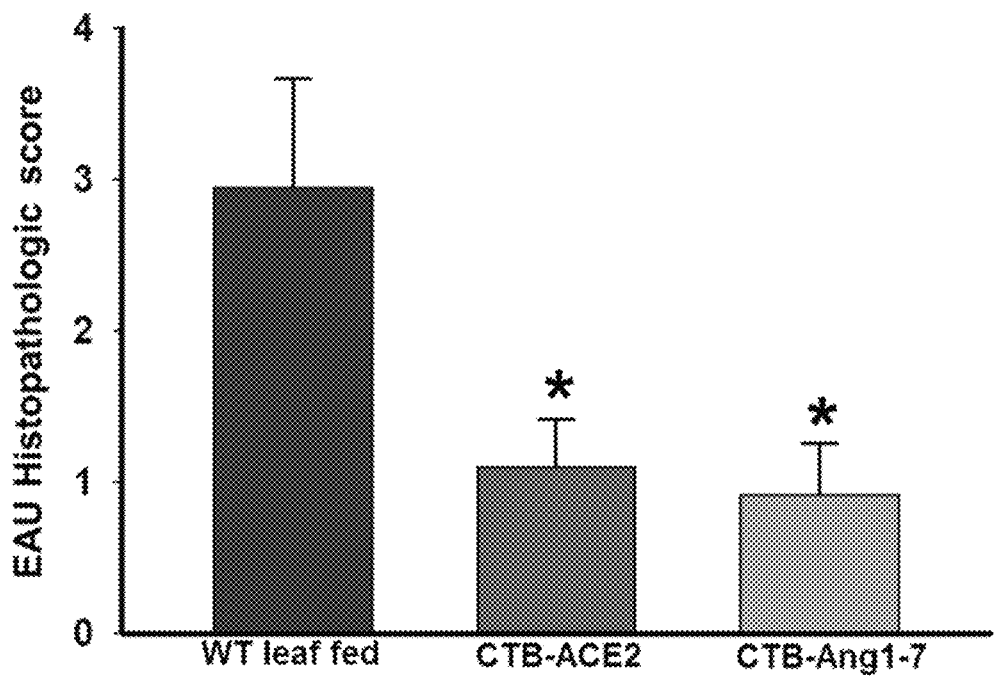
Figure 18C:
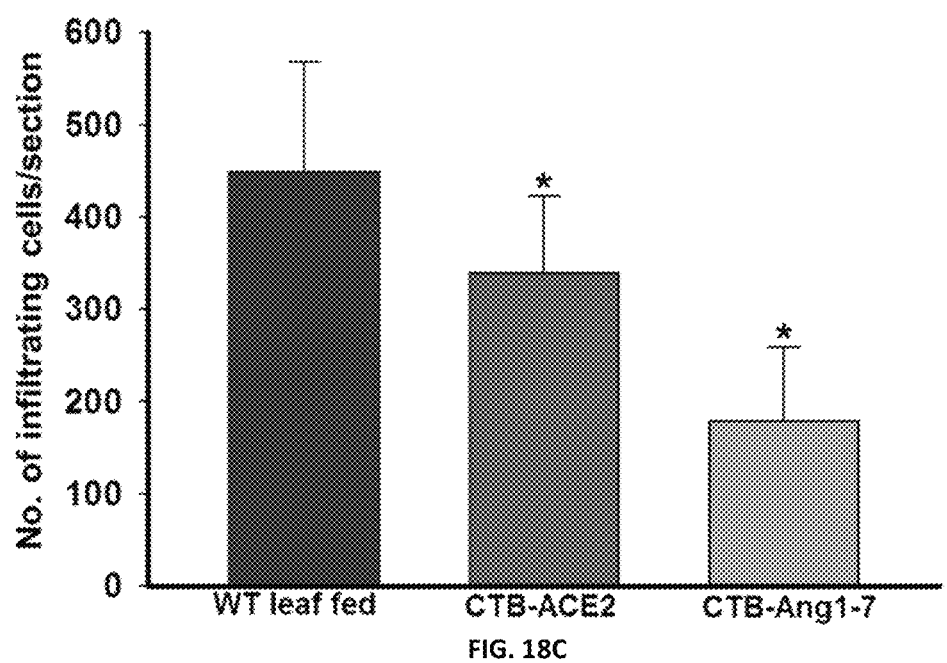

Oral Administration of CTB-ACE2 and CTB-Ang-(1-7) Ameliorates Histological Findings in the EAU Mice Histological examination on day 14 showed a severe intraocular inflammation evidenced by massive infiltration of inflammatory cells, intensive retinal vasculitits, and changes in the retinal thickness, folding of retina, as well as photoreceptor damage in the WT leaf fed mice (FIG. 18a). However, only scattered inflammation of inflammatory cells and minor retinal folding was observed in CTB-ACE2 or CTB-Ang-(1-7) treated animals (FIG. 18a). Histopathological grading, using the criteria reported by Thurau et al.[32] showed that WT leaf fed eyes (EAU grade, 2.95±0.717) had significantly severe inflammation as compared to CTB-ACE2 (EAU grade, 1.1±0.616) and CTB-Ang-(1-7) (EAU grade, 0.92±0.535) expressed leaf fed eyes (FIG. 18b). Similarly significantly higher numbers of inflammatory cells were observed in the posterior chamber of WT leaf fed mice compared to the CTB-ACE2/Ang-(1-7) expressed leaf fed mice (FIG. 18b).

Figure 19A:
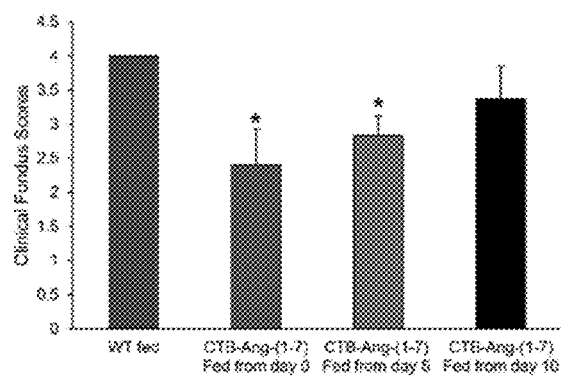
FIGS. 19A-19C. Evaluation of EAU from fundoscopic photographs, OCT and histopatholgy. EAU was induced in B10.RIII mice by immunization with IRBP in CFA. The treatment with CTB-Ang-(1-7) was delayed. The fundoscopic images were obtained on day 14 after immunization.
Figure 19B:
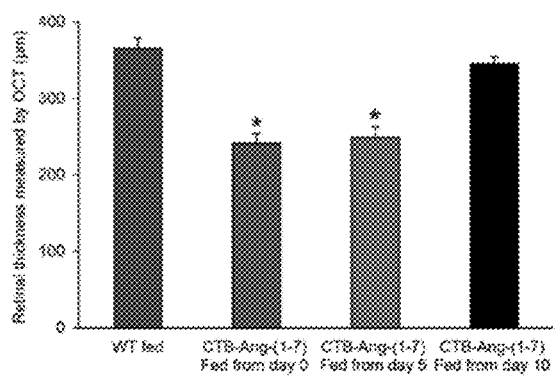
Figure 19C:
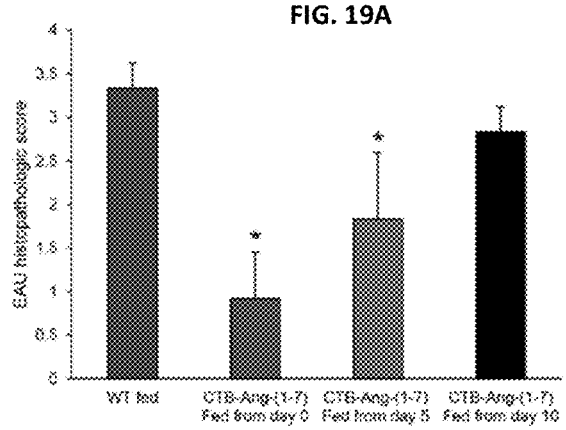
Figure 21A:
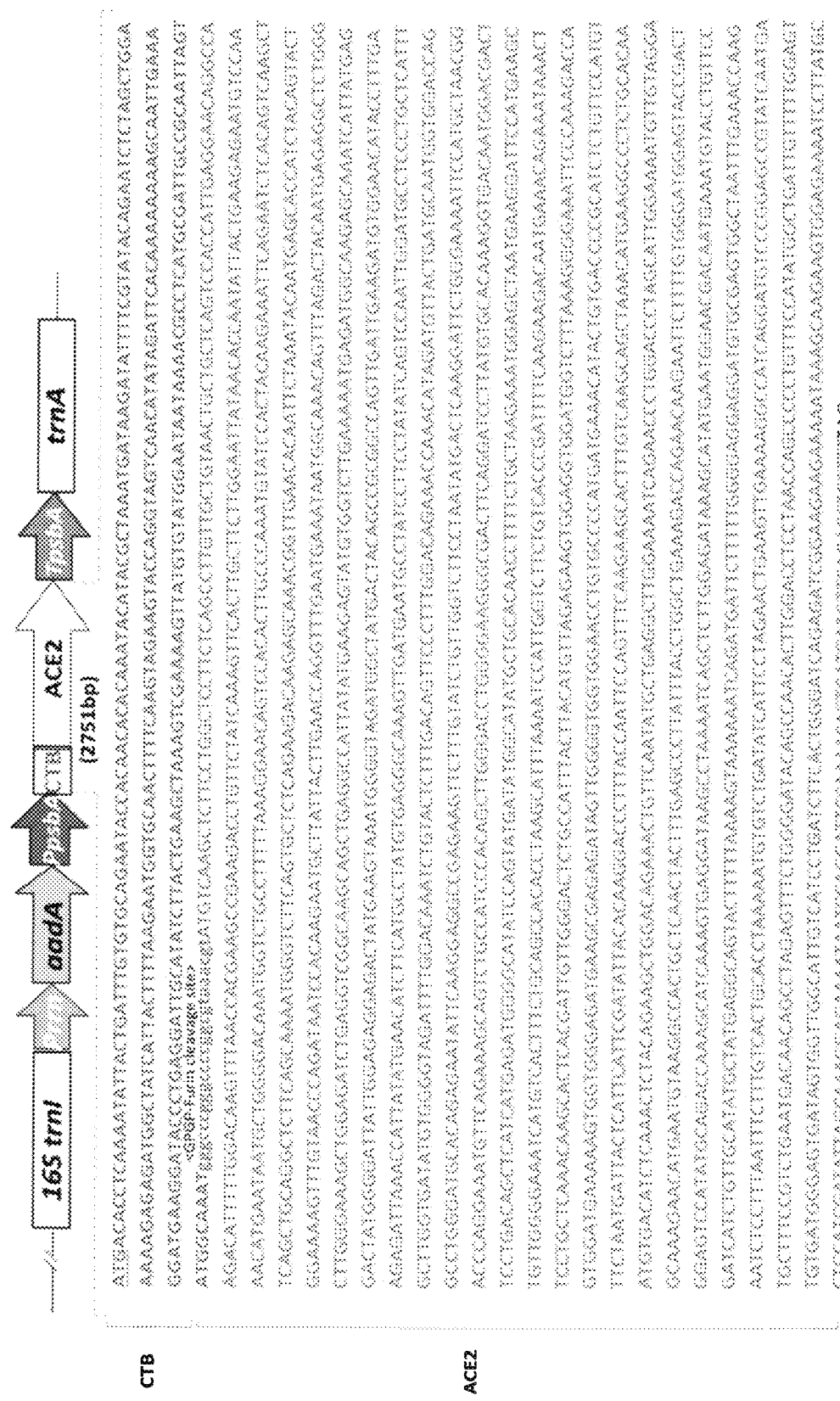
Figure 23:
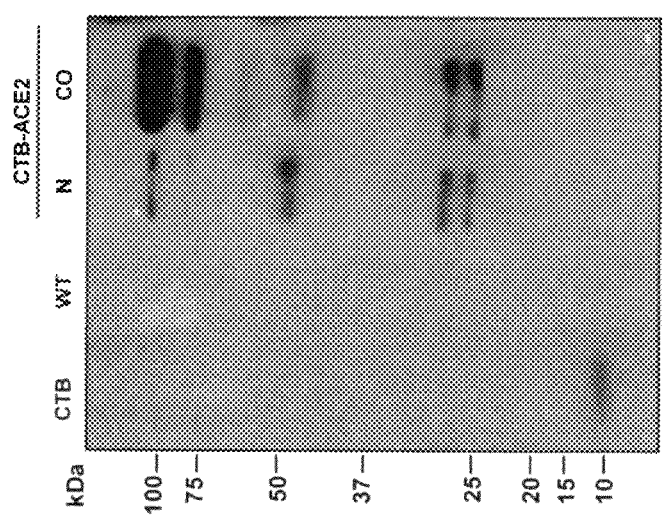
FIG. 23. Western blot analysis of ACE2-expressed transplastomic lettuce plants. 5 total protein extracted from wild type (WT), native CTB-ACE2 expressed (N) and codon-optimized CTB-ACE2 expressed (CO) were detected by anti-CTB antibody. CTB (5 ng) was loaded as positive control. The homoplasmic lettuce plants expressing codon-optimized ACE2 showed 7.7-fold higher expression than the native ACE2.

To determine whether CTB-Ang-(1-7) treatment can also improve EAU after its onset or during its progression, daily oral feeding was delayed to day 5 and day 10 after EAU induction, and continued to day 14 when mice were euthanized for evaluation. We observed that feeding from day 5 onward up to day 14 after IRBP injection is equally as effective as feeding from day 0, but feeding started at 10 after EAU induction had no improvement of ocular pathology (FIG. 19).

Discussion

In this study, we have developed an expression system to generate high levels of human ACE2 and Ang-(1-7) within plant chloroplasts using transplastomic technology. Oral gavage of plant cells expressing ACE2 and Ang-(1-7) fused with CTB in mice resulted in increased circulating and retinal levels of ACE2 and Ang-(1-7), reduced ocular inflammation in two different models: endotoxin-induced uveitis (EIU) and autoantigen induced experimental autoimmune uveoretinitis (EAU).

Among many advantages of transplastomic technology, the high copy number of a transgene, up to >10,000 copies per cell, is a key to successful high level expression of therapeutic proteins in chloroplasts. However, this advantage could be limited when human transgenes are not codon-optimized because the preference of codon usage of chloroplast is different from that of eukaryotic cell. The codon adjustment for chloroplast expression system is crucial for the efficient expression of human genes [33]. So, the relatively low expression ACE2 over the Ang-(1-7) is probably due to the use of native human gene sequence (805 amino acids). However, several other tools were incorporated into our system to offset low expression of the transgenes so that the contents of therapeutic proteins expressed in chloroplasts can be increased. For example, the expression of therapeutic proteins under the control of light-regulated strong chloroplast promoter, harvest of mature leaves at the end of day, and lyophilization of the harvested leaves. The chloroplast psbA promoter is light regulated and therefore harvesting leaves before sunset maximizes accumulation therapeutic proteins.

Moreover, the amount of therapeutic proteins in plant leaves can be concentrated by lyophilization (FIGS. 12c and 12d). The process of dehydration of the leaves under vacuum at −51° C. for 3 days can significantly reduce the risk of microbial contamination [14]. The long-term shelf life of the lyophilized proteins at room temperature can also decrease the cost associated with the cold chain of current injectable proteins [14]. The effect of lyophilization on the stability of proteins expressed in chloroplasts has been extensively studied in our lab under the condition at which temperature and pressure were set up at −51° C. and 27 mTorr, respectively, according to the chart of vapor pressure of ice provided by manufacturer. When the effect of duration of lyophilization was investigated, large protective antigen (PA, 83 kDa) expressed in lettuce chloroplasts was stable at 24, 48, and 72 hrs of lyophilization. In addition, the lyophilized antigen was more stable at room temperature than the commercially purified antigens stored at low temperatures. Further, the lyophilized PA was found to be stable up to 15 months at room temperature without any degradation [14]. Other transplastomic plants expressing CTB-exendin 4 [21] and CTB-Factor VIII [34] showed similar stability of fusion proteins and protection of their assembly, folding and disulfide bonds similar to fresh leaves.

Drug delivery to different compartments of the eye, particularly to the posterior segment of the eye, is a major challenge due to several barriers formed by both anatomical structure and the protective physiological mechanisms of the eye[13]. Large molecular weight therapeutics such as peptides/proteins and oligonucleotides are delivered mostly via intravitreal route. However, frequent administration via this route is often associated with many complications such as retinal detachment, endophthalmitis, and increased intraocular pressure [35, 36]. We demonstrate that oral administration of CTB-ACE2 increased ACE2 activity in sera and retina. Similarly increased level of plasma and retinal Ang-(1-7) was observed when the animals were orally administered with CTB-Ang-(1-7), as observed in previous study of oral delivery of bioencapsulated proteins across blood-brain and retinal barriers [12]. The increased level of the Ang-(1-7) could be stemmed from the fusion with CTB. The short peptide of Ang-(1-7) fused to CTB becomes stabilized in a form of pentameric structure in plant cells (FIG. 12*a*). However, only monomers are observed in sera once delivered into circulation. Considering that the efficiency of furin cleavage site depends on the flanking amino acid sequence of the fused protein [37], Ang-(1-7) fusion to CTB did not offer optimal furin cleavage site. Thus, the cleavage between CTB and Ang-(1-7) is not likely to be fast or efficient once the fusion protein gets into sera. In addition, the CTB fusion provides N-terminal protection for Ang-(1-7) so its stability is extended for several hours, while injectable Ang-(1-7) has a very short half-life in sera [38, 39]. Although the Ang-(1-7) level was increased in both plasma and retina (FIG. 13*d*), the level of Ang-(1-7) increase in plasma was less than in retina (FIG. 13*d*). This difference could be attributed to the increased retention in tissues (cells) and to their rapid clearance in the sera by proteases. Similar result was also observed in our previously published study in which GFP level was shown several fold higher in tissues than in sera [12,19]. Although EIU was originally used as a model of anterior uveitis because of its characteristic infiltration of leucocytes into the anterior chamber of the eye [4], growing evidences suggest that it also involves inflammation in the posterior segment of the eye, with recruitment of leucocytes that adhere to the retinal vasculature and infiltrate the vitreous cavity [3]. Our results demonstrate that enhanced level of ACE2/Ang-(1-7) in both circulation and ocular tissues suppressed the endotoxin-induced ocular inflammation, which is evident from significantly reduced number of infiltrating inflammatory cells in the iris-ciliary body, anterior and posterior chambers. This result is consistent with studies showing anti-inflammatory property of ACE2/Ang-(1-7) in other disease models [9]. The dose dependent study using bio-encapsulated lyophilized CTB-ACE2 in EIU model further confirmed that a dose of ~50 mg/day for four days can significantly prevent the endotoxin-induced inflammation. We also showed that increased ACE2/Ang-(1-7) significantly suppressed the LPS-induced ocular expression of IL-6, IL-10, TNF-α and VEGF. It has been reported that in EIU model, leucocytes are markedly attracted to inflamed ocular tissues such as the iris [40], vitreous cavity [41] and retina [42], with neutrophils and macrophages being major leucocyte constituents. MCP-1 is known as one of the important factors for leucocyte recruitment, and is up-regulated during EIU [43] whereas ICAM-1 is known to be the key molecule of leucocyte adhesion and/or transmigration [44]. Our study demonstrates that mice fed with ACE2/Ang-(1-7) leaf materials showed decreased ocular expression of MCP-1 and ICAM-1 in EIU eyes, contributing to the diminished inflammatory response by inhibiting leucocyte recruitment and adhesion in the ocular tissue. These results are consistent with the histopathology observation that LPS-induced acute inflammation caused the increase of inflammatory cell recruitment, while ACE2/Ang-(1-7) treatment significantly reduced the inflammatory cells in iris/ciliary body, anterior and posterior chamber.

It has been shown that ACE2/Ang-(1-7) may directly reduce inflammatory responses in immune cells such as macrophages [45]. Our study also shows modulatory ability of ACE2/Ang-(1-7) on local immune response and cytokine/chemokine expression. In fact the Mas receptor is expressed not only in retinal vascular cells, astrocytes and muller glia, but also in retinal neurons, consistent with its role in neuro-vascular and immune response modulation. Moreover, our results show that eyes with EIU are associated with decreased expression of ACE2 and Mas receptor and increased expression of vasoconstrictive axis genes such as ACE, AT1Ra, AT1Rb during EIU. This is prevented by ACE2/Ang(1-7), suggesting that the anti-inflammatory effect of ACE2/Ang-(1-7) may be associated with Mas receptor and ACE2 up-regulation, and down-regulation of ACE and AT1Ra/AT1Rb, resulting in reduction of ocular inflammation.

In this study, we also investigated the effect of oral administration of CTB-ACE2/Ang-(1-7) on the development of EAU in mice and showed significant improvement of EAU eyes in mice treated with CTB-ACE2/Ang-(1-7). The pathogenesis of EAU is different from EIU. EAU is defined primarily as posterior segment disease as the target antigens reside in the retina and characterized by cellular infiltrates, retinal folds, detachment, granulomatous infiltrates in the retina and choroid, vasculitis, retinal neovascularization, mild to severe photoreceptor loss [32]. Histopathological examination confirmed a significant overall reduction of disease severity in the CTB-ACE2/Ang-(1-7) treatment groups evaluated by non-invasive funduscopy and OCT imaging methods. Furthermore, the retinal detachment, photoreceptor layer damage, infiltration of inflammatory cells was markedly prevented by CTB-ACE2/Ang-(1-7) treatments. Some of the fundoscopically normal-looking eyes showed few foci of very mild cellular infiltrates on histological evaluation. This is consistent with the findings from OCT imaging, demonstrating a better correlation of histological findings and pathological changes revealed by non-invasive OCT imaging in the retina during EAU. Thus, oral administration of CTB-ACE2/Ang-(1-7) from the induction to peak of EAU was able to ameliorate the progression of disease evaluated by clinical funduscopic score, OCT imaging and histopathological observation. Moreover, delayed oral administration of CTB-ACE2/Ang-(1-7) from day 5 after EAU induction was also able to decrease the progression of EAU.

Increasing evidence has shown that shifting the balance of RAS towards the protective axis by activation of ACE2 or its product, Ang-(1-7) is beneficial and anti-inflammatory [9,46]. Our findings also demonstrate that oral administration of CTB-ACE2/Ang-(1-7) provides robust protective anti-inflammatory effects against the pathophysiology in both EIU and EAU models.

In conclusion, this study provides proof-of concept for production of therapeutically active ACE2/Ang-(1-7) bioencapsulated in plant cells for cost effective oral therapy for ocular applications and enhancing ACE2/Ang-(1-7) using this approach may provide a new avenue and a novel therapeutic strategy for the treatment of acute uveitis, autoimmune uveoretinitis and other ocular diseases.

REFERENCES FOR EXAMPLE 2

1. Mochizuki M, Sugita S, Kamoi K (2013) Immunological homeostasis of the eye. Prog Retin Eye Res 33: 10-27.
2. Read R W (2006) Uveitis: advances in understanding of pathogenesis and treatment. Curr Rheumatol Rep 8: 260-266.
3. Rosenbaum J T, McDevitt H O, Guss R B, Egbert P R (1980) Endotoxin-induced uveitis in rats as a model for human disease. Nature 286: 611-613.
4. Agarwal R K, Silver P B, Caspi R R (2012) Rodent models of experimental autoimmune uveitis. Methods Mol Biol 900: 443-469.
5. Paul M, Poyan Mehr A, Kreutz R (2006) Physiology of local renin-angiotensin systems. Physiol Rev 86: 747-803.
6. Santos R A, Ferreira A J, Verano-Braga T, Bader M (2013) Angiotensin-converting enzyme 2, angiotensin-(1-7) and Mas: new players of the renin-angiotensin system. J Endocrinol 216: R1-R17.
7. Marian A J (2013) The discovery of the ACE2 gene. Circ Res 112: 1307-1309.
8. Santos R A, Simoes e Silva A C, Maric C, Silva D M, Machado R P, et al. (2003) Angiotensin-(1-7) is an endogenous ligand for the G protein-coupled receptor Mas. Proc Natl Acad Sci USA 100: 8258-8263.
9. Simoes E S A, Silveira K, Ferreira A, Teixeira M (2013) ACE2, angiotensin-(1-7) and Mas receptor axis in inflammation and fibrosis. Br J Pharmacol 169: 477-492.
10. Verma A, Shan Z, Lei B, Yuan L, Liu X, et al. (2012) ACE2 and Ang-(1-7) confer protection against development of diabetic retinopathy. Mol Ther 20: 28-36.
11. Qiu, Y, Shil, P K, Zhu, P, Yang, H, Verma, A, et al. (2014) Angiotensin-converting enzyme 2 (ACE2) activator diminazene aceturate ameliorates endotoxin-induced uveitis in mice. Invest Ophthalmol Vis Sci 55: 3809-3818.
12. Kohli, N, Westerveld, D R, Ayache, A C, Verma, A, Shil P, Prasad T et al. (2014) Oral delivery of bioencapsulated proteins across blood-brain and blood-retinal barriers. Mol Ther 22: 535-546.
13. Rawas-Qalaji, M, Williams, C A (2012) Advances in ocular drug delivery. Curr Eye Res 37: 345-356.
14. Kwon, K C, Verma, D, Singh, N D, Herzog, R and Daniell, H (2013) Oral delivery of human biopharmaceuticals, autoantigens and vaccine antigens bioencapsulated in plant cells. Adv Drug Deliv Rev 65: 782-799.
15. Daniell, H, Singh, N D, Mason, H and Streatfield, S J (2009) Plant-made vaccine antigens and biopharmaceuticals. Trends Plant Sci 14: 669-679.
16. Flint, H J, Bayer, E A, Rincon, M T, Lamed, R and White, B A (2008) Polysaccharide utilization by gut bacteria: potential for new insights from genomic analysis. Nat Rev Microbiol 6: 121-131.
17. Flint, H J, Scott, K P, Duncan, S H, Louis, P and Forano, E (2012) Microbial degradation of complex carbohydrates in the gut. Gut Microbes 3: 289-306.
18. Limaye, A, Koya, V, Samsam, M and Daniell, H (2006) Receptor-mediated oral delivery of a bioencapsulated green fluorescent protein expressed in transgenic chloroplasts into the mouse circulatory system. FASEB J 20: 959-961.
19. Ruhlman, T, Ahangari, R, Devine, A, Samsam, M and Daniell, H (2007) Expression of cholera toxin B-proinsulin fusion protein in lettuce and tobacco chloroplasts—oral administration protects against development of insulitis in non-obese diabetic mice. Plant Biotechnol J 5: 495-510.
20. Davoodi-Semiromi, A, Schreiber, M, Nalapalli, S, Verma, D, Singh N D, Banks, R K et al. (2010) Chloroplast-derived vaccine antigens confer dual immunity against cholera and malaria by oral or injectable delivery. Plant Biotechnol J 8: 223-242.
21. Kwon, K C, Nityanandam, R, New, J S and Daniell, H (2013) Oral delivery of bioencapsulated exendin-4 expressed in chloroplasts lowers blood glucose level in mice and stimulates insulin secretion in beta-TC6 cells. Plant Biotechnol J 11: 77-86.
22. Verma, D, Moghimi, B, LoDuca, P A, Singh, H D, Hoffman, B E, Herzog, R W et al. (2010) Oral delivery of bioencapsulated coagulation factor IX prevents inhibitor formation and fatal anaphylaxis in hemophilia B mice. Proc Natl Acad Sci USA 107: 7101-7106.
23. Wilson, J P (1967) Surface area of the small intestine in man. Gut 8: 618-621.
24. Holmgren, J, Lonnroth, I, Mansson, J and Svennerholm, L (1975) Interaction of cholera toxin and membrane GM1 ganglioside of small intestine. Proc Natl Acad Sci USA 72: 2520-2524.
25. Fishman P H, Bradley R M, Hom B E, Moss J (1983) Uptake and metabolism of exogenous gangliosides by cultured cells: effect of choleragen on the turnover of GM1. J Lipid Res 24: 1002-1011.
26. Yu R K, Tsai Y T, Ariga T (2012) Functional roles of gangliosides in neurodevelopment: an overview of recent advances. Neurochem Res 37: 1230-1244.
27. Thomas, G (2002) Furin at the cutting edge: from protein traffic to embryogenesis and disease. Nat Rev Mol Cell Biol 3: 753-766.

28. Miyata T, Oshiro S, Harakuni T, Taira T, Matsuzaki G, et al. (2012) Physicochemically stable cholera toxin B subunit pentamer created by peripheral molecular constraints imposed by de novo-introduced intersubunit disulfide crosslinks. Vaccine 30: 4225-4232.
29. Fletcher E L, Phipps J A, Ward M M, Vessey K A, Wilkinson-Berka J L (2010) The renin-angiotensin system in retinal health and disease: Its influence on neurons, glia and the vasculature. Prog Retin Eye Res 29: 284-311.
30. Hankey D J, Lightman S L, Baker D (2001) Interphotoreceptor retinoid binding protein peptide-induced uveitis in B10.RIII mice: characterization of disease parameters and immunomodulation. Exp Eye Res 72: 341-350.
31. Copland D A, Wertheim M S, Armitage W J, Nicholson L B, Raveney B J, et al. (2008) The clinical time-course of experimental autoimmune uveoretinitis using topical endoscopic fundal imaging with histologic and cellular infiltrate correlation. Invest Ophthalmol Vis Sci 49: 5458-5465.
32. Thurau S R, Chan C C, Nussenblatt R B, Caspi R R (1997) Oral tolerance in a murine model of relapsing experimental autoimmune uveoretinitis (EAU): induction of protective tolerance in primed animals. Clin Exp Immunol 109: 370-376.
33. Daniell, H, Ruiz, G, Denes, B, Sandberg, L and Langridge, W (2009) Optimization of codon composition and regulatory elements for expression of human insulin like growth factor-1 in transgenic chloroplasts and evaluation of structural identity and function. BMC Biotechnol 9: 33.
34. Sherman, A, Su, J, Lin, S, Wang, X, Herzog, R W and Daniell, H (2014) Suppression of inhibitor formation against factor VIII in hemophilia A mice by oral delivery of antigens bioencapsulated in plant cells. Blood pii: blood-2013-10-528737.
35. Peyman G A, Lad E M, Moshfeghi D M (2009) Intravitreal injection of therapeutic agents. Retina 29: 875-912.
36. Wu H, Chen T C (2009) The effects of intravitreal ophthalmic medications on intraocular pressure. Semin Ophthalmol 24: 100-105.
37. Duckert P, Brunak S, Blom N (2004) Prediction of proprotein convertase cleavage sites. Protein Eng Des Sel 17: 107-112.
38. Iusuf D, Henning R H, van Gilst W H, Roks A J (2008) Angiotensin-(1-7): pharmacological properties and pharmacotherapeutic perspectives. Eur J Pharmacol 585: 303-312.
39. Mordwinkin N M, Russell J R, Burke A S, Dizerega G S, Louie S G, et al. (2012) Toxicological and toxicokinetic analysis of angiotensin (1-7) in two species. J Pharm Sci 101: 373-380.
40. Planck S R, Becker M D, Crespo S, Choi D, Galster K, et al. (2008) Characterizing extravascular neutrophil migration in vivo in the iris. Inflammation 31: 105-111.
41. Noda K, Miyahara S, Nakazawa T, Almulki L, Nakao S, et al. (2008) Inhibition of vascular adhesion protein-1 suppresses endotoxin-induced uveitis. FASEB J 22: 1094-1103.
42. Miyahara S, Kiryu J, Miyamoto K, Katsuta H, Hirose F, et al. (2004) In vivo three-dimensional evaluation of leukocyte behavior in retinal microcirculation of mice. Invest Ophthalmol Vis Sci 45: 4197-4201.
43. Satofuka S, Ichihara A, Nagai N, Yamashiro K, Koto T, et al. (2006) Suppression of ocular inflammation in endotoxin-induced uveitis by inhibiting nonproteolytic activation of prorenin. Invest Ophthalmol Vis Sci 47: 2686-2692.
44. Whitcup S M, Hikita N, Shirao M, Miyasaka M, Tamatani T, et al. (1995) Monoclonal-Antibodies against Cd54 (Icam-1) and Cd11a (Lfa-1) Prevent and Inhibit Endotoxin-Induced Uveitis. Experimental Eye Research 60: 597-601.
45. Souza L L, Costa-Neto C M (2012) Angiotensin-(1-7) decreases LPS-induced inflammatory response in macrophages. J Cell Physiol 227: 2117-2122.
46. Passos-Silva D G, Verano-Braga T, Santos R A (2013) Angiotensin-(1-7): beyond the cardio-renal actions. Clin Sci (Lond) 124: 443-456.
47. Hill, D R, Ford, L and Lalloo, D G (2006) Oral cholera vaccines: use in clinical practice. Lancet Infect Dis 6: 361-373.
48. Odumosu, O, Payne, K, Baez, I, Jutzy, J, Wall, N and Langridge, W (2011) Suppression of dendritic cell activation by diabetes autoantigens linked to the cholera toxin B subunit. Immunobiology 216: 447-456.
49. Kim, N, Cheng, K C, Kwon, S S, Mora, R, Barbieri, M and Yoo T J (2001) Oral administration of collagen conjugated with cholera toxin induces tolerance to type II collagen and suppresses chondritis in an animal model of autoimmune ear disease. Ann Otol Rhinol Laryngol 110: 646-654.
50. Phipps, P A, Stanford, M R, Sun, J B, Xiao, B G, Holmgren, J, Shinnkck, T et al. (2003) Prevention of mucosally induced uveitis with a HSP60-derived peptide linked to cholera toxin B subunit. Eur J Immunol 33: 224-232.
51. Stanford, M, Whittall, T, Bergmeier, L A, Lindblad, M, Lundin, S, Shinnick T et al. (2004) Oral tolerization with peptide 336-351 linked to cholera toxin B subunit in preventing relapses of uveitis in Behcet's disease. Clin Exp Immunol 137: 201-208.
52. Verma, D, Samson, N P, Koya, V and Daniell, H (2008) A protocol for expression of foreign genes in chloroplasts. Nat Protoc 3: 739-758.
53. Chen J, Qian H, Horai R, Chan C C, Caspi R R (2013) Use of optical coherence tomography and electroretinography to evaluate retinal pathology in a mouse model of autoimmune uveitis. PLoS One 8: e63904.

Example 3

Codon Optimization of ACE2 and Ang-(1-7)

In a recent study, Nakamura et al. disclose the importance of compatibility between the psbA 5'-UTR and its 5' coding sequence when using codon-optimized heterologous genes. Previously reported codon optimization studies used only smaller eukaryotic coding sequences (<30 kDa). However, there is a great need to express larger human genes (eg. Human blood clotting factor VIII>200 kDa) that would require optimization of not only codons but also compatibility with regulatory sequences for optimal translation initiation, elongation and greater understanding of tRNAs encoded by the chloroplast genome or imported from the cytosol. However, no systematic study has been done to utilize the extensive knowledge gathered by sequencing several hundred chloroplast genomes to understand codon usage and frequency of highly expressed chloroplast genes.

Among the 140 transgenes expressed in chloroplasts, >75% use the psbA regulatory sequences (Daniell et al., 2016). Most importantly, compatibility between the 5'-UTR of psbA and its coding region is important for efficient translation initiation (Nakamura et al., 2016). For these reasons, a new codon optimization program was developed using codon usage of the psbA genes from 133 sequenced chloroplast genomes (FIG. 20A). We first investigated expression of synthetic genes using only the most highly preferred codon for each amino acid, which is referred to as the "old" version in this study. When this resulted in even lower levels of expression than the native gene (see data presented below), a "new" codon optimizer algorithm was developed using codon usage hierarchy observed among sequenced psbA genes. See FIGS. 20B, C and D. Therefore, most of the rare codons in heterologous genes were modified based on codons with >5% frequency of use in the psbA genes.

In this study, the CNTB coding sequence was not codon-optimized because of its prokaryotic origin and high AT content (65.37%). Most importantly, the expression level of CNTB (native sequence) fused with proinsulin in tobacco chloroplasts reached up to 72% of total leaf protein (Ruhlman et al., 2010) and 53% of total leaf protein in lettuce chloroplasts (Boyhan and Daniell, 2011), indicating that there is no limitation on translation of the CNTB coding sequence in chloroplasts.

When the psbA-based codon table is compared with total chloroplast codon usage tables, which are generated based on all chloroplast genes of *Lactuca sativa* (57,528 codons from 189 coding sequences) or *Nicotiana tabacum* (34,756 codons from 137 coding sequences) (Nakamura et al., 2000), there was no significant difference in AT content of coding sequences; it varied between 59.59% and 61.76%. However, there are striking differences between psbA-based and total chloroplast gene-based codon tables when individual codons are compared. Ten rare codons identified in the psbA codon table (<5% usage frequency), (which were not used in codon-optimized sequences in the new version) were not identified as rare codons in the total chloroplast gene codon usage table. For example, CTC (leucine) is almost never used in psbA genes (0.1%) but this codon's usage is >6.4% in the lettuce or 7.5% in the tobacco total chloroplast codon table. Likewise, CGG (arginine) and ACG (threonine) are used with frequencies of 0.5% and 0.8%, respectively, in the psbA-based codon table, but the same codons are used with 7.6% and 9.6% frequency in lettuce or 8.3% and 10.8% frequency in tobacco total codon tables. Inadequate identification of rare codons in total chloroplast gene codon tables could be due to the averaging effect of combining highly and poorly expressed genes regardless of their translation efficiency in chloroplasts. This is true for the hierarchy in codon usage among synonymous codons. For example, the 5th codon in the hierarchy for leucine is CTG, which is used at a frequency of 3.7% in the psbA-based codon table; the difference in usage between the 6th codon (CTC, 0.1%) is 37 fold. However, there is no difference in the percentage of codon usage between 5th and 6th codons in lettuce or tobacco chloroplast gene codon tables; the lettuce codon table shows 6.7% (CTG, 5th) and 6.4% (CTC, 6th) frequency and the tobacco table shows 7.5% (5th codon) and 7.1% (6th codon) frequency. The disadvantage of using a total chloroplast gene-based codon table is quite obvious: real differences in codon preference in translation are masked, as reported previously (Surzycki et al., 2009). Expression of Angiotensin Converting Enzyme in Lettuce Chloroplasts.

Because of low expression level of native ACE2 in transplastomic plants, the creation of a codon optimized ACE2 polypeptide is described in the present example. To improve the production ACE2 in chloroplasts, we first developed new software for codon optimization by creating a database for codon usage of psbA genes from 133 plant species and an algorithm was developed to replace rare codons with preferred codons. The chloroplast psbA gene was chosen as a model because this is the most highly expressed chloroplast gene. The psbA based codon table showed no significant difference in AT content of coding sequences when compared to total chloroplast codon usage tables generated using all lettuce (57,528 codons from 189 coding sequences). However, there are major differences between a single gene based codon table and total gene based codon tables in the usage frequency of individual codons and hierarchy in codon usage. Further, eleven codons identified as rare codons in psbA gene based codon table were not identified as rare codons in chloroplast total gene based codon tables. For example, CTC for leucine is almost not used in psbA genes (0.1%) but the same codon is used at the frequency of 6.4% in lettuce; CGG for arginine in psbA genes (0.5%) but at the frequency of 7.6% in lettuce total chloroplast. Thus, codon-optimized ACE2 were optimized by changing the rare codons and codons usage frequency to resemble the chloroplast psbA gene (FIG. 20A). 481 codons including 59 rare codons out of 805 codons of ACE2 were replaced according to the psbA codon distribution (FIGS. 20 B, C, and D). As a result, AT content of the ACE2 gene was increased from 57% to 62.46%, and the frequency of codon usage is similar to psbA gene (FIG. 21A, native, FIG. 21B, optimized). Optimized sequences were then synthesized by GenScript Inc. Genetically modified lettuce lines were created by bombardment of chloroplast vectors into sterile leaves using the gene gun. Transplastomic lettuce shoots confirmed by PCR were cut and subjected to two further rounds of selection. After selection, transplastomic lettuce plants were transferred to greenhouse (FIG. 22A-22D). Total leaf protein was extracted from native and codon-optimized transplastomic plants and the protein expression level was compared by Western blot analysis. The transplastomic lettuce plants expressing codon-optimized ACE2 showed 7.7-fold higher expression than the native gene (FIG. 23).

CONCLUSION

The present example provides a codon optimized CTB-ACE2 polypeptide sequence which is expressed at significantly higher levels in lettuce chloroplasts. This increased expression should enhance the beneficial cardioprotective effects described in Example I and improve the anti inflammatory effects described in Example 2.

While a number of embodiments have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A composition comprising lyophilized plant material comprising a nucleic acid of SEQ ID NO: 24 encoding a fusion protein comprising angiotensin-converting enzyme 2 and cholera non toxic B subunit (CTB).

2. The composition of claim 1, wherein said lyophilized plant material comprises leaves obtained from a homoplasmic plant, and wherein the composition further comprises a fusion protein comprising angiotensin-(1-7) (Ang-(1-7)), and cholera nontoxic B subunit (CTB).

3. The composition of claim 1, wherein said plant is selected from the group consisting of lettuce, carrots, cauliflower, cabbage, low-nicotine tobacco, spinach, kale, and cilantro.

4. The composition of claim 2, wherein said fusion protein encoded by SEQ ID NO:24 contains a hinge peptide and furin cleavage site between said CTB and said ACE-2.

5. The composition of claim 2, wherein said fusion protein comprising Ang-(1-7) contains a hinge peptide and furin cleavage site between said CTB and said Ang-(1-7).

6. The composition of claim 1, further comprising recombinant or chemically synthesized ACE2 sequence of SEQ ID NO: 26.

7. The composition of claim 1 further comprising recombinant or chemically synthesized Ang 1-7 sequence of SEQ ID NO: 29.

8. A pies mid transformation vector comprising SEQ ID NO: 24.

9. A transplastomic plant transformed with a sequence of claim 8.

10. The transplastomic plant of claim 9 further comprising SEQ ID NO:26 and/or SEQ NO:29.

* * * * *

UNITED STATES PATENT AND TRADEMARK OFFICE
CERTIFICATE OF CORRECTION

PATENT NO. : 10,806,775 B2
APPLICATION NO. : 16/425243
DATED : October 20, 2020
INVENTOR(S) : Henry Daniell Page 1 of 1

It is certified that error appears in the above-identified patent and that said Letters Patent is hereby corrected as shown below:

In the Specification

Left-hand column, Lines 25-29, after the heading "STATEMENT OF FEDERAL FUNDING":
Delete:
"This invention was made with government support under grant nos. HL099980, HL102033, HL106687, HL109442, EY021752 and EY21721 awarded by the National Institutes of Health. The U.S. Government has certain tights in the invention."

And Insert:
-- This invention was made with government support under HL107904, HL099980, EY021752, HL102033, HL109442, EY021721, HL106687, and GM063879 awarded by the National Institutes of Health. The government has certain rights in the invention. --

Signed and Sealed this
Twenty-ninth Day of October, 2024

Katherine Kelly Vidal
*Director of the United States Patent and Trademark Office*